(12) United States Patent
Okatsu et al.

(10) Patent No.: US 8,785,430 B2
(45) Date of Patent: Jul. 22, 2014

(54) COMPOUND THAT CAN INHIBIT UBC13-UEV INTERACTIONS, PHARMACEUTICAL COMPOSITIONS AND THERAPEUTIC USES

(75) Inventors: Timothy Thomson Okatsu, Barcelona (ES); Johanna Scheper Sigmund, Barcelona (ES); Ángel Messeguer Peypooh, Barcelona (ES); Ángel Ramirez Ortiz, Madrid (ES); Maria Luz Ortiz Melguizo, legal representative, Módrid (ES); M$^a$ Carmen Fabrega Claveria, legal representative, Barcelona (ES); Gloria Sanclimens Pérez de Rozas, Barcelona (ES); Isabel Masip Masip, Barcelona (ES); Alejandra Moure Fernández, Barcelona (ES); Domingo González Ruiz, Cantoblanco (ES); Antonio Morreale de León, Cantoblanco (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 13/555,804

(22) Filed: Jul. 23, 2012

(65) Prior Publication Data

US 2013/0237529 A1  Sep. 12, 2013

Related U.S. Application Data

(62) Division of application No. 12/309,429, filed as application No. PCT/ES2007/000120 on Mar. 7, 2007, now Pat. No. 8,252,786.

(30) Foreign Application Priority Data

Jul. 20, 2006  (ES) .................................. 200601933

(51) Int. Cl.
*A61K 31/513* (2006.01)
*A61K 31/551* (2006.01)

(52) U.S. Cl.
USPC .................................... 514/218; 514/255.01

(58) Field of Classification Search
USPC ............................................ 514/218, 255.01
See application file for complete search history.

(56) References Cited

U.S. PATENT DOCUMENTS

2003/0069189 A1   4/2003  Brand et al.

FOREIGN PATENT DOCUMENTS

ES   2169690 A1   7/2002

OTHER PUBLICATIONS

International Search Report issued by the International Searching Authority (ISA/O.E.P.M.) on Aug. 1, 2007 in connection with International Application No. PCT/ES2007/000120.
WO 02/11750 A2 (The Government of The USA) Feb. 14, 2002.
Masip I. et al., "Desgin and synthesis of an optimized positional scanning library of peptoids: identification of novel multidrug resistance reversal agents", Bioorganic Medicinal Chemistry (2005), vol. 13, pp. 1923-1929.
Masip, I. et al., "Synthesis of a Library of 3-Oxopiperazinium and Perhydro-3-oxo-1,4-Diazepinium Derivatives and Identification of Bioactive Compounds", J. Com. Chem. (2004), vol. 6; n° 1, pp. 135-141.
U.S. Appl. No. 12/309,429.

*Primary Examiner* — Rebecca Anderson
*Assistant Examiner* — Karen Cheng
(74) *Attorney, Agent, or Firm* — Gary J. Gershik; Cooper & Dunham LLP

(57) ABSTRACT

The invention relates to a compound (I) wherein R is a heterocyclyl radical; $R_1$ and $R_2$ are independently H or alkyl; $R_3$ is H, alkyl, cycloalkyl, cycloalkylalkyl, alkenyl, aryl, arylalkyl, heterocyclyl or heterocyclylalkyl; $R_4$ and $R_5$ are independently H or alkyl; q is a number selected from 0 and 1; and the salts, solvates, prodrugs or stereoisomers thereof having inhibitory activity for UBC13-UEV interactions and which can be used in the production of pharmaceutical compositions intended for antitumor therapy or the treatment and/or prophylaxis of diseases associated to metabolic pathways involving the UBC13 enzyme, metabolic pathways involving transcriptional factor NF-κB, or pathways involving PCNA or RAD6.

$$R-(CR_1R_2)q-CO-N(R_3)-C(R_4R_5)-CO-NH_2 \quad (I)$$

17 Claims, 13 Drawing Sheets

US 8,785,430 B2

COMPOUND THAT CAN INHIBIT UBC13-UEV INTERACTIONS, PHARMACEUTICAL COMPOSITIONS AND THERAPEUTIC USES

This application is a divisional of U.S. Ser. No. 12/309,429, filed on Mar. 17, 2011 now U.S. Pat. No. 8,252,786 a §371 national stage of PCT International Application No. PCT/ES2007/000120, filed Mar. 7, 2007, which claims priority of Spanish Patent Application No. P20060133, filed Jul. 20, 2006, the contents of all of which are hereby incorporated by reference into this application.

FIELD OF THE INVENTION

This invention is within the field of medical chemistry, and more specifically, it relates to the development of therapeutic compounds with inhibitory activity for UBC13-UEV interactions, and to the production or the use of pharmaceutical compositions intended for antitumor therapy or intended for the treatment and/or prophylaxis of diseases associated to metabolic pathways involving the UBC13 enzyme, metabolic pathways involving the transcriptional factor NF-κB, or pathways involving PCNA or RAD6.

STATE OF THE ART

The post-translational modification of proteins known as ubiquitylation consists of the formation of isopeptide bonds between a lysine of a substrate protein and the carboxy-terminal glycine of the ubiquitin peptide [1]. The ubiquitin (Ub) molecule is a polypeptide with 76 amino acids, abundant in cytosol and in cell nuclei. A Ub molecule forms a thioester bond with an E1 enzyme (Ub-activating enzyme) which, in a reaction requiring ATP, activates a Ub molecule, such that the latter is in a condition facilitating the formation of a thioester bond with the catalytic cysteine of a second class of enzymes, called E2 or ubiquitin-conjugating enzyme. In humans there is a single E1 enzyme, whereas there may be close to 30 E2 type enzymes. An E2 enzyme can transfer a Ub molecule to a substrate protein, with the formation of an isopeptide bond between the carboxy-terminal glycine of the Ub and a lysine of the substrate protein. The modification of a substrate protein by means of the covalent addition of a ubiquitin unit is called monoubiquitylation. The same E2 enzyme can catalyze the transfer of a Ub molecule to another Ub molecule previously bound to a substrate protein, with the formation of isopeptide bonds between ubiquitins. This reaction can be repeated a number of times, giving rise to the formation of polyubiquitin chains, this process being known as polyubiquitylation. A ubiquitin molecule has seven lysines, any of which can be used to form isopeptide bonds between ubiquitins. Experiments in which the abundance of different types of polyubiquitin chains is determined indicate that the lysines of the ubiquitin molecule most used in the formation of polyubiquitin chains are those located in positions 29, 48 and 63 of ubiquitin [2, 3]. The formation on substrate proteins of polyubiquitin chains with four or more Ub units through isopeptide bonds with the lysine in position 48 (K48) is a signal which is recognized by subunits of the proteasome regulatory particle [4], whereby the protein thus modified is processed and degraded by the proteasome. In contrast, polyubiquitin chains which are formed by means of isopeptide bonds through the lysine in position 63 (K63) of ubiquitin do not seem to be recognized by the proteasome [5], and therefore this type of polyubiquitylation is not a signal for the proteasomal processing and degradation of the modified protein. Very little is known of the function of the other forms of polyubiquitylation, or of the consequences that said modifications have on the substrate proteins. Polyubiquitylation by lysine 48 (K48) of ubiquitin is called "canonical" polyubiquitylation, whereas the polyubiquitylations using any of the other lysines are called "non-canonical" or "variant" polyubiquitylations [6]. Many E2s can catalyze the transfer of Ub to form K48 or K29 type polyubiquitin chains, whereas the formation of K63 type polyubiquitin chains seems to specifically require the heterodimer UBC13-UEV1 or UBC13-UEV2 [6]. The generation of polyubiquitin chains is counteracted by means of the activity of hydrolases (isopeptidases) specific for the type of bond (K48 or K63).

Two of the biochemical processes requiring the heterodimer UBC13-UEV1 and its activity for mediating K63 type polyubiquitylation are DNA repair mediated by PCNA (proliferating cell nuclear antigen) [7] and signal transmission initiated by cytokines such as TNFα or IL-1 [8]. In the *Saccharomyces cerevisiae* yeast, the heterodimer Ubc13p-Mms2p (Mms2p is the orthologous *S. cerevisiae* protein of UEV1 and UEV2) is essential for the modification by variant (K63 type) polyubiquitylation of PCNA [7-11], participating in the RAD6 (ubiquitin-conjugating enzyme)-dependent translesion DNA repair pathway, known as "error-free" [12-16]. The protein PCNA is modified by SUMOylation (covalent binding of a SUMO molecule) at the start of phase S, which provides it with stability, allowing its activity in DNA replication during this phase of the cell cycle [7, 9]. Outside phase S, PCNA is modified by canonical polyubiquitylation by the Rad6p-conjugating enzyme associated to the ubiquitin ligase Rad18p. However, in response to genotoxic damage, a nuclear entrance of the heterodimer Ubc13p-Mms2p occurs, which, associated to the ubiquitin ligase Rad5p, catalyzes the K63 type polyubiquitylation of PCNA, in competition with the modification by canonical polyubiquitylation mediated by Rad6p, thus preventing the degradation of PCNA, which can thus be used in the translesion repair of nicks in DNA [7-11, 17]. In mammals, it has not been unequivocally demonstrated that PCNA is modified by variant polyubiquitylation mediated by UBC13-UEV1 (or UBC13-UEV2), and therefore, unlike the *S. cerevisiae* yeast, the role of this type of substrate modification in PCNA-dependent DNA repair is not clear.

In mammalian cells, it has been demonstrated that the polyubiquitylation activity catalyzed by UBC13-UEV1 is essential for the heterodimerization of the TRAF2 and TRAF6 adaptor protein following the binding of TNFα with its receptor [18-20], or the heterodimerization of TRAF6 induced by IL-1 [21]. This heterodimerization stimulates the ubiquitin ligase activity of TRAF2 or TRAF6, which recruit UBC13-UEV1 for a K63 type chain autopolyubiquitylation. These K63 polyubiquitin chains are recognized by the TAB2 or TAB3 proteins, forming a complex with the TAK1 protein kinase, activating it [22], which in turn phosphorylates and activates another kinase, IKKα, which initiates a signaling cascade leading to the phosphorylation and degradation of IκB, the cytoplasmic NFκB inhibitor, which can thus be translocated to the nucleus and exert its transcription regulator action [18-22].

Therefore, the heterodimer UBC13-UEV1 (or UBC13-UEV2) is an essential regulator of two processes as important as the inflammation mediated by cytokines (TNFα) and, at least in yeasts, postreplication repair in response to genotoxic damage. There are other biological processes requiring K63 type polyubiquitylation mediated by UBC13-UEV1 (or UBC13-UEV2), such as motility [23], ligand-dependent endocytosis [24], or antigenic T cell activation [25]. Therefore, there are many biological processes which can be mediated by this post-translational modification, and the study of which represents a new field of research which has hardly started.

The structure of the heterodimer formed by UBC13 and UEV proteins [26, 27] shows an interaction interface in which the most striking characteristic is the participation, in UBC13, of 2 very delimited hydrophobic pockets on which also hydrophobic residues of the UEV protein (Mms2p, UEV1 or UEV2) dock, especially Phenylalanine in position 8, Proline in position 5 and Isoleucine in position 36. These interactions are stabilized by electrostatic interactions involving polar residues located on both sides of the hydrophobic interactions. This configuration is unique between ubiquitin-conjugating enzymes and therefore highly specific for the interaction between UBC13 and any of the UEV proteins (Mms2p, UEV1 and UEV2) [26-28]. This fact, added to what is delimited by the hydrophobic pockets in UBC13 participating in the interaction with UEV proteins, makes this interface an interesting target for designing peptide mimetic compounds interfering with it. The inhibition of the formation of this heterodimer should affect its catalytic activity and therefore the K63 type polyubiquitylation of relevant substrates, implying a blockage of the processes in which this post-translational modification participates. To that effect, it should be pointed out that it has been demonstrated that the post-translational modification of UBC13 by means of covalent binding of the small ISG15 protein inhibits its catalytic activity [29, 30]. This observation can be very interesting to study the effect of the inhibition of UBC13 in different biological systems, although it must be pointed out that ISG15 modifications affect many other proteins.

The design of molecules intended for the recognition of protein surfaces and having the capacity to modulate biologically relevant protein-protein interactions is considered one of the greatest challenges of biotechnology in the meeting point between Chemistry and Biology and with a huge potential in therapeutics. However, and although a number of proteasome inhibitors [31, 32], or specific inhibitors of enzyme activities involved in ubiquitylation [33, 34] have been developed and described, no inhibitor of the formation of K63 type polyubiquitin chains, nor any specific inhibitor of the formation of other types of polyubiquitin chains (K48, K29, K6, etc.) has been described to date. Likewise, other pharmacological inhibitors of the UBC13 ubiquitin-conjugating enzyme are not known either.

SUMMARY OF THE INVENTION

The present invention relates to a new family of compounds of formula (I) having inhibitory activity for UBC13-UEV interactions or inhibitory activity for the enzymatic activity of UBC13, therefore they are useful in antitumor therapy or in the treatment and/or prophylaxis of pathologies or diseases associated to metabolic pathways involving the UBC13 enzyme or to metabolic pathways involving transcriptional factor NF-κB.

In the present invention, the expression "pathologies or diseases associated to metabolic pathways involving the UBC13 enzyme or to metabolic pathways involving transcriptional factor NF-κB" includes those diseases in which UCB13 or NF-κB have no direct causal role in the disease/pathology but rather they are involved in some way in the development of said disease/pathology, for which reason the compounds of formula (I) of the present invention are useful in antitumor therapy or in the treatment and/or prophylaxis of pathologies or diseases associated to metabolic pathways involving the UBC13 enzyme or to metabolic pathways involving transcriptional factor NF-κB.

Thus, a first aspect of the present invention relates to compounds of formula (I), as well as the salts, solvates, prodrugs and stereoisomers thereof (compounds of the invention) as described below.

A second aspect of the invention relates to a process for synthesizing said compounds of formula (I), the salts, solvates, prodrugs and stereoisomers thereof.

An additional aspect of the invention relates to compounds of formula (I), the salts, solvates, prodrugs and stereoisomers thereof for medical use.

Another additional aspect of the invention relates to the use of the compounds of formula (I), the pharmaceutically acceptable salts, solvates, prodrugs or stereoisomers thereof for preparing a medicinal product intended for the treatment and/or prophylaxis of pathologies or diseases associated to metabolic pathways involving the UBC13 enzyme.

Another additional aspect of the invention relates to the use of the compounds of formula (I), or a pharmaceutically acceptable salt, solvate, prodrug or stereoisomer thereof for producing a medicinal product intended for the treatment and/or prophylaxis of pathologies or diseases associated to metabolic pathways involving transcriptional factor NF-κB.

In another additional aspect, the invention relates to the use of the compounds of formula (I), the pharmaceutically acceptable salts, solvates, prodrugs or stereoisomers thereof, or the mixtures thereof, for producing a medicinal product intended for antitumor therapy, wherein said medicinal product is an antagonist of, or inhibits, the genotoxic damage tolerance pathway mediated by PCNA and RAD6 causing chemo- or radiosensitizing effects.

Likewise, another additional aspect of the invention relates to the use of the compounds of formula (I) in the production of a medicinal product for increasing the sensitivity of a mammal to the treatment with an antitumor agent.

Finally, another aspect of the invention relates to a pharmaceutical composition comprising a compound of formula (I), or a pharmaceutically acceptable salt, prodrug, solvate or stereoisomer thereof, in a therapeutically effective amount, together with a pharmaceutically acceptable carrier, adjuvant or vehicle.

DETAILED DESCRIPTION OF THE INVENTION

The design of molecules intended for the recognition of protein surfaces and having the capacity to modulate biologically relevant protein-protein interactions is considered one of the greatest challenges of biotechnology in the meeting point between Chemistry and Biology and with a huge potential in therapeutics.

In this sense, the UBC13 enzyme is a promising therapeutic target for designing new therapeutic compounds. As a result, a process was designed which allows identifying small molecules capable of competitively interfering with the interaction between UBC13 and UEV1, the starting hypothesis being that the inhibition of this interaction would inhibit the capacity of UBC13 to form K63 type polyubiquitin chains. The methodologies applied for this pharmacological development prioritize, on one hand, the bioavailability of inhibitory compounds (i.e., their capacity for intracellular localization and entrance), on the other hand, the specificity of interference with the UBC13-UEV1 interaction, and, finally, the spatial and charge adjustment of these small molecules to the surface used by UBC13 to interact with UEV1. The process performed in the present invention sequentially combines:

(1) An experimental screening of a combinatorial chemical library of N-alkylglycines (peptoids) to select those with the capacity to specifically inhibit this interaction, determined by two-hybrid assays in yeasts. The screening method used allows simultaneously approaching and solving both the bioavailability of small molecules and the specificity of the inhibition of the interaction between UBC13 and UEV1, since relevant protein-protein interaction controls are used.

(2) A computational optimization to determine the molecular docking on the surface of UBC13 of the peptoids selected in the previous step.

(3) The synthesis of medicinable small molecules with inhibitory activity for the UBC13-UEV1 interaction. The virtual optimization data generated in the previous step have been used as a guideline for this synthesis.

Figure 1:
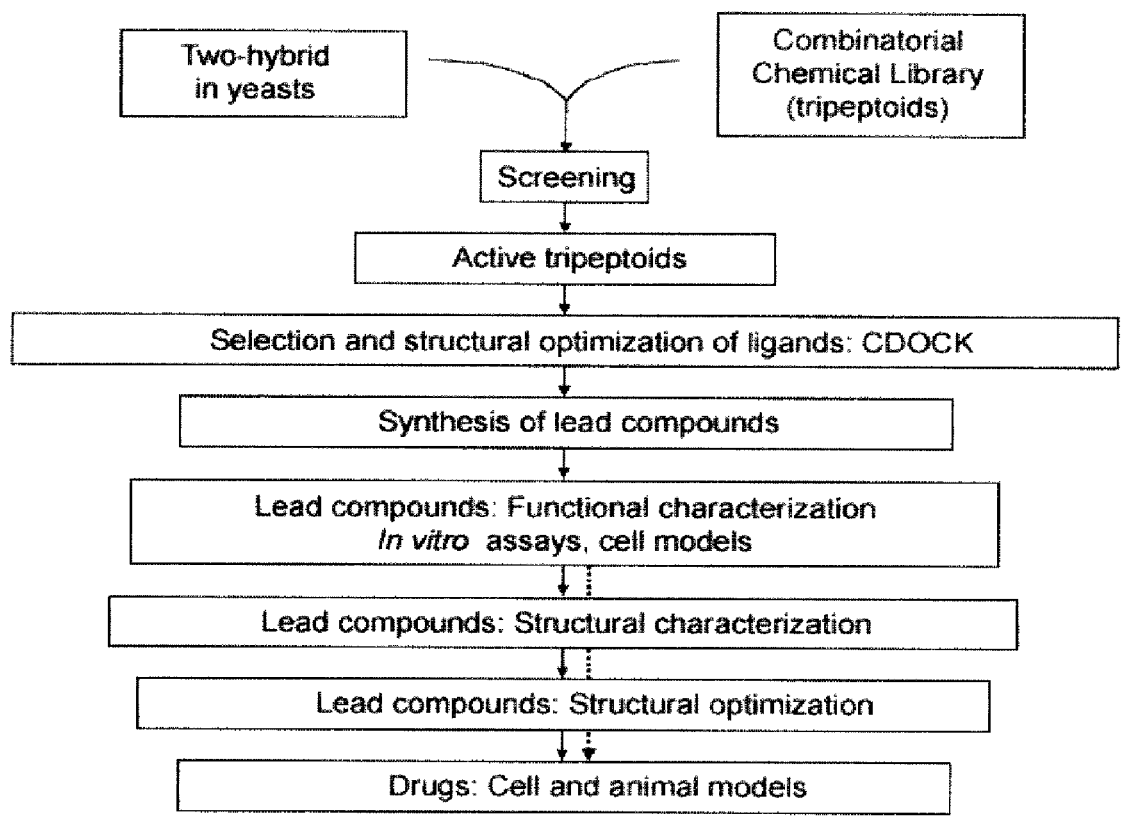
FIG. 1. Diagram of the steps and methodologies followed in the present invention for developing inhibitors of the interaction between UBC13 and UEV1.

(4) A characterization of the in vitro and in vivo functional effects of the compounds synthesized in the previous step. This characterization included the determination of the capacity of these compounds to inhibit the ubiquitin-conjugating activity of UBC13-UEV1, as well as to interfere with several of the cell processes which are known to be regulated by this enzyme. FIG. 1 schematically shows the steps and processes followed for this pharmacological development. The general structure (II) of the combinatorial modular chemical library of peptoids used in this screening is shown below:

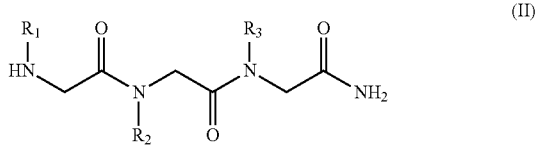

(II)

wherein $R^1$, $R^2$ and $R^3$ respectively represent the chemical diversity used in the construction of the chemical library [35].

The inventors of the invention have thus identified a new family of compounds with general formula I capable of inhibiting the interaction between UBC13 proteins and UEV proteins (Mms2p, UEV1 and UEV2, see Example 4), capable of competitively inhibiting the type K63 polyubiquitylation activity of this enzyme and causing biological effects at pharmacologically effective concentrations. These compounds competitively inhibit the correct interaction between UBC13 proteins and the UEV1 protein, thus preventing their enzymatic activity to form polyubiquitin chains in the mode known as "K63 type polyubiquitylation", the latter being the mechanism whereby these compounds exert their activity (Example 5), thus modulating in turn all those biochemical pathways and biological processes modulated by this K63 type polyubiquitylation.

The biological activities of the drugs object of the present invention reflect the biochemical pathways which are normally regulated by variant polyubiquitylation variant mediated by UBC13-UEV1, UBC13-UEV2 and Ubc13p-Mms2p. In particular, the polyubiquitylation mediated by this heterodimeric enzyme regulates, on one hand, DNA repair by the pathway known as RAD6-dependent "error-free" pathway, (Example 6), and, on the other hand, the activation of transcriptional factor NF-κB induced by cytokines and other stimuli. As a result of this activity, these drugs sensitize both *Saccharomyces cerevisiae* yeast cells and mammalian cells (HeLa and PC-3, derived from cervical and prostate carcinoma, respectively) to the cytotoxic action of physical or chemical agents such as ultraviolet light, methyl methanesulfonate or doxorubicin (Example 8). Another biological result of the activity of these drugs is the inhibition of the activation of transcriptional factor NF-κB by cytokines such as TNFα at pharmacologically effective concentrations (Example 7) and they enhance the cytotoxic effects of conventional antineoplastic agents. Due to these activities, the drugs object of the present invention have at least two types of medical applications:

(1) the sensitization of tumor cells to chemical or physical agents with cytotoxic activity which damage or modify DNA (genotoxic agents), which must allow reducing the therapeutically effective dose of such genotoxic agents, some of the undesirable side effects of such agents therefore being reduced.

(2) anti-inflammatory effects in pathologies presenting activation of inflammatory cytokines and chemokines.

These new drugs are furthermore tools for researching the activity of UBC13-UEV1 (UBC13-UEV2) and of other activities regulated by various forms of ubiquitylation and polyubiquitylation.

In short, these compounds further represent a new class of drugs, since there are no precedents of pharmacological inhibitors of this UBC13 enzyme, which forms a new therapeutic target, and represent an original and novel pharmacological approach with antineoplastic, anti-inflammatory applications and in other multiple pathologic processes associated to metabolic pathways involving the UBC13 enzyme and K63 type non-canonical polyubiquitylation.

Compounds of Formula (I)

A first aspect of the invention relates to a compound of formula (I):

$$R-(CR_1R_2)q\text{-}CO\text{-}N(R_3)\text{-}C(R_4R_5)\text{-}CO\text{-}NH_2 \qquad (I)$$

wherein:
R is the radical

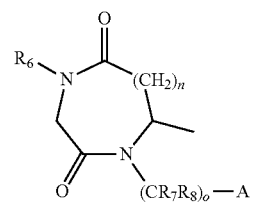

wherein:
$R_6$ is a radical selected from: H, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl;

A is a radical selected from substituted or unsubstituted aryl and substituted or unsubstituted heterocyclyl;

$R_7$ and $R_8$ are independently selected from H, methyl, ethyl, propyl and isopropyl, o is a number selected from 0, 1, 2, 3 and 4, n is a number selected from 0 and 1, the line — indicates the bonding site of the radical R with the rest of the molecule of formula (I);

$R_1$ and $R_2$ are independently selected from H, methyl, ethyl, propyl and isopropyl;

$R_3$ is a radical selected from: H, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl;

$R_4$ and $R_5$ are independently selected from H, methyl, ethyl, propyl and isopropyl;

q is a number selected from 0 and 1;

and salts, solvates, prodrugs or stereoisomers thereof.

The invention also provides salts of the compounds of the invention. For example, the pharmaceutically acceptable salts of the compounds provided herein can be acid addition salts, base addition salts or metal salts, and can be synthesized from parent compounds containing a basic or acid moiety by means of conventional chemical processes. Such salts are generally prepared, for example, by reacting the free acid or base forms of these compounds with a stoichiometric amount of the suitable base or acid in water or in an organic solvent or in a mixture of the two. Non-aqueous media such as ether, ethyl acetate, ethanol, isopropanol or acetonitrilo are generally preferred. Examples of acid addition salts include mineral acid addition salts such as, for example, hydrochloride, hydrobromide, hydroiodide, sulfate, nitrate, phosphate, organic acid addition salts such as, for example, acetate, maleate, fumarate, citrate, oxalate, succinate, tartrate, malate, mandelate, methanesulfonate and p-toluenesulfonate. Alkali addition salts include inorganic salts such as, for example, ammonium salts and organic alkaline salts such as, for example, ethylenediamine, ethanolamine, N,N-dialkylenethanolamine, triethanolamine, glutamine and basic amino acid salts. Examples of metal salts include, for example, sodium, potassium, calcium, magnesium, aluminium and lithium salts.

The term "pharmaceutically acceptable" relates to molecular entities and compositions which are physiologically tolerable and normally do not cause an allergic or similar adverse reaction, such as gastric discomfort, dizziness and the like, when they are administered to a human being. Preferably, as used herein, the term "pharmaceutically acceptable" means approved by a regulatory agency of the federal or state government or listed in the US pharmacopoeia or another generally renowned pharmacopoeia for its use in animals, and more particularly in human beings.

For the persons skilled in the art it will be evident that the scope of the present invention also includes salts which are not pharmaceutically acceptable as possible means for obtaining pharmaceutically acceptable salts.

The compounds of the invention can be in crystalline form as free compounds or as solvates and both forms are intended to be within the scope of the present invention. In this sense, the term "solvate", as used herein, includes both pharmaceutically acceptable solvates, i.e., solvates of the compound of formula (I) which can be used in the production of a medicinal product, and non-pharmaceutically acceptable solvates, which can be useful in the preparation of pharmaceutically acceptable solvates or salts. The nature of the pharmaceutically acceptable solvate is not critical provided that it is pharmaceutically acceptable. Solvates can be obtained by conventional solvation methods well known by persons skilled in the art. Examples of solvates include hydrates and alcoholates, preferably $C_1$-$C_6$ alcoholates, for example, methanolate.

The term "prodrug", as used herein, includes any derivative compound of a compound of formula (I), for example, esters, including carboxylic acid esters, amino acid esters, phosphate esters, metal salt sulfonate esters, etc., carbamates, amides, etc., which, when it is administered to an individual is capable of directly or indirectly providing said compound of formula (I) in said individual. Advantageously, said derivative is a compound increasing the bioavailability of the compound of formula (I) when it is administered to an individual or enhancing the release of the compound of formula (I) in a biological compartment. The nature of said derivative is not critical provided that it can be administered to an individual and provides the compound of formula (I) in a biological compartment of an individual. Said prodrug can be prepared by means of conventional methods known by persons skilled in the art.

It will be immediately evident for skilled persons that the present invention includes all the possible isomers of the compounds described herein. Thus, depending on the presence of multiple bonds, the compounds of the invention can include Z and E isomers. Optical isomers or enantiomers, depending on the presence of chiral centers, are also included. Individual isomers, enantiomers or diastereoisomers and the mixtures thereof are within the scope of the present invention. Individual enantiomers or diastereoisomers, as well as the mixtures thereof, can be separated by means of conventional techniques.

A stereoisomer is understood, for skilled persons, as compounds formed from the same atoms joined by the same sequence of bonds, but with different three-dimensional structures which are not interchangeable.

For their application in therapy, the compounds of formula (I), the isomers, salts, prodrugs or solvates thereof, are preferably in a pharmaceutically acceptable or substantially pure form, i.e., it has a pharmaceutically acceptable purity level excluding normal pharmaceutical additives such as diluents and carriers, and not including material considered to be toxic at normal dosage levels. The purity levels for the active ingredient are preferably greater than 50%, more preferably greater than 70%, more preferably greater than 90%. In a preferred embodiment, they are greater than 95% of the compound of formula (I), or of the salts, solvates or prodrugs thereof.

Unless otherwise indicated, the compounds of the invention also include compounds that only differ in the presence of one or more isotopically enriched atoms. For example, compounds having said structure, except for the substitution of a hydrogen with a deuterium or with tritium, or the substitution of a carbon with a carbon enriched in $^{13}C$ or $^{14}C$ or a nitrogen enriched in $^{15}N$, are within the scope of this invention.

The compounds described in the present invention, the pharmaceutically acceptable salts, prodrugs and/or solvates thereof as well as the pharmaceutical compositions containing them can be used together with other additional drugs to provide a combination therapy. Said additional drugs can form part of the same pharmaceutical composition or, alternatively, they can be provided in the form of a separate composition for the administration thereof simultaneously or not to the administration of the pharmaceutical composition comprising a compound of formula (I), or a pharmaceutically acceptable prodrug, solvate, derivative or salt thereof.

In the definitions of the compounds described herein the following terms have the indicated meaning:

"Alkyl" relates to a linear or branched chain hydrocarbon radical formed by carbon and hydrogen atoms, which does not contain unsaturations, with one to six, preferably one to four carbon atoms and which is joined to the rest of the molecule by a single bond, for example, methyl, ethyl, n-propyl, i-propyl, n-butyl, t-butyl, n-pentyl, etc.

"Alkenyl" relates to a linear or branched chain hydrocarbon radical formed by carbon and hydrogen atoms, containing at least one unsaturation, with two to six, preferably two to four carbon atoms and which is joined to the rest of the molecule by a single bond.

"Cycloalkyl" relates to a saturated carbocyclic ring having between three and six carbon atoms. Suitable cycloalkyl groups include, but are not limited to cycloalkyl groups such as cyclopropyl, cyclobutyl, cyclopentyl or cyclohexyl.

"Cycloalkylalkyl" relates to a cycloalkyl group joined to the rest of the molecule by an alkyl group such as cyclopentylethyl.

"Alkynyl" relates to a linear or branched chain hydrocarbon radical formed by carbon and hydrogen atoms, containing at least one conjugated or non-conjugated carbon-carbon triple bond, with two to six, preferably two to four carbon atoms and which is joined to the rest of the molecule by a single bond, such as —CCH, —CH₂CCH, —CCCH₃, —CH₂CCCH₃.

"Aryl" relates to an aromatic hydrocarbon radical having six carbon atoms such as phenyl.

"Arylalkyl" relates to an aryl group joined to the rest of the molecule by an alkyl group such as benzyl and phenethyl.

"Heterocyclyl" relates to a stable ring with 3 to 6 members consisting of carbon atoms and between one and four heteroatoms selected from the group consisting of nitrogen, oxygen and sulfur, preferably a ring with 4 to 6 members with one, two, three or four heteroatoms, more preferably a ring with 5 or 6 members with one, two or three heteroatoms. For the purposes of this invention, the heterocycle is a monocyclic ring system. The nitrogen, carbon or sulfur atoms in the heterocyclyl radical can optionally be oxidized; the nitrogen atom can be optionally quaternized; and the heterocyclyl radical can be partially or completely saturated or be aromatic. Examples of such heterocycles include, but are not limited to, azepines, benzimidazole, benzothiazole, furan, isothiazole, imidazole, indole, piperidine, piperazine, thiadiazole, tetrahydrofuran.

"Heterocyclylalkyl" relates to a heterocycle group joined to the rest of the molecule by an alkyl group such as pyrimidinylethyl.

Unless otherwise indicated, the radicals alkyl, cycloalkyl, cycloalkylalkyl, alkenyl, alkynyl, aryl, arylalkyl, heterocyclyl and heterocyclylalkyl can be optionally substituted with one, two or three substituents such as halo (fluorine, chlorine or bromine), alkyl, alkenyl, alkynyl, cycloalkyl, hydroxy, alkoxy, sulfoxy, O-Benzyl, O-Benzoyl, carboxy, cyano, carbonyl, acyl, alkoxycarbonyl, sulfonyl, sulfonylamino, amino, imino and nitro.

The term "alkoxycarbonyl" relates to compounds with formula —C(=O)O—, in which the C-term is joined to the molecule and the O-term is joined to a carbon atom to form an ester function. Said carbon atom can be part of an alkyl, alkenyl, cycloalkyl, alkynyl, aryl, aralkyl or heterocyclyl group.

According to a preferred embodiment of the invention, in the compounds of formula (I) $R_6$ is a radical selected from H, substituted or unsubstituted arylalkyl and substituted or unsubstituted heterocyclylalkyl, and $R_3$ is a radical selected from H, substituted or unsubstituted arylalkyl and substituted or unsubstituted heterocyclylalkyl.

According to another more preferred embodiment, $R_6$ is a radical selected from substituted or unsubstituted phenylpropyl, substituted or unsubstituted phenylethyl, substituted or unsubstituted benzyl, substituted or unsubstituted furylpropyl, substituted or unsubstituted furylethyl, substituted or unsubstituted furylmethyl, substituted or unsubstituted imidazolylpropyl, substituted or unsubstituted imidazolylethyl, substituted or unsubstituted imidazolylmethyl, substituted or unsubstituted pyridinylpropyl, substituted or unsubstituted pyridinylethyl, substituted or unsubstituted pyridinylmethyl, substituted or unsubstituted piperidinylpropyl, substituted or unsubstituted piperidinylethyl and substituted or unsubstituted piperidinylmethyl; and $R_3$ is a radical selected from substituted or unsubstituted phenylpropyl, substituted or unsubstituted phenylethyl, substituted or unsubstituted benzyl, substituted or unsubstituted furylpropyl, substituted or unsubstituted furylethyl, substituted or unsubstituted furylmethyl, substituted or unsubstituted imidazolylpropyl, substituted or unsubstituted imidazolylethyl, substituted or unsubstituted imidazolylmethyl, substituted or unsubstituted pyridinylpropyl, substituted or unsubstituted pyridinylethyl, substituted or unsubstituted pyridinylmethyl, substituted or unsubstituted piperidinylpropyl, substituted or unsubstituted piperidinylethyl, and substituted or unsubstituted piperidinylmethyl.

According to an even more preferred embodiment, $R_6$ is a radical substituted with one or more radicals selected from fluorine, chlorine, bromine, trifluoromethyl, hydroxyl, alkoxyl, alkylcarbonyl, alkylamino, sulfonamino, cyano, nitro, nitrite, nitrate, thionitrate and carboxamido.

According to another additional embodiment of the invention, $R_3$ is a radical substituted with one or more radicals selected from fluorine, chlorine, bromine, trifluoromethyl, hydroxyl, alkoxyl, alkylcarbonyl, alkylamino, sulfonamino, cyano, nitro, nitrite, nitrate, thionitrate and carboxamido and salts.

According to other different embodiments of the invention: $R_6$ is the radical p-fluorophenylethyl or 2,4-dichlorophenylethyl; substituent A is a substituted or unsubstituted aryl; substituent A is a phenyl substituted with chlorine, fluorine and/or bromine, and o is a number selected from 1, 2 and 3; $R_7$ and $R_8$ are both H, o is 2, and A is p-fluorophenyl; $R_3$ is 2-pyrimidinylethyl, 2,4-dichlorophenylethyl or 4-methoxyphenylethyl; n is 1; n is 0; q is 0; q is 1.

A preferred embodiment of the invention is formed by the compound of formula (Ia): (N-aminocarbamoylmethyl-N-(2'-(2"pyridyl)ethyl)-1,4-bis[2'-(4"-fluoro-phenyl)ethyl]-3,7-dioxo-[1,4]diazepane-5-carboxamide), called Varubin:

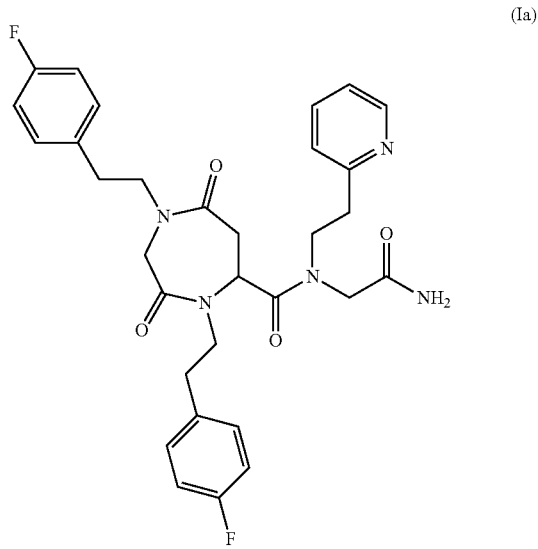 [SMILES: NC(=O)CN(CCc1ccccn1)C(=O)C1CC(=O)N(CCc2ccc(F)cc2)CC(=O)N1CCc1ccc(F)cc1]

(Ia)

and salts, solvates, prodrugs or stereoisomers thereof.

Another preferred embodiment of the invention is formed by the compound of formula (Ib): (1,4-bis[2'-(4"-fluorophenyl)ethyl]-2-[N-aminocarbonylmethyl-N-(2'-(2"-pyridyl) ethyl)-carbonylmethyl]piperazine-3,6-dione):

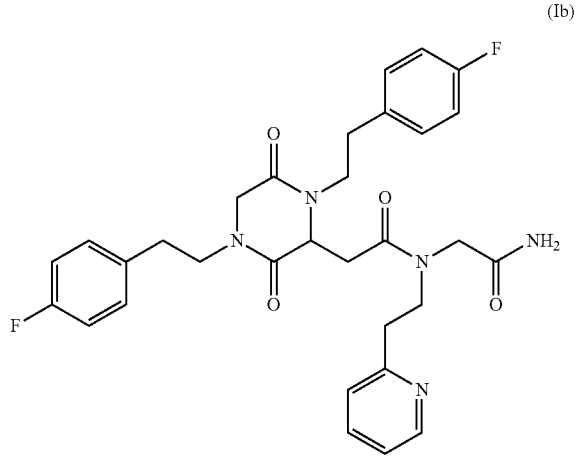 [SMILES: NC(=O)CN(CCc1ccccn1)C(=O)CC1C(=O)N(CCc2ccc(F)cc2)CC(=O)N1CCc1ccc(F)cc1]

(Ib)

and salts, solvates, prodrugs or stereoisomers thereof.

Other preferred embodiments are formed by the following compounds:

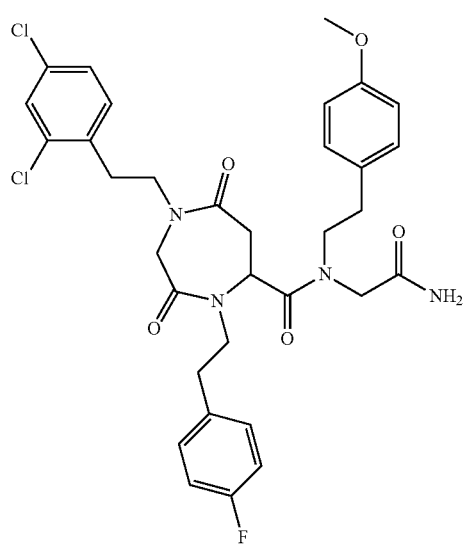

N-aminocarbamoylmethyl-N-(2'-(4"-methoxyphenyl)ethyl)-1-[2'-(2",4"-dichlorophenyl)ethyl]-4-[2'-(4"-fluorophenyl)ethyl]-3,7-dioxo-[1,4]diazepane-5-carboxamide

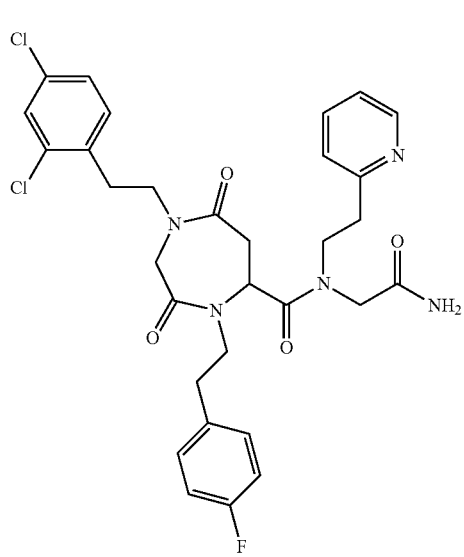

N-aminocarbamoylmethyl-N-(2'-(2"-pyridyl)ethyl)-1-[2'-(2",4"-dichlorophenyl)ethyl]-4-[2'-(4"-fluorophenyl)ethyl]-3,7-dioxo-[1,4]diazepane-5-carboxamide

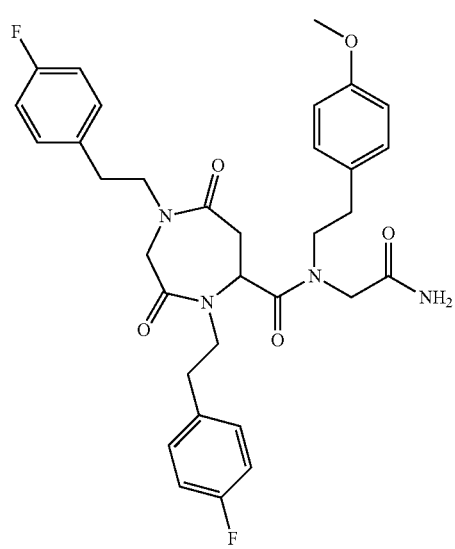

N-aminocarbamoylmethyl-N-(2'-(4"-methoxyphenyl)ethyl)-1-4-bis[2'-(4"-fluorophenyl)ethyl]-3,7-dioxo-[1,4]diazepane-5-carboxamide

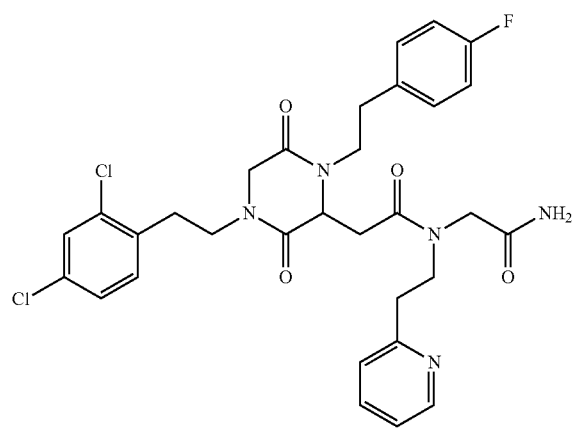

1-[2'-(2'',4''-
dichlorophenyl)ethyl]-4-[2'-(4''-
fluorophenyl)ethyl]-2-[N-
aminocarbonylmethyl-N-(2'-
(2''pyridyl)ethyl)carbonylmethyl]
piperazine-3,6-dione

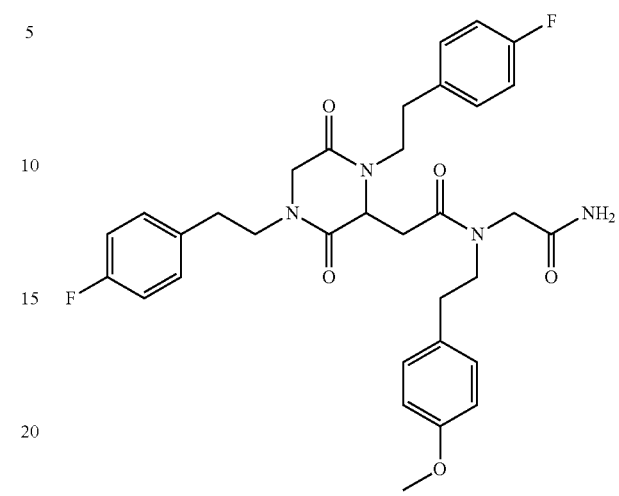

1,4-bis[2'-(4''-fluorophenyl)ethyl]-
2-[N-aminocarbonylmethyl-N-(2'-(4''-
methoxyphenyl)ethyl)carbonylmethyl]
piperazine-3,6-dione

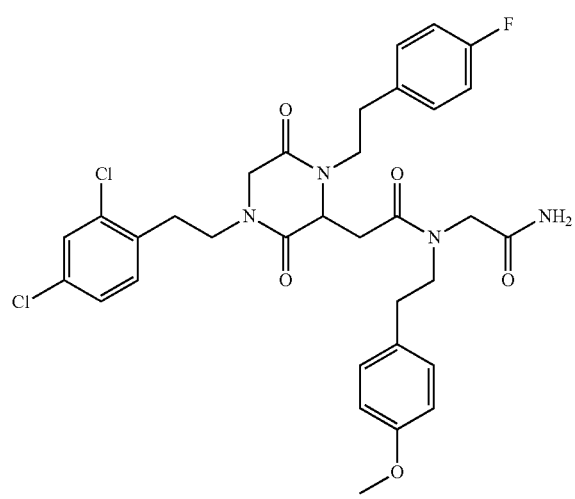

1-[2'-(2'',4''-
dichlorophenyl)ethyl]-
4-[2'-(4''-
fluorophenyl)ethyl]-2-
[N-aminocarbonylmethyl-
N-(2'-(4''-
methoxyphenyl)ethyl)
carbonylmethyl]
piperazine-3,6-dione

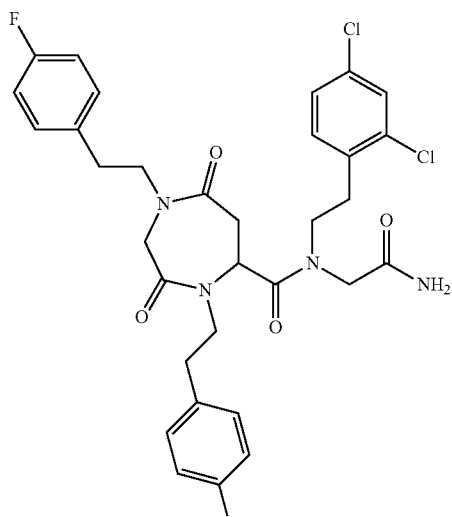

N-aminocarbamoylmethyl-
N-[2'-(2'',(4''-
dichlorophenyl)ethyl)-
1-4-bis[2'-(4''-
fluorophenyl)ethyl]-
3,7-dioxo-
[1,4]diazepane-5-
carboxamide

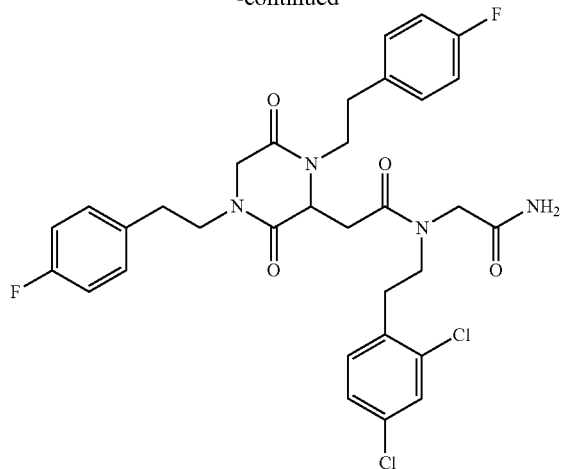

[1,4-bis[2'-(4''-fluorophenyl)ethyl]-2-[N-aminocarbonylmethyl-N-(2'-(2'',4''-dichlorophenyl)ethyl)carbonylmethyl] piperazine-3,6-dione In its second aspect, the invention relates to a process for synthesizing said compounds of formula (I), the salts, solvates, prodrugs and stereoisomers thereof. The compounds of the present invention of formula (I) can be obtained or produced by means of a chemical synthetic route or obtained from a natural material of different origin. The present application describes a synthetic route of the compounds of the invention of formula I based on a solid-phase synthesis. The schemes of the solid-phase synthesis of two of the compounds of the invention, those of formula (Ia) and (Ib), are included below. For the persons skilled in the art it will be evident to apply this type of synthesis, shown by the two schemes set forth below and by Example 3), to the remaining compounds included in formula (I).

Scheme I: Synthesis of the compound of formula Ia: (N-aminocarbamoylmethyl-N-(2'-(2''pyridyl)ethyl)-1,4-bis[2'-(4''-fluoro-phenyl)ethyl]-3,7-dioxo-[1,4-diazepane-5-carboxamide).

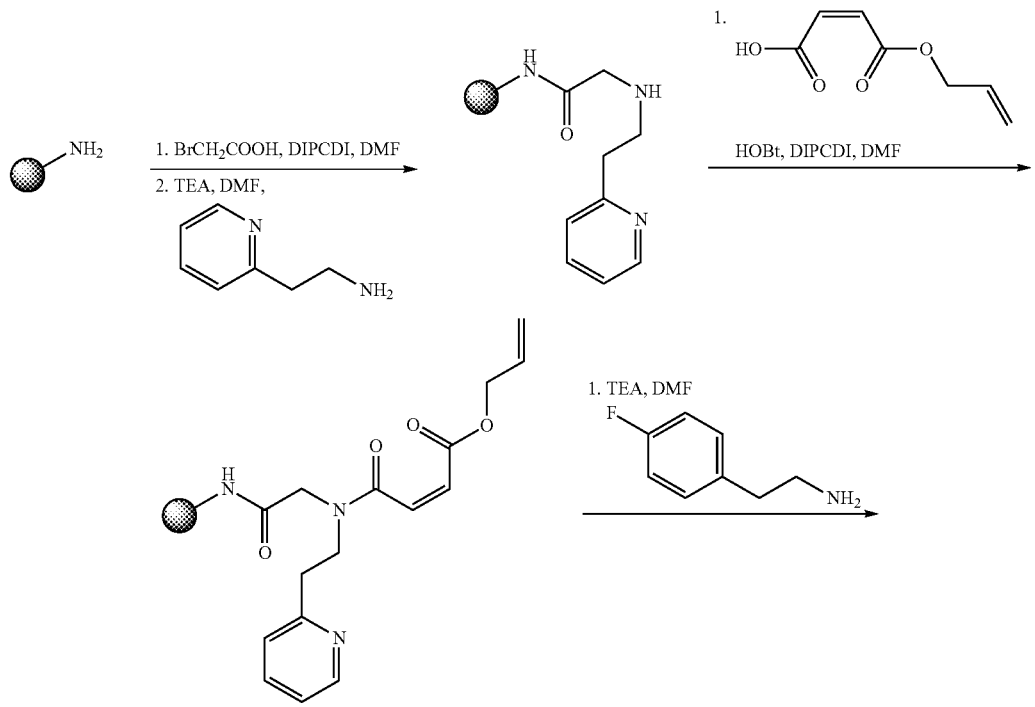

-continued
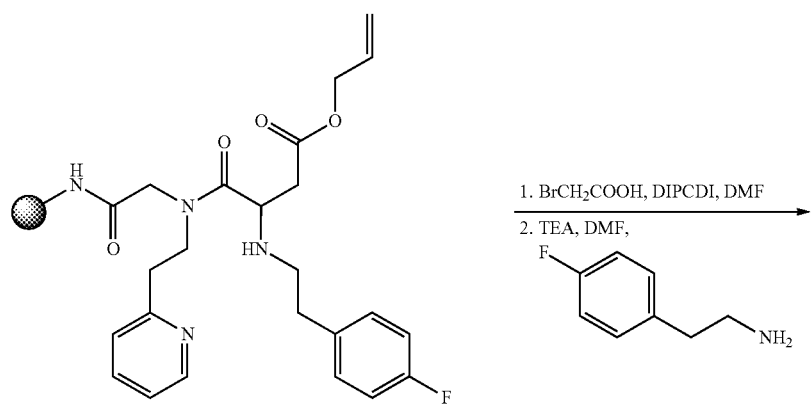
1. BrCH₂COOH, DIPCDI, DMF
2. TEA, DMF,
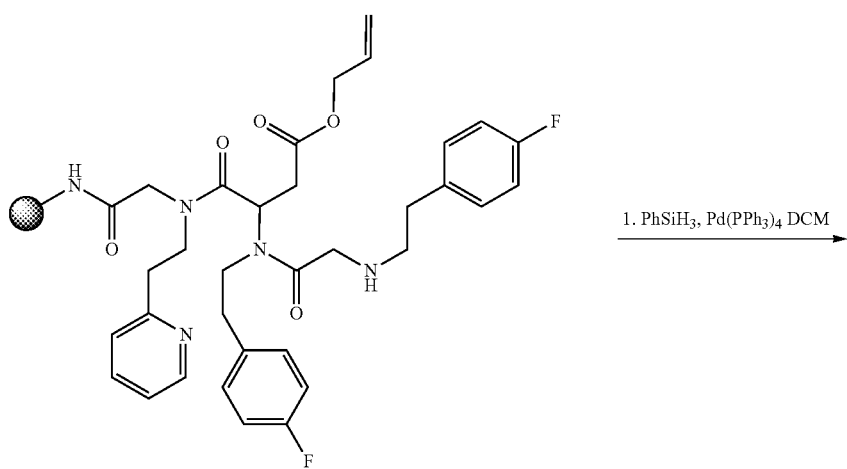
1. PhSiH₃, Pd(PPh₃)₄ DCM
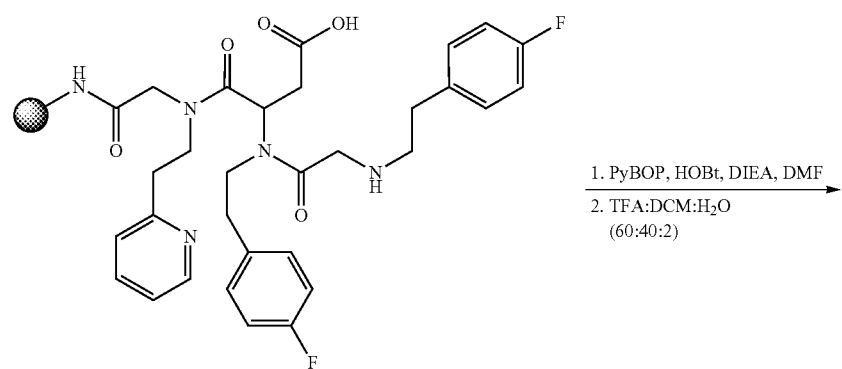
1. PyBOP, HOBt, DIEA, DMF
2. TFA:DCM:H₂O (60:40:2)

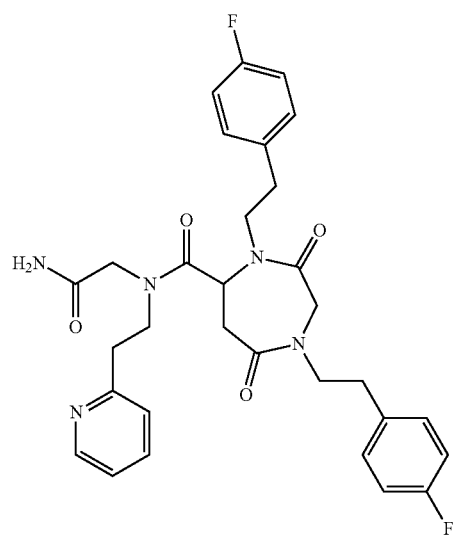
Ia
Scheme II: Synthesis of the compound of formula Ib: (1,4-bis[2'-(4''-fluorophenyl)ethyl]-2-[N-aminocarbonylmethyl-N-(2'-(2''-pyridyl)ethyl)-carbonylmethyl]piperazine-3,6-dione).
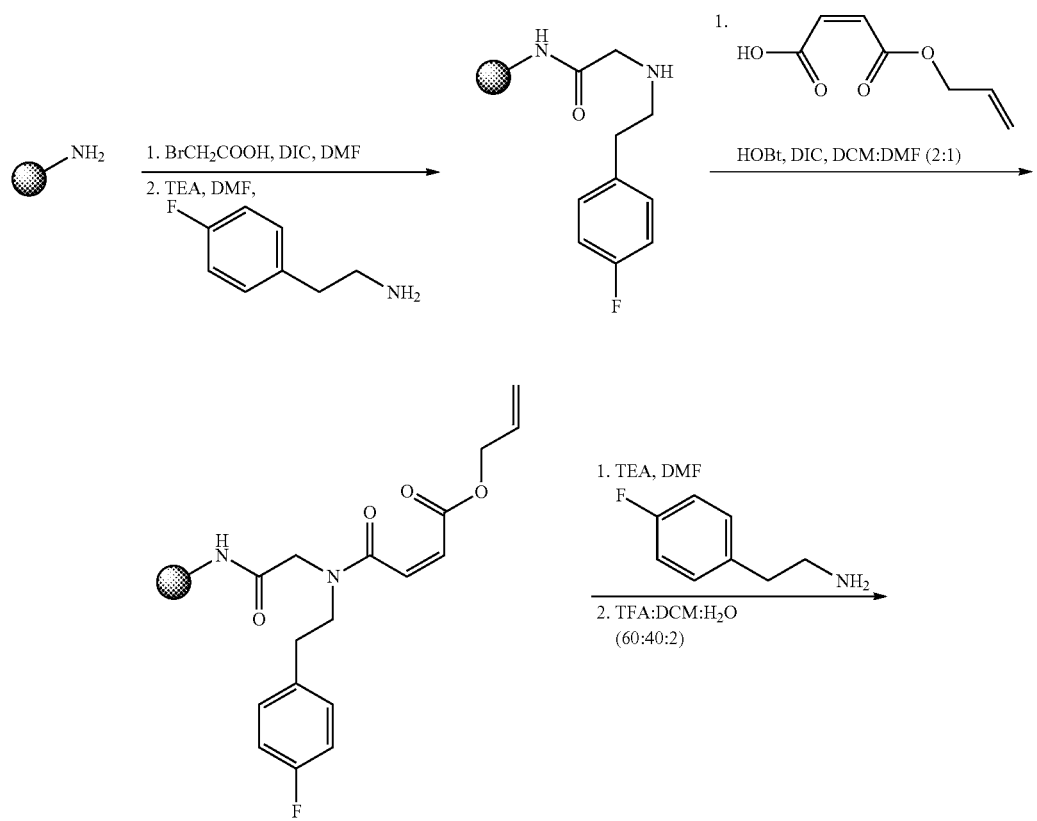

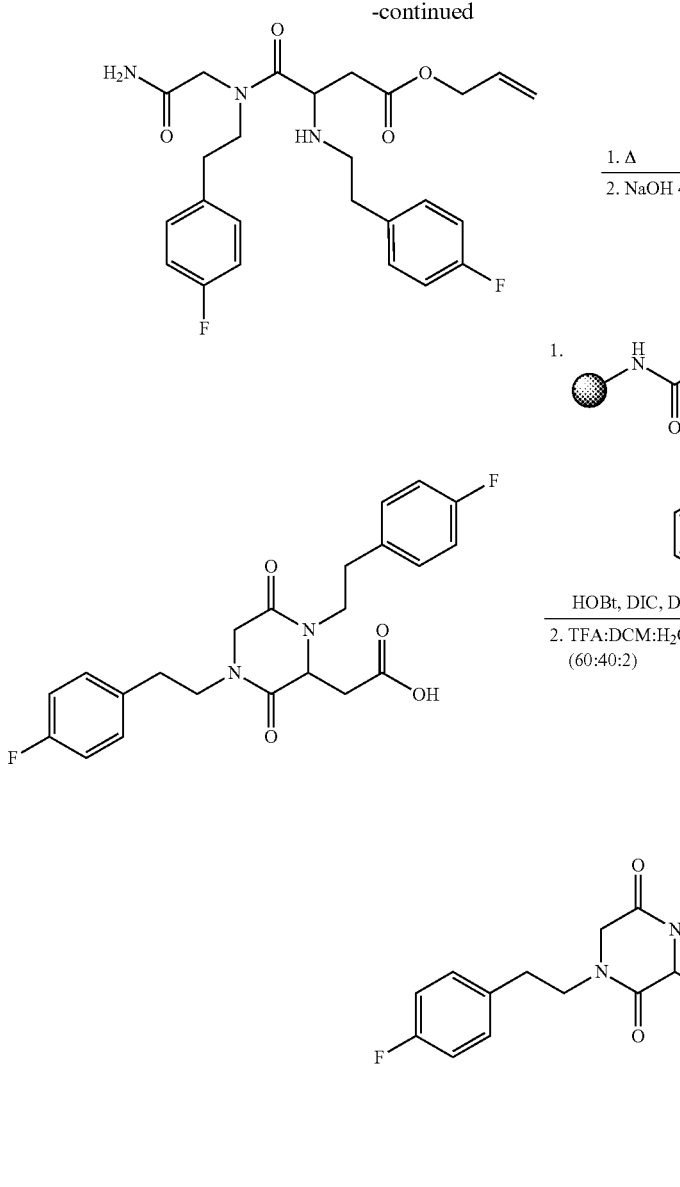

Another additional aspect of the invention is formed by a pharmaceutical composition, hereinafter pharmaceutical composition of the invention, comprising at least one compound of formula (I), or a pharmaceutically acceptable salt, prodrug, solvate or stereoisomer thereof, in a therapeutically effective amount, together with a pharmaceutically acceptable carrier, adjuvant or vehicle for the administration to a patient.

Another particular embodiment of the invention is formed by the pharmaceutical composition of the invention in which the compound of formula (I) is the following: N-aminocarbamoylmethyl-N-(2'-(2"pyridyl)ethyl)-1,4-bis[2'-(4"-fluorophenyl)ethyl]-3,7-dioxo-[1,4]diazepane-5-carboxamide (Ia) or any of the R, S enantiomeric forms and/or racemic mixtures thereof.

Another particular embodiment of the invention is formed by the pharmaceutical composition of the invention in which the compound of formula (I) is the following: 1,4-bis[2'-(4"-fluorophenyl)ethyl]-2-[N-aminocarbonylmethyl-N-(2'-(2"pyridyl)ethyl)carbonyl-methyl]piperazine-3,6-dione (Ib), or any of the R, S enantiomeric forms and/or racemic mixtures thereof.

Another particular embodiment of the invention is formed by the pharmaceutical composition of the invention in which compound (I) is selected from:

N-aminocarbamoylmethyl-N-(2'-(2"-pyridyl)ethyl)-1-[2'-(2",4"-dichlorophenyl)ethyl]-4-[2'-(4"-fluorophenyl)ethyl]-3,7-dioxo-[1,4]diazepane-5-carboxamide;

N-aminocarbamoylmethyl-N-(2'-(4"-methoxyphenyl)ethyl)-1-[2'-(2",4"-dichlorophenyl)ethyl]-4-[2'-(4"-fluorophenyl)ethyl]-3,7-dioxo-[1,4]diazepane-5-carboxamide;

N-aminocarbamoylmethyl-N-(2'-(4"-methoxyphenyl)ethyl)-1,4-bis[2'-(4"-fluorophenyl)ethyl]-3,7-dioxo-[1,4]diazepane-5-carboxamide;

1-[2'-(2",4"-dichlorophenyl)ethyl]-4-[2'-(4"-fluorophenyl)ethyl]-2-[N-aminocarbonylmethyl-N-(2'-(2"pyridyl)ethyl)carbonylmethyl]piperazine-3,6-dione;

1-[2'-(2",4"-dichlorophenyl)ethyl]-4-[2'-(4"-fluorophenyl)ethyl]-2-[N-aminocarbonylmethyl-N-(2'-(4"-methoxyphenyl)ethyl)carbonylmethyl]piperazine-3,6-dione;

1,4-bis[2'-(4"-fluorophenyl)ethyl]-2-[N-aminocarbonylmethyl-N-(2'-(4'-methoxyphenyl)ethyl)carbonylmethyl]piperazine-3,6-dione;

N-aminocarbamoylmethyl-N-[2'-(2",4"-dichlorophenyl)ethyl]-1,4-bis[2'-(4"-fluorophenyl)ethyl]-3,7-dioxo-[1,4]diazepane-5-carboxamide; and

[1,4-bis[2'-(4"-fluorophenyl)ethyl]-2-[N-aminocarbonylmethyl-N-(2'-(2",4"-dichlorophenyl)ethyl)carbonylmethyl]piperazine-3,6-dione.

The pharmaceutically acceptable adjuvants and vehicles which can be used in said compositions are the adjuvants and vehicles known by persons skilled in the art and normally used in the production of therapeutic compositions.

In the sense used in this description, the expression "therapeutically effective amount" relates to the amount of the agent or compound capable of developing inhibition of the UBC13 enzyme, calculated to cause the desired effect, and will generally be determined, among other causes, by the typical characteristics of the compounds, including the age, condition of the patient, the severity of the alteration or disorder, and on the route and frequency of administration.

In another particular embodiment, said therapeutic composition is prepared as a solid form or aqueous suspension in a pharmaceutically acceptable diluent. The therapeutic composition provided by this invention can be administered by any suitable route of administration, for which said composition will be formulation in the dosage form suitable for the chosen route of administration. In a particular embodiment, the therapeutic composition provided by this invention is administered orally, topically, rectally or parenterally (including subcutaneously, intraperitoneally, intradermally, intramuscularly, intravenously, etc.). A review of the different dosage forms for the administration of medicinal products and of the excipients necessary for obtaining them can be found, for example, in "Tratado de Farmacia Galénica", C. Faulí i Trillo, 1993, Luzán 5, S. A. Ediciones, Madrid, in "Remington's Pharmaceutical Sciences" by E. W. Martin or in other usual or similar ones of the Spanish and United States Pharmacopoeias.

An effective administered amount of a compound used in the invention will generally depend on the relative efficacy of the chosen compound, the seriousness of the treated disorder, or the age, weight or method of administration. Nevertheless, the active compounds are normally administered one or more times a day, for example 1, 2, 3, or 4 times a day, with a typical total daily dose in the range from 0.01 to 100 mg/kg/day.

The compounds used in the present invention can also be administered with other drugs to provide a combination therapy. The other drugs can form part of the same composition, or they can be administered in the form of a separate composition for the administration at the same time or at a different time.

An additional aspect of the invention relates to compounds of formula (I), the salts, solvates, prodrugs or stereoisomers thereof, or the mixtures thereof, for medical use.

Another additional aspect of the invention relates to the use of the compounds of formula (I), the salts, solvates, prodrugs and stereoisomers thereof, or the mixtures thereof, in the treatment and/or prophylaxis of pathologies or diseases associated to alterations of the metabolic pathways involving the UBC13 enzyme.

Another additional aspect of the invention relates to the use of the compounds of formula (I), the pharmaceutically acceptable salts, solvates, prodrugs or stereoisomers thereof, or the mixtures thereof, for preparing a medicinal product intended for the treatment and/or prophylaxis of pathologies or diseases associated to metabolic pathways involving the UBC13 enzyme.

In a particular embodiment, the pathologies or diseases associated to metabolic pathways involving the UBC13 enzyme are inflammatory and autoimmune diseases. In a preferred embodiment, the inflammatory and autoimmune pathologies or diseases can be: inflammatory bowel disease, inflammatory joint pathologies, atopic dermatitis and other inflammatory dermatological pathologies, neuritis, encephalitis, encephalomyelitis and inflammatory pathologies affecting the central or peripheral nervous system, myositis, vasculitis, systemic lupus erythematosus, infectious diseases presenting inflammation, host versus graft rejection reactions, conjunctivitis and inflammatory oculopathies, otitis or mucositis.

In another particular embodiment, the pathologies or diseases associated to metabolic pathways involving the UBC13 enzyme are cancer or neoplasia, including but not being limited to any type of benign or malignant neoplasia of any tissue origin, among them, but not limited to, any type of carcinoma including prostate, breast, lung, pancreatic, colorectal, gastric, esophageal, laryngeal, thyroid, hepatic, urinary bladder, renal, uterine and cervical carcinomas, any type of sarcoma including osteosarcomas, soft tissue sarcomas and angiosarcomas, any type of hematopoietic tumor including leukemias and lymphomas, any type of nervous system tumor including neuroblastomas, glioblastomas and astrocytomas, any dermatological cancer including melanoma, basal cell carcinoma and squamous cell carcinoma.

Another additional aspect of the invention relates to the use of the compounds of formula (I), the pharmaceutically acceptable salts, solvates, prodrugs or stereoisomers thereof, or the mixtures thereof, for preparing a medicinal product intended for the treatment and/or prophylaxis of pathologies or diseases associated to metabolic pathways involving transcriptional factor NF-κB. In a particular embodiment, the pathologies or diseases are inflammatory or neoplastic processes.

In another additional aspect, the invention relates to the use of the compounds of formula (I), the pharmaceutically acceptable salts, solvates, prodrugs or stereoisomers thereof, or the mixtures thereof, for producing a medicinal product intended for antitumor therapy, wherein said medicinal product is an antagonist of, or inhibits, the genotoxic damage tolerance pathway mediated by PCNA and RAD6 causing chemo- or radiosensitizing effects.

Another additional aspect of the invention relates to the use of the compounds of formula (I) in the production of a medicinal product for increasing the sensitivity of a mammal to the treatment with an antitumor agent.

In the present invention, "antitumor agent" is understood as the chemical, physical or biological compound or agent with antiproliferative, antioncogenic and/or carcinostatic properties which can be used to inhibit the growth, the proliferation and/or the development of tumors. Examples of antitumor agents which can be used in the present invention are (i) alkylating agents, such as alkyl sulfonates and ethyleneimine derivatives; (ii) antimetabolites, such as antifolates and purine analogs; (iii) natural products, such as antitumor antibiotics and mitotic inhibitors; (iv) hormones and antagonist thereof, such as androgens and corticosteroids; (v) biological agents, such as viral vectors; and (vi) physical agents such as ionizing radiations generated by different types of irradiation source (radiotherapeutic agents). A list of compounds which can be used as antitumor agents is described in patent application WO2005/112973.

In a particular embodiment of the invention, the antitumor agent is doxorubicin or etoposide.

The compound of formula (I) has to be administered to a mammal in an amount such that it is capable of sensitizing said mammal against the treatment with an antitumor agent. In the present invention, "effective sensitizing amount" is defined as the amount of compound of formula (I) which, when it is administered to an animal, preferably a mammal, more preferably a human being, is sufficient to sensitize the mammal against an antitumor agent or against any other antitumor therapy/treatment. The effective concentration in tumor tissue of the compounds of formula (I) which is necessary for causing a sensitizing effect against an antitumor agent ranges from 0.01 nanomolar to 100 micromolar, and the dose of said compounds which must be administered to the subject, by any route, must be adjusted to reach said intratumor concentrations. The term "sensitizing" a mammal includes:
  (i) increasing the efficacy of an antitumor agent or of antitumor therapy/treatment in a mammal which has not previously received any antitumor agent or antitumor treatment ("initial sensitization"), and/or
  (ii) increasing the efficacy of an antitumor agent or of an antitumor therapy/treatment in a mammal which has already received an antitumor agent or antitumor treatment and against which it may or may not have previously presented resistance.

Antitumor treatments which can be considered in the present invention are, for example, the treatment with a platinum compound, such as carboplatin or cisplatin, optionally in combination with gemcitabine or a taxane such as docetaxel or paclitaxel. More examples of antitumor treatments can be found in patent application WO2005/112973.

Cancers which can be effectively treated by means of using the compounds of formula (I) in the production of a medicinal product for increasing the sensitivity of a mammal to the treatment with an antitumor agent include mammalian cancers, especially cancer or neoplasia, including but not being limited to any type of benign or malignant neoplasia of any tissue origin, among them, but not limited to, any type of carcinoma including prostate, breast, lung, pancreatic, colorectal, gastric, esophageal, laryngeal, thyroid, hepatic, urinary bladder, renal, uterine and cervical carcinomas, any type of sarcoma including osteosarcomas, soft tissue sarcomas and angiosarcomas, any type of hematopoietic tumor including leukemias and lymphomas, any type of nervous system tumor including neuroblastomas, glioblastomas and astrocytomas, any dermatological cancer including melanoma, basal cell carcinoma and squamous cell carcinoma.

Finally, another additional aspect of the invention relates to a pharmaceutical composition characterized in that it comprises the compounds of formula (I), a pharmaceutically acceptable salt, solvate, prodrugs or stereoisomer thereof, in a therapeutically effective amount, together with a pharmaceutically acceptable carrier, adjuvant or vehicle. In a particular embodiment, said pharmaceutical composition additionally comprises, in a therapeutically effective amount, at least one second therapeutic agent which, in another still more particular embodiment of the invention, is a compound of formula (I), a pharmaceutically acceptable salt, solvate, prodrug or stereoisomer thereof.

EMBODIMENTS

Example 1

Experimental Screening to Identify Peptoids (N-Alkylglycines) Capable of Interfering with the UBC13-UEV1 Interaction The interaction between UBC13 and UEV1 is detected by means of two-hybrid assays in yeast. The protein forms of UBC13 and UEV1 used in the following examples are of *Homo sapiens*. The UBC13 protein, also referred to as UBE2N (HUGO nomenclature) has the following identifiers: NCBI-GI: 4507793, UniProt: P61088 and [EC:6.3.2.19]. The UEV1 protein, also referred to as UBE2V1 (HUGO nomenclature), has the following identifiers: NCBI-GI: 73765546 and UniProt: Q13404. In this assay, UBC13 is expressed as a fusion protein with the Gal4 DNA-binding domain (DBD-UBC13) from the plasmid pBD-UBC13, and UEV1 is expressed as a fusion protein with the Gal4 transcriptional activation domain (AD-UEV1) from the plasmid pACT2-UEV1. Both plasmids are cotransfected in the *Saccharomyces cerevisiae* strain AH109, being grown on plates with YPD medium without leucine or tryptophan, selecting only the colonies expressing tRNA synthase for these two amino acids, i.e., those containing the two co-transfected plasmids. The strain AH109 integrates in its genome two artificial loci: one locus contains recognition sequences for the Gal4 DBD bound to the GAL1 promoter in front of the gene for the histidyl-tRNA synthase; another locus contains Gal4 DBD bound to the GAL2 promoter before the ADE2 gene and the third locus contains recognition sequences for the Gal4 DBD bound to the MEL1 promoter in front of the lacZ gene for the β-galactosidase enzyme. The expression in strain AH109 of transcriptional factors containing, on one hand, a Gal4DBD domain, and on the other, a transcriptional activation domain, induces the expression of His-tRNA synthase, allowing growth in Histidine-free medium, and, at the same time, induces the expression of β-galactosidase, the enzymatic activity of which is colorimetrically detectable using suitable substrates. The expression and physical interaction of DBD-UBC13 and AD-UEV1 places on the promoters of these two loci a transcriptional factor capable of activating the promoter associated to a binding site for Gal4. Therefore, the growth in histidine-free medium of AH109 cells co-transfected with the plasmids pBD-UBC13 and pACT2-UEV1 indicates the existence of physical interaction between the UBC13 and UEV1 proteins. Furthermore, the degree of this interaction can be deduced with good approximation by means of colorimetric determinations of β-galactosidase activity, using as a substrate O-nitrophenyl-p-galactopyranoside (ONPG), the levels of this enzymatic activity being directly proportional to the intensity of the interaction between UBC13 and UEV1.

The synthesis of combinatorial mixtures and individual compounds based on trialkylglycines (peptoids) was performed as follows: an optimized chemical library of 5120 peptoids in 52 controlled mixtures by means of the positional scanning format on solid phase [35]. The library consists of 52 controlled mixtures and a total of 5120 compounds. Mixtures 1 to 20 ($O_1XX$) contained as a defined position one of the selected, commercially available 20 primary amines, whereas a group of 16 primary amines was used in the 'X' positions (mixture positions). Mixtures 21 to 36 ($XO_2X$) and 37 to 52 ($XXO_3$) contained in the defined position only the group of 16 amines [36]. In summary, the process in eight synthesis steps began with the release of the Fmoc protecting group of the Rink amide resin (0.7 mEq/g, Rapp Polymere, Tübingen, Germany). Then, an acylation step was performed with chloroacetic acid and diisopropylcarbodiimide, followed by the corresponding amination of the chloromethylated intermediate with the individual amine or the mixture of amines. Then the products were cleaved from the resin with a mixture of trifluoroacetic acid/dichloromethane/water, the solvents were evaporated, and the residues were lyophilized and redissolved in 10% dimethyl sulfoxide at a concentration of 5 mg/mL. The individual peptoids were prepared by means of independent solid-phase syntheses, applying the synthetic sequence described above. The purity and the identity of the individual N-alkylglycines was determined by means of high performance liquid chromatography, mass spectrometry and $^1$H and $^{13}$C NMR. The general structure (II) represented in the specification shows the general chemical structure of the N-alkylglycines (peptoids) making up the combinatorial chemical library used in this invention.

The process used to screen peptoids capable of inhibiting the interaction between UBC13 and UEV1 in two-hybrid assays in yeasts is described below. The complementary DNAs corresponding to UBC13 and UEV1 were generated by means of retrotranscription and PCR from the HepG2 cell line. UBC13 was sub-cloned into the vector pBD (Stratagene, La Jolla, Calif., USA), in accordance with the Gal4 DNA-binding domain, giving rise to the plasmid pBD-UBC13. UEV1 was sub-cloned into the vector pACT2 (Clontech), in accordance with the transactivation domain of Gal4, the plasmid pACT2-UEV1 being generated. The plasmids pBD-UBC13 and pACT2-UEV1 were co-transfected in the *Saccharomyces cerevisiae* strain AH109. To that end, recently prepared competent yeast cells were mixed with the DNA of the plasmids together with herring testes DNA as a carrier in a solution of polyethyleneglycol-lithium acetate (40% PEG, 100 mM lithium acetate, 10 mM Tris, 1 mM EDTA), being incubated for 30 minutes at 30° C. with stirring. Then 7% dimethyl sulfoxide was added, and the cells were subjected to thermal shock in a water bath at 42° C. for 30 seconds, immediately followed by cooling on ice. The cells were centrifuged at 1000 g and were resuspended in TE buffer (10 mM Tris-ClH, pH 7.5 mM, 1 mM EDTA) and were seeded in minimal medium plates to allow the selection of cells with expression of the HIS3, ADE2 and LacZ markers. After 3 days of growth, colonies positive for growth (and therefore, positive for UBC13-UEV1 interaction) were selected, and were grown in 5 mL of minimal medium overnight at 30° C. with stirring. Then it was changed to new growth medium containing one of the 52 mixtures of peptoids, at a concentration of 0.1 mM of mixture, being incubated overnight at 30° C. The absorbance (optical density or OD) of the cultures was determined at 695 nm, and new cultures were prepared with an initial $OD_{695}$ of 0.2 in YPD medium with the same mixture of peptoids at 0.1 mM under stirring at 30° C., the growth being allowed for 3-4 hours until reaching $OD_{695}$ 0.8. At that time the cultures were centrifuged, the cell pellets were resuspended in Z buffer (16 g/L $Na_2HPO_4$, 5.50 g/L $NaH_2PO_4$, 0.75 g/L KCl, 0.246 g/L $MgSO_4$ at pH 7.0) and were fragmented by means of freezing-thawing cycles in liquid nitrogen (1 minute)—37° C. (1 minute). 160 μL of the β-galactosidase substrate, O-nitrophenyl-galactopyranoside (ONPG, at 4 mg/mL in Z buffer) were immediately added, being incubated at 30° C. until the formation of a visible substrate (yellow color). The reaction was stopped by means of adding 0.4 mL of 1 M $Na_2CO_3$, being incubated for 30 minutes followed by centrifuging. The supernatants were transferred to cells for their spectrophotometric reading at 420 nm. 1 unit of β-galactosidase activity is herein described as the amount capable of hydrolyzing 1 μmol of ONPG into O-nitrophenol and D-galactose per minute per cell (Miller, 1972; Miller, 1992). This colorimetric assay provides a semi-quantitative measurement of the intensity of the interaction between 2 proteins in the two-hybrid process in yeasts.

Figure 2:
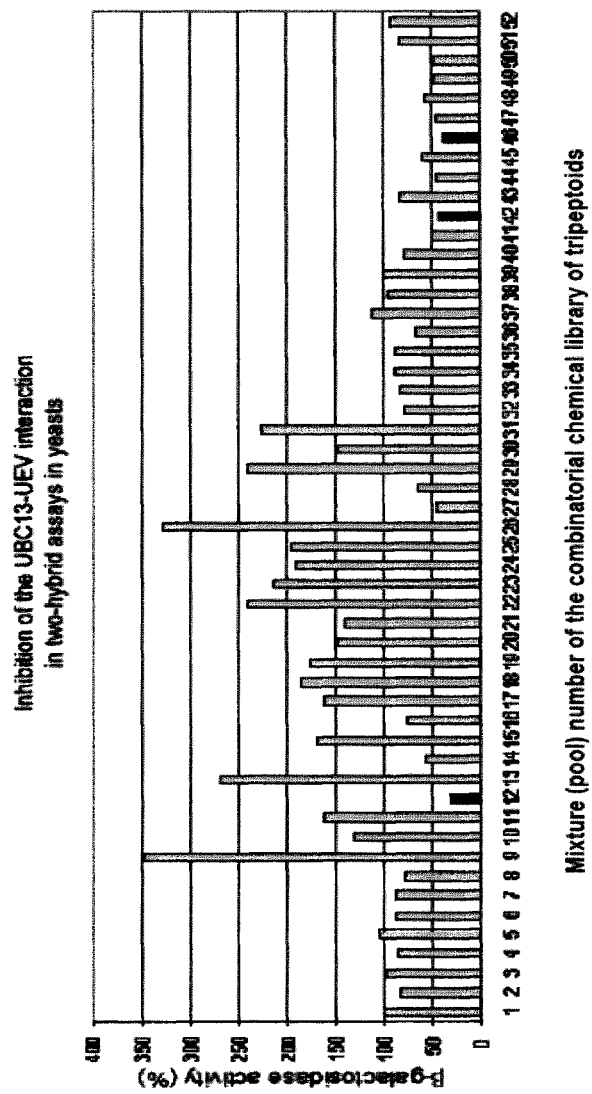
FIG. 2. Results of the screening of the 52 mixtures of peptoids in relation to their capacity to inhibit the interaction between UBC13 and UEV1, determined by two-hybrid assays in yeasts. Positive cells were incubated for the UBC13-UEV1 interaction with 5 μM of each mixture of peptoids. The interaction activities were standardized with respect to cells without peptoids, and with respect to β-galactosidase activities of the positive interaction control (large T—p53) in the presence of the same mixtures of peptoids. The solid black bars correspond to the mixtures with higher inhibitory activity for the interaction.

Each of the 52 mixtures of peptoids was analyzed by means of this process in triplicate, in three independent experiments. The interaction between UBC13 and UEV1 in the absence of peptoids and the interaction between p53 and the SV40 large T protein were used as positive interaction controls in all these assays. The laminin and p53 proteins were used as a negative control. The β-galactosidase activities for the UBC13-UEV1 interaction were standardized with respect to the β-galactosidase activities of the corresponding positive control thereof (p53-large T). The activities β-galactosidase standardized in that manner are illustrated in FIG. 2. This graph shows that the greatest inhibition of the UBC13-UEV1 interaction repetitively occurred with mixture numbers 12, 16, 37, 42 and 46. The inhibitory capacity of these mixtures on the UBC13-UEV1 interaction was confirmed by means of new colorimetric assays in triplicate, using only these 5 mixtures, confirming that the greatest inhibitory activity was in mixture numbers 12, 42 and 46.

The modular and combinatorial nature of the chemical library [35, 36] allows deducing the preferred diversity [i.e., the primary amines in positions $R^1$, $R^2$ and $R^3$ of the oligomer of structure (II)], of the peptoids responsible for this inhibitory activity. In this case, the peptoids inhibiting the UBC13-UEV1 interaction must correspond to one or more of the peptoids referred to as N37-37-9C, N37-37-13C, N15-37-9C and N15-37-13C, the chemical structures of which are shown below:

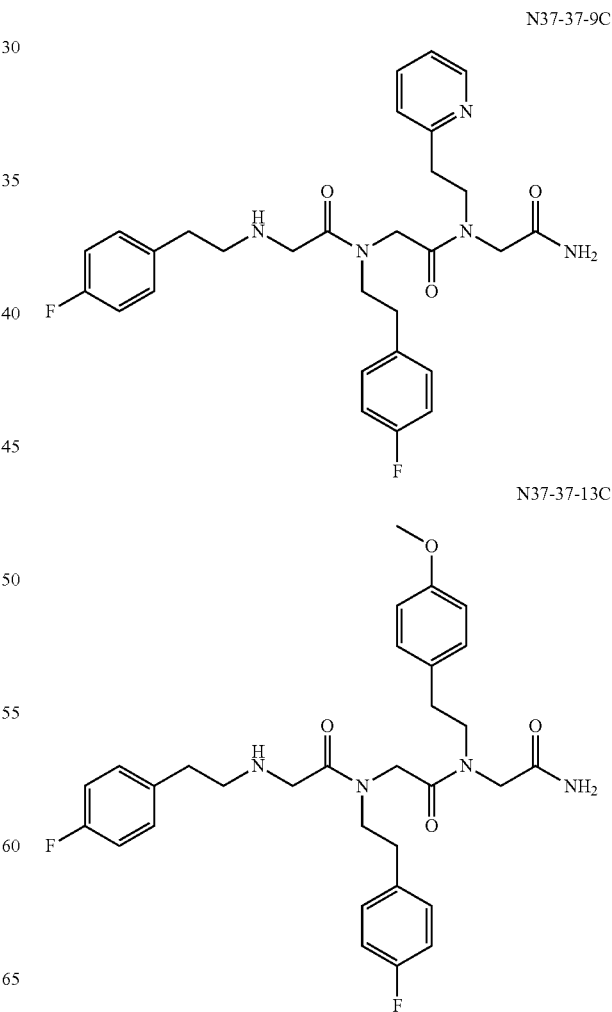

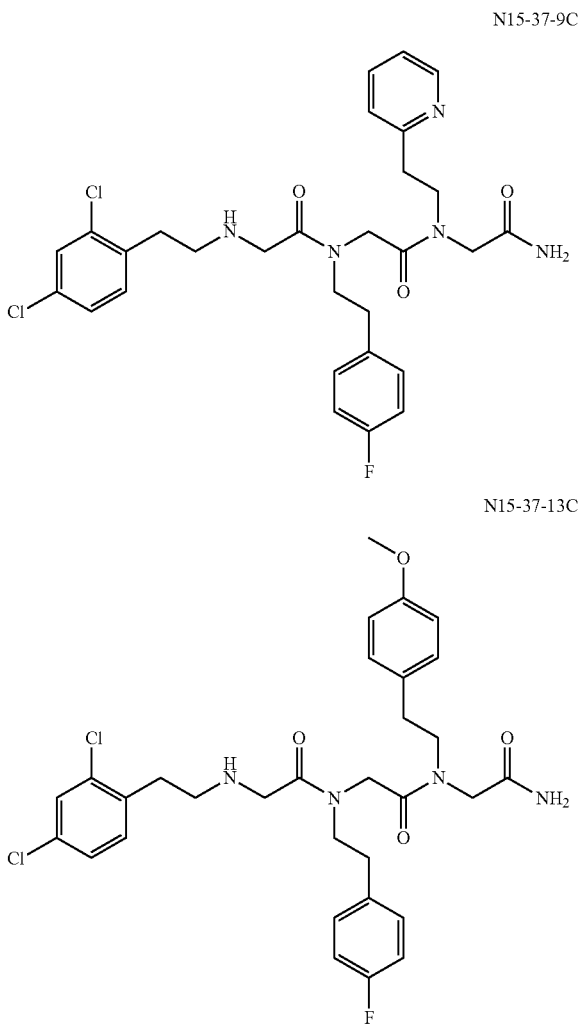

In position R¹ the amines selected are 4'-fluorophenylethyl (peptoids N37-37-9C) or 2'-4'-dichlorophenylethyl (peptoids N15-37-13C); in position R² the amine is 4'-fluorophenylethyl in all cases, and in position R³ the amines 4'-methoxyphenylethyl (peptoids N37-37-9C and N15-37-13C) and 2-(2'-pyridyl)ethyl (peptoids N37-37-9C and N15-37-9C) are selected. Therefore, the IUPAC nomenclature of the four selected peptoids is:

N37-37-9C:

[N-(2-(4'-fluorophenyl)ethyl)glycyl]-[N-(2-(4'-fluorophenyl)ethyl)glycyl]-[N-(2-(2'-pyridin)ethyl]glycinamide

N37-37-13C:

[N-(2-(4'-fluorophenyl)ethyl)glycyl]-[N-(2-(4'fluorophenyl)ethyl)glycyl]-[N-(2-(4'-methoxyphenylethyl]glycinamide

N15-37-9C:

[N-(2-(2',4'-dichlorophenyl)ethyl)glycyl]-[N-(2-(4'-fluorophenyl)ethyl)glycyl]-[N-(2-(2'-pyridin)ethyl]glycinamide

N15-37-13C:

[N-(2-(2',4'-dichlorophenyl)ethyl)glycyl]-[N-(2-(4'-fluorophenyl)ethyl)glycyl]-[N-(2-(4'-methoxyphenylethyl]glycinamide Example 2

Computational Optimization of Molecular Docking on UBC13 of Conformational Variants of Cyclic Compounds Derived from the Peptoids Selected in Example 1

It was estimated that the peptoids interfering with the UBC13-UEV1 interaction in two-hybrid assays in yeasts do so by means of the competitive binding on the surface of UBC13 which interacts with the first aliphatic helix of UEV1, therefore displacing this latter protein from the heterodimeric interaction with UBC13. The surface of UBC13 interacting with UEV1 is a 3-pointed star-shaped hydrophobic furrow with the center in a hydrophobic pocket where the phenylalanine 8 of UEV1 docks, with hydrophobic interactions with the side chains of residues E55, L56, Y57 and R70 of UBC13 [26, 27]. To study this hypothesis and as a step prior to generating medicinable compounds with this activity, studies of the virtual molecular docking on the surface of interest in UBC13 of the active peptoids, and subsequently of derivative cyclic compounds thereof were conducted. These latter compounds correspond to a chemical optimization to find the most stable conformations out of the N-alkylglycines identified. Based on this information, a family of eight structures of conformationally restricted analogs of the N-alkylglycines selected in Example 1 was designed. Each peptoid selected was configured virtually to present the structures corresponding to the eight cyclic structures, and all the forms were subjected to a molecular docking study with the model of the UBC13 protein.

These analyses were performed on the atomic structure of the UBC13-UEV1 heterodimeric complex (Brookhaven Protein Data Bank accession number 1JAT). Initially, a visual inspection and basic accessibility calculations suggested that the interaction occurring between the described residues of the interface of the complex should serve as a guideline for the development of small compounds capable of effectively preventing the formation of this binary complex.

Preparation of the UBC13 Protein (Receptor).

The initial structure of the protein corresponds to the PDB database entry 1JAT [26]. The A chain corresponding to the UBC13 protein, on which the calculations were conducted, was separated from the heterodimeric structure present in the complex. The position of the hydrogen atoms was obtained with the AMBER software package protonate utility [38]. Then the atomic radii and charges were assigned to all the atoms of the protein consistent with the parm99 version AMBER force field. Then the active center of the protein was defined. To that end, and after a first visual inspection, residues E55, L56, Y57 and R70 of the UBC13 protein located on the separating interface between the two proteins forming the dimer were identified. These residues form a pocket in which mainly residue F8 of the UEV1 protein is inserted.

Preparation of the Derivative Cyclic Compounds of the Tripeptoids Selected in Example 1 (Ligands).

The initial three-dimensional structure of these compounds (8 different structural families with a cyclic configuration for each of the tripeptoids of Example 1) was obtained from their 2D structures by means of the CORINA program [39] and an internal program (ALFA). Conformations representative of the conformational flexibility of both compounds were selected based on this analysis. Then charges and radii were assigned to each of the atoms. The parm99 version AMBER force field was used for the radii, whereas the charges were calculated by adjusting the electrostatic potential (ESP) [40] calculated with the semiempirical Hamiltonian MNDO method [41] implemented in the MOPAC software package [42].

Precalculation of the Interaction Energies.

A region of the space, or box, in which the ligands are to be accommodated was defined based on the residues previously selected in the protein. Then the interaction energy of several chemical probes, corresponding to atoms present in the ligands, was measured in a regular 0.5 Å grid built inside the predefined box. The energy function used is an adaptation of the molecular mechanics function used in the AMBER program, and is described in detail in [43].

Docking the Ligands in the Binding Site of the Receptor.

The most probable positions of the ligands within the active center were obtained by means of the "thorough" generation of all the possible orientations of each ligand in each of the points of the grid forming the active center, using a translational space of 0.5 Å and a rotational spacing of 30 degrees; the orientations were arranged depending on their lowest interaction energy, measured in the previously precalculated grid, a list of 20 orientations per analyzed ligand being selected. These calculations were performed with an internal program, CDOCK [43].

Final Selection of the Ligands.

Previously calculated corrections were made to the interaction energy for this list of ligands for the purpose of obtaining a more precise discrimination of the molecules. To that end the contribution of solvation was incorporated. Therefore, the ligand-active center binding energy is determined by the following equation:

$$\Delta G_{binding} = E_{vdW} + \Delta G_{coul} + \Delta G_{desolv}^{L} + \Delta G_{desolv}^{R} + \Delta G_{non-polar} + \Delta G_{CONF}$$

The Van der Waals interactions (first term of the second member) are from the previously described CDOCK program. The effect of the solvent was obtained by means of the numerical solution of Poisson's equation through the finite differences method such as the one implemented in the DelPhi program for the electrostatic component (components 2, 3 and 4 of the second member of the equation), and by means of a term proportional to the accessible surface for the non-electrostatic component (component 5 of the second member), using a proportionality constant of 0.00545. Cubic grids with a spacing of 0.5 Å and in which the dimensions of the grid are such that there are at least 11 Å of separation between any atom and the edges of the box were used for all the electrostatic calculations. The solute interior of the molecules was characterized with a dielectric constant of 4, whereas a dielectric constant of 80 was used for the exterior. The remaining parameters used were the program default parameters.

Figure 3:
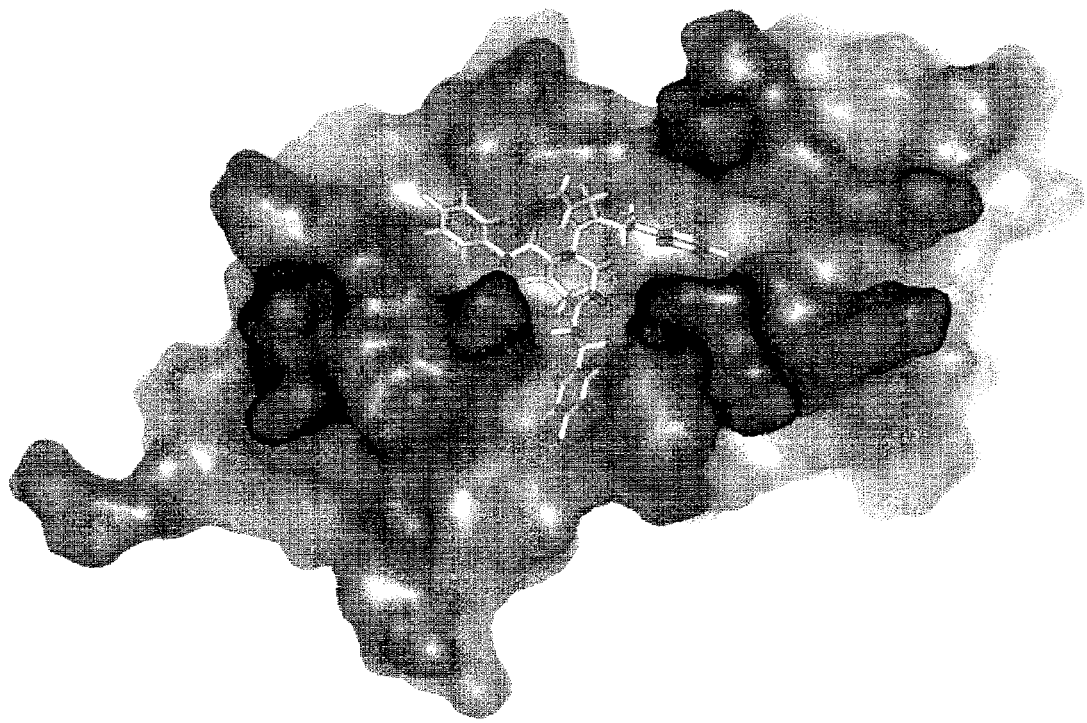
FIG. 3. Docking results. Structural models of the molecular docking of the compound Varubin or Ia on the surface of UBC13. The illustration corresponds to a Connolly representation of the surface of UBC13, next to a representation of the compound Varubin with the optimal docking by means of CDOCK on the surface of UBC13. This representation is shown at two different magnifications, in order to allow better observing the docking of the compound Varubin on the hydrophobic pocket of the surface of UBC13 normally used to interact with UEV proteins (Mms2p, UEV1 and UEV2).
Figure 3:
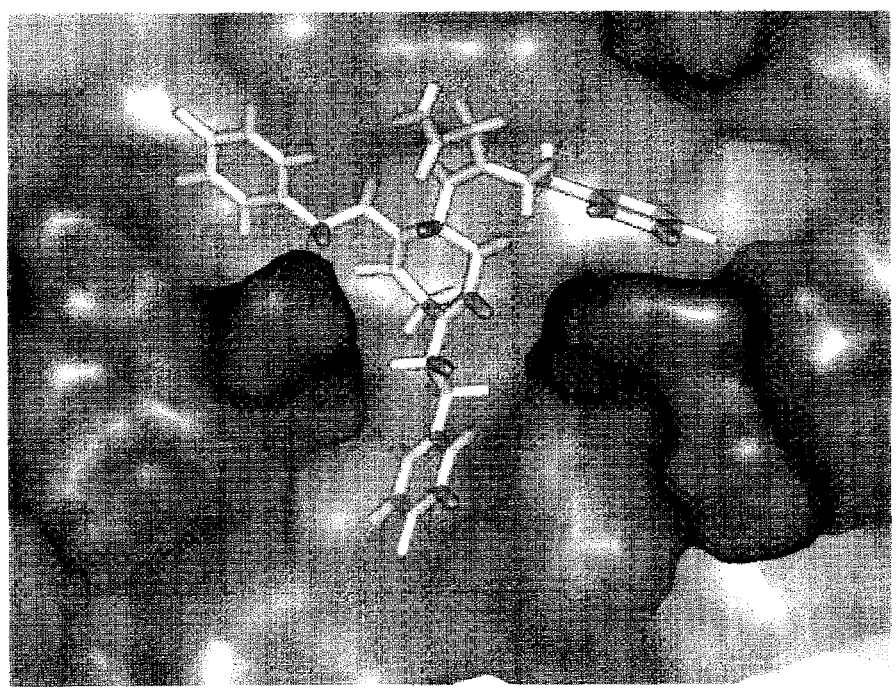
Figure 4:
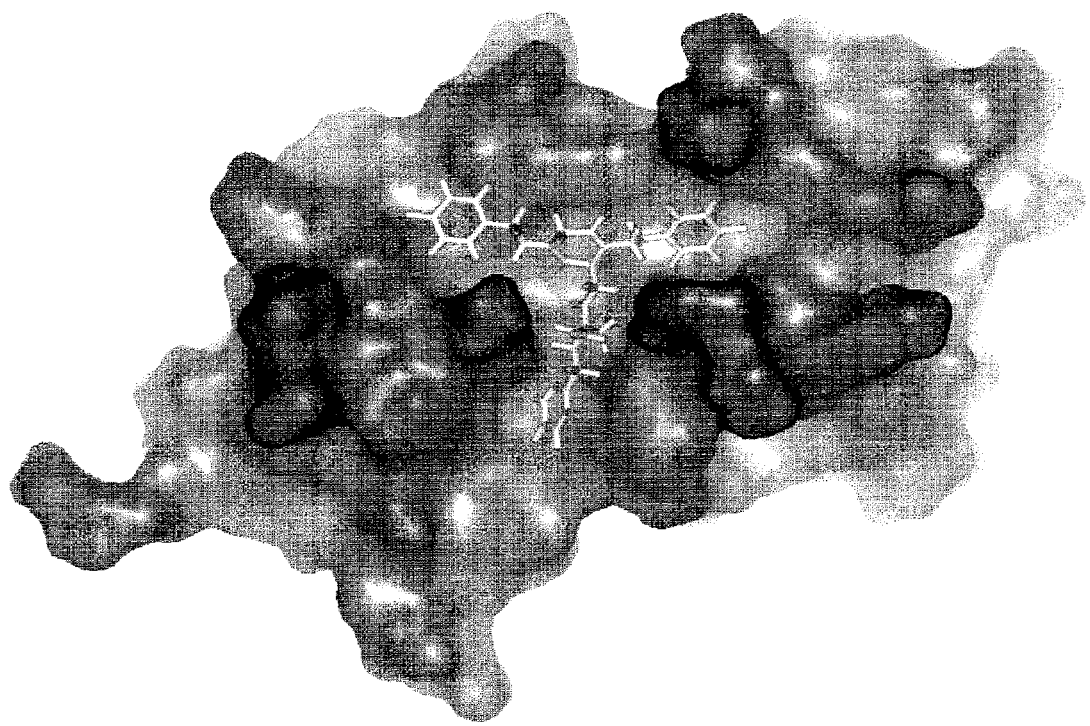
FIG. 4. Docking results. Structural models of the molecular docking of compound Ib on the surface of UBC13. The illustration corresponds to a Connolly representation of the surface of UBC13 normally used to interact with UEV1, next to a representation in bar form of the compound Ib with the optimal docking by means of CDOCK on the surface of UBC13. This representation is shown at two different magnifications, in order to allow better observing the docking of compound Ib on the hydrophobic pocket of the surface of UBC13 normally used to interact with the UEV proteins (Mms2p, UEV1 and UEV2).
Figure 4:
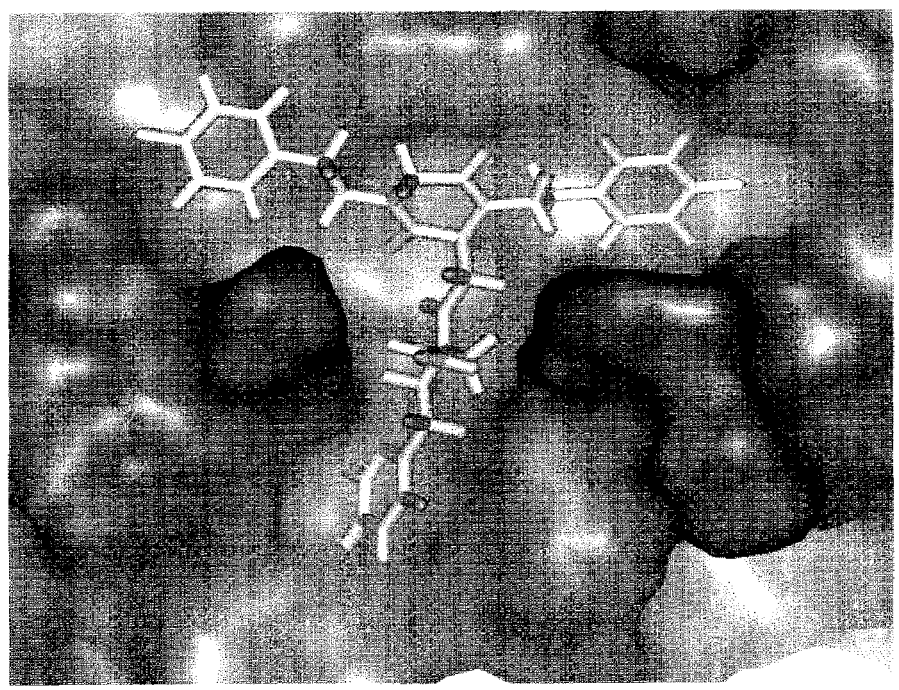

The best molecules found and their interaction energies, partitioned into contributions are comprised in Tables 1 to 6. Examples of the binding modes obtained for compounds N37-37-9C, family C (compound Ia) and N37-37-9C, family D (compound Ib) with the highest theoretical affinity are comprised in FIGS. 3 and 4.

TABLE 1

Calculations of energies for compound N37-37-9C, family C. The results for the best 20 conformations of each of the two enantiomers are shown.

| | VDW | ELEC_R | ELEC_L | COULOMB | APOLAR | TOTAL |
|---|---|---|---|---|---|---|
| Ce1_1 | −40.97 | 11.6 | 3.48 | 0.15 | −6.43 | −32.18 |
| Ce1_2 | −40.98 | 11.38 | 3 | 0.25 | −6.22 | −32.57 |

TABLE 1-continued

Calculations of energies for compound N37-37-9C, family C. The results for the best 20 conformations of each of the two enantiomers are shown.

| | VDW | ELEC_R | ELEC_L | COULOMB | APOLAR | TOTAL |
|---|---|---|---|---|---|---|
| Ce1_3 | −40.08 | 11.13 | 3.74 | 0 | −6.31 | −31.51 |
| Ce1_4 | −39.1 | 11.03 | 2.93 | 0.11 | −6.24 | −31.26 |
| Ce1_5 | −39.51 | 11.3 | 2.84 | 0.24 | −6.22 | −31.34 |
| Ce1_6 | −38.67 | 10.7 | 2.72 | −0.26 | −6.24 | −31.75 |
| Ce1_7 | −38.7 | 11.81 | 2.78 | −0.05 | −6.32 | −30.48 |
| Ce1_8 | −39.62 | 10.76 | 3.69 | −0.3 | −6.27 | −31.75 |
| Ce1_9 | −37.22 | 8.59 | 3.31 | −1.14 | −5.48 | −31.94 |
| Ce1_10 | −36.8 | 9.31 | 2.54 | −0.77 | −5.83 | −31.54 |
| Ce1_11 | −38.32 | 11.86 | 2.6 | −1.23 | −6.06 | −31.15 |
| Ce1_12 | −37.1 | 11.2 | 2.75 | −0.84 | −6.27 | −30.26 |
| Ce1_13 | −33.54 | 10.94 | 3.53 | −2.69 | −5.62 | −27.37 |
| Ce1_14 | −39.15 | 10.63 | 3.34 | 0.03 | −6.02 | −31.18 |
| Ce1_15 | −34.08 | 10.39 | 3.49 | −2.57 | −5.66 | −28.43 |
| Ce1_16 | −37.16 | 8.01 | 3.21 | −1.16 | −5.44 | −32.54 |
| Ce1_17 | −32.88 | 11.12 | 3.73 | −2.62 | −5.44 | −26.1 |
| Ce1_18 | −32.27 | 9.61 | 3.11 | −2.9 | −5.24 | −27.7 |
| Ce1_19 | −37.2 | 9 | 2.95 | −1.15 | −6.05 | −32.45 |
| Ce1_20 | −32.44 | 9.74 | 3.38 | −2.88 | −5.46 | −27.66 |
| Ce2_1 | −35.73 | 10.51 | 2.56 | −0.72 | −5.63 | −29.02 |
| Ce2_2 | −32.29 | 11.53 | 3.26 | −3.74 | −5.19 | −26.43 |
| Ce2_3 | −31.32 | 9.78 | 3.59 | −2.27 | −5.67 | −25.88 |
| Ce2_4 | −35.07 | 9.28 | 2.71 | −0.36 | −5.98 | −29.41 |
| Ce2_5 | −35.56 | 9.27 | 3.91 | −0.99 | −5.36 | −28.73 |
| Ce2_6 | −29.53 | 7.79 | 3.3 | −3.03 | −5.48 | −26.95 |
| Ce2_7 | −29.45 | 8.24 | 3.13 | −3.09 | −5.38 | −26.55 |
| Ce2_8 | −29.42 | 8.59 | 3.67 | −4.08 | −5.41 | −26.65 |
| Ce2_9 | −33.2 | 9.92 | 3.38 | −1.26 | −5.44 | −26.59 |
| Ce2_10 | −27.39 | 7.13 | 2.82 | −3.85 | −5.03 | −26.33 |
| Ce2_11 | −35.04 | 9.02 | 4.1 | −0.97 | −5.56 | −28.46 |
| Ce2_12 | −34.95 | 8.93 | 3.35 | −0.59 | −5.58 | −28.83 |
| Ce2_13 | −27.38 | 6.71 | 2.78 | −3.57 | −4.88 | −26.34 |
| Ce2_14 | −35.16 | 8.27 | 3.96 | −0.83 | −5.47 | −29.21 |
| Ce2_15 | −34.24 | 8.08 | 4.24 | −2.55 | −5.38 | −29.86 |
| Ce2_16 | −32.08 | 10.83 | 3.48 | −3.25 | −5.07 | −26.08 |
| Ce2_17 | −35.03 | 9.81 | 3.86 | 0 | −5.57 | −26.92 |
| Ce2_18 | −27.49 | 7.39 | 3.76 | −5.07 | −5.15 | −26.55 |
| Ce2_19 | −31.43 | 10.18 | 3.23 | −1.32 | −5.38 | −24.73 |
| Ce2_20 | −35.44 | 9.09 | 2.78 | 0.07 | −5.77 | −29.28 |

TABLE 2

Calculations of energies for compound N37-37-9C, family D. The results for the 20 best conformations of each of the two enantiomers are shown.

| | VDW | ELEC_R | ELEC_L | COULOMB | APOLAR | TOTAL |
|---|---|---|---|---|---|---|
| De1_1 | −41.37 | 9.62 | 2.81 | −0.35 | −6.66 | −35.95 |
| De1_2 | −34.3 | 8.84 | 3.63 | −3.13 | −5.76 | −30.72 |
| De1_3 | −33.96 | 8.71 | 3.28 | −3.38 | −5.89 | −31.25 |
| De1_4 | −33.31 | 10.2 | 3.7 | −4.26 | −6.35 | −30.02 |
| De1_5 | −33.18 | 9.22 | 3.31 | −3.81 | −5.93 | −30.38 |
| De1_6 | −33.92 | 8.73 | 3.2 | −2.73 | −5.81 | −30.53 |
| De1_7 | −36.73 | 8.24 | 3.9 | −1.68 | −5.86 | −32.13 |
| De1_8 | −39.85 | 8.28 | 2.78 | −0.59 | −6.33 | −35.72 |
| De1_9 | −32.32 | 8.4 | 3.28 | −3.09 | −5.59 | −29.33 |
| De1_10 | −34.22 | 9.98 | 3.44 | −2.68 | −5.91 | −29.39 |
| De1_11 | −33.21 | 10.09 | 3.11 | −3.27 | −5.95 | −29.23 |
| De1_12 | −31.84 | 8.01 | 3.32 | −3.6 | −5.76 | −29.86 |
| De1_13 | −32.64 | 9.91 | 3.28 | −3.3 | −5.98 | −28.73 |
| De1_14 | −33.54 | 8.94 | 3.02 | −2.52 | −5.81 | −29.91 |
| De1_15 | −31.41 | 9.95 | 3.5 | −4.36 | −6.25 | −28.57 |
| De1_16 | −32.66 | 8.65 | 3.08 | −2.97 | −5.46 | −29.35 |
| De1_17 | −32.97 | 8.57 | 3.05 | −2.68 | −5.53 | −29.55 |
| De1_18 | −35.64 | 7.83 | 3.49 | −1.69 | −5.75 | −31.76 |
| De1_19 | −31.4 | 8.93 | 3.22 | −4.34 | −6.06 | −29.65 |
| De1_20 | −32.25 | 8.24 | 3.23 | −2.92 | −5.51 | −29.21 |
| De2_1 | −42.09 | 10.69 | 3.12 | 0.72 | −6.64 | −34.21 |
| De2_2 | −38.66 | 11.23 | 3.07 | −0.35 | −6.4 | −31.1 |
| De2_3 | −37.43 | 10.48 | 2.53 | 0.26 | −6.11 | −30.28 |
| De2_4 | −35.58 | 10.02 | 2.87 | −0.76 | −6.15 | −29.6 |

TABLE 2-continued

Calculations of energies for compound N37-37-9C, family D. The results for the 20 best conformations of each of the two enantiomers are shown.

|   | VDW | ELEC_R | ELEC_L | COU-LOMB | APOLAR | TOTAL |
|---|---|---|---|---|---|---|
| De2_5 | −38.41 | 8.2 | 2.64 | 0.41 | −6.19 | −33.35 |
| De2_6 | −33.58 | 9.04 | 3.27 | −0.95 | −5.87 | −28.1 |
| De2_7 | −36.46 | 10.9 | 3.22 | −0.08 | −6.45 | −28.89 |
| De2_8 | −36.42 | 11.04 | 2.96 | −0.21 | −6.39 | −28.6 |
| De2_9 | −33.99 | 10.44 | 2.98 | −0.74 | −5.8 | −27.12 |
| De2_10 | −36.92 | 11.12 | 3.02 | 0.24 | −6.4 | −28.94 |
| De2_11 | −29.9 | 7.81 | 2.76 | −2.63 | −5.07 | −27.03 |
| De2_12 | −38.44 | 8.7 | 2.76 | 0.49 | −6.34 | −32.84 |
| De2_13 | −33.03 | 9.46 | 3.04 | −1.23 | −5.74 | −27.5 |
| De2_14 | −37.2 | 10.56 | 2.95 | −0.9 | −5.97 | −30.55 |
| De2_15 | −32.24 | 10.38 | 2.69 | −2.06 | −5.46 | −26.69 |
| De2_16 | −35.59 | 9.76 | 2.29 | 0.07 | −5.94 | −29.41 |
| De2_17 | −32.86 | 10.28 | 2.67 | −1.74 | −5.87 | −27.52 |
| De2_18 | −29.77 | 7.51 | 2.68 | −2.3 | −5.06 | −26.93 |
| De2_19 | −32.5 | 8.44 | 3.05 | −1.09 | −5.72 | −27.81 |
| De2_20 | −29.62 | 7.88 | 2.78 | −2.58 | −5.08 | −26.62 |

TABLE 3

Calculations of energies for compound N37-37-13C, family C. The results for the 20 best conformations of the two enantiomers are shown.

|   | VDW | ELEC_R | ELEC_L | COU-LOMB | APOLAR | TOTAL |
|---|---|---|---|---|---|---|
| Ce1_1 | −41.95 | 12.56 | 3.13 | −0.24 | −6.68 | −33.18 |
| Ce1_2 | −41.66 | 12.14 | 3.64 | −0.02 | −6.58 | −32.48 |
| Ce1_3 | −41.41 | 13.3 | 3.45 | 0.25 | −6.66 | −31.07 |
| Ce1_4 | −39.61 | 12.77 | 2.93 | −0.52 | −6.64 | −31.07 |
| Ce1_5 | −35.39 | 12.67 | 3.62 | −2.78 | −6.13 | −28.01 |
| Ce1_6 | −36.95 | 12.15 | 3.3 | −0.92 | −6.43 | −28.85 |
| Ce1_7 | −38.58 | 10.45 | 2.89 | −0.77 | −6.4 | −32.41 |
| Ce1_8 | −39.5 | 12.03 | 3.62 | 0.14 | −6.63 | −30.34 |
| Ce1_9 | −33.66 | 10.58 | 3.48 | −2.56 | −5.58 | −27.74 |
| Ce1_10 | −37.71 | 11.62 | 2.66 | 0.08 | −6.4 | −29.74 |
| Ce1_11 | −36.01 | 11.3 | 4.58 | −1.98 | −5.89 | −28 |
| Ce1_12 | −33.26 | 10.05 | 3.42 | −2.65 | −5.57 | −28.01 |
| Ce1_13 | −32.01 | 10.41 | 3.43 | −3.29 | −5.47 | −26.92 |
| Ce1_14 | −32.88 | 11.03 | 3.99 | −2.25 | −5.74 | −27.85 |
| Ce1_15 | −37.7 | 12.66 | 3.62 | −0.67 | −6.38 | −28.48 |
| Ce1_16 | −35.48 | 9.93 | 3.37 | −2.09 | −5.88 | −30.16 |
| Ce1_17 | −38.68 | 8.73 | 3.53 | 0.24 | −6.01 | −32.19 |
| Ce1_18 | −38.8 | 11.07 | 3.72 | 0.81 | −5.76 | −28.96 |
| Ce1_19 | −34.96 | 10.53 | 3.28 | −2.39 | −5.88 | −29.43 |
| Ce1_20 | −32.6 | 9.93 | 3.36 | −2.62 | −5.3 | −27.23 |
| Ce2_1 | −31.24 | 8.39 | 4.19 | −5.05 | −5.57 | −29.28 |
| Ce2_2 | −30.38 | 9.92 | 3.93 | −5.22 | −5.05 | −26.8 |
| Ce2_3 | −30.43 | 10.58 | 4.04 | −5.38 | −5.07 | −26.26 |
| Ce2_4 | −33.2 | 11.65 | 3.65 | −4.16 | −5.25 | −27.31 |
| Ce2_5 | −31.67 | 9.66 | 3.43 | −2.34 | −5.7 | −26.61 |
| Ce2_6 | −36.76 | 9.4 | 2.75 | 0.06 | −6.12 | −30.66 |
| Ce2_7 | −36.08 | 9.29 | 4.39 | −1.97 | −5.78 | −30.15 |
| Ce2_8 | −30.89 | 12.01 | 3.31 | −4.24 | −5.17 | −24.97 |
| Ce2_9 | −29.94 | 10.48 | 3.99 | −4.95 | −5.05 | −25.47 |
| Ce2_10 | −30.75 | 8.81 | 3.62 | −3.38 | −5.62 | −27.32 |
| Ce2_11 | −30.09 | 8.26 | 2.96 | −3.01 | −5.52 | −27.4 |
| Ce2_12 | −28.5 | 6.85 | 3.23 | −3.6 | −5.03 | −27.05 |
| Ce2_13 | −28.27 | 6.83 | 3.2 | −3.63 | −5.08 | −26.96 |
| Ce2_14 | −31.54 | 9.02 | 2.97 | −1.79 | −5.16 | −26.5 |
| Ce2_15 | −33.54 | 9.52 | 3.23 | −1.15 | −5.62 | −27.56 |
| Ce2_16 | −34.83 | 8.64 | 3.32 | −0.01 | −5.56 | −28.45 |
| Ce2_17 | −35.47 | 10.23 | 4.33 | −0.37 | −5.78 | −27.07 |
| Ce2_18 | −27.24 | 8.4 | 3.57 | −4.07 | −4.98 | −24.32 |
| Ce2_19 | −27.11 | 8.57 | 3.59 | −4.86 | −4.86 | −24.66 |
| Ce2_20 | −31.42 | 10.43 | 3.2 | −1.08 | −5.54 | −24.41 |

TABLE 4

Calculations of energies for compound N37-37-13C, family D. The results for the 20 best conformations of each of the two enantiomers are shown.

|   | VDW | ELEC_R | ELEC_L | COU-LOMB | APOLAR | TOTAL |
|---|---|---|---|---|---|---|
| De1_1 | −39.45 | 12.94 | 3.61 | 0.39 | −6.35 | −28.86 |
| De1_2 | −31.46 | 9.74 | 3.47 | −0.84 | −5.54 | −24.63 |
| De1_3 | −28.2 | 8.93 | 4.04 | −8.78 | −5.04 | −29.05 |
| De1_4 | −31.74 | 10.73 | 3 | −3.96 | −5.52 | −27.49 |
| De1_5 | −35.25 | 9.74 | 3.04 | −1.95 | −6.21 | −30.64 |
| De1_6 | −38.48 | 11.72 | 3.55 | 2.99 | −6.17 | −26.4 |
| De1_7 | −35.91 | 7.91 | 1.94 | −0.97 | −5.84 | −32.87 |
| De1_8 | −35.21 | 8.89 | 4.32 | −3.63 | −5.74 | −31.37 |
| De1_9 | −29.2 | 8.87 | 3.28 | −7.21 | −5.12 | −29.37 |
| De1_10 | −29.97 | 8.71 | 2.77 | −1.68 | −5.15 | −25.32 |
| De1_11 | −34.61 | 11.05 | 2.78 | −0.53 | −6.04 | −27.35 |
| De1_12 | −33.64 | 9.4 | 2.79 | −1.56 | −5.91 | −28.92 |
| De1_13 | −31.17 | 8.04 | 2.09 | −4.61 | −5.65 | −31.3 |
| De1_14 | −34.66 | 8.8 | 4.23 | −4.79 | −5.69 | −32.11 |
| De1_15 | −27.96 | 9.86 | 3.75 | −8.85 | −5.43 | −28.64 |
| De1_16 | −35.92 | 11.23 | 3.22 | 1.08 | −6.23 | −26.61 |
| De1_17 | −33.37 | 10.11 | 2.68 | −0.97 | −6.1 | −27.66 |
| De1_18 | −27.59 | 7.96 | 4.31 | −4.16 | −4.76 | −24.25 |
| De1_19 | −31.31 | 11.26 | 2.46 | −5.96 | −5.79 | −29.33 |
| De1_20 | −31.5 | 9.95 | 2.79 | −2.73 | −5.5 | −26.99 |
| De2_1 | −35.82 | 10.14 | 3.32 | −2.99 | −5.72 | −31.06 |
| De2_2 | −36.01 | 10.46 | 3.38 | −3.63 | −5.73 | −31.53 |
| De2_3 | −36.46 | 11.73 | 3 | −2.58 | −5.94 | −30.25 |
| De2_4 | −33.72 | 9.83 | 3.14 | −2.68 | −5.56 | −28.99 |
| De2_5 | −36.29 | 9.13 | 3.65 | −0.69 | −5.95 | −30.16 |
| De2_6 | −36.75 | 10.37 | 3.73 | −0.23 | −5.83 | −28.72 |
| De2_7 | −35.63 | 11.09 | 3.08 | −2.55 | −5.78 | −29.79 |
| De2_8 | −34.93 | 8.88 | 3.85 | −0.71 | −5.83 | −28.74 |
| De2_9 | −35.49 | 10.78 | 2.26 | −0.55 | −6 | −29 |
| De2_10 | −33.78 | 10.05 | 3.86 | −1.21 | −5.67 | −26.75 |
| De2_11 | −34.71 | 11.81 | 3.17 | −3.51 | −5.95 | −29.19 |
| De2_12 | −32.78 | 9.27 | 3.12 | −1.14 | −5.85 | −27.38 |
| De2_13 | −32.4 | 8.2 | 3.12 | −3.11 | −5.51 | −29.7 |
| De2_14 | −33.29 | 8.08 | 2.82 | −1.72 | −5.58 | −29.68 |
| De2_15 | −34.31 | 9.63 | 3.16 | −2.98 | −5.68 | −30.17 |
| De2_16 | −33.11 | 10.39 | 1.89 | −2.29 | −5.47 | −28.59 |
| De2_17 | −30.32 | 10.9 | 2.56 | −6.61 | −5.63 | −29.1 |
| De2_18 | −31.11 | 8.34 | 2.91 | −1.68 | −5.47 | −27.0 |
| De2_19 | −34.16 | 7.98 | 2.75 | −2.48 | −5.79 | −31.69 |
| De2_20 | −35.93 | 10.73 | 2.98 | −1.54 | −5.91 | −29.68 |

TABLE 5

Calculations of energies for compound N15-37-9C, family C. The results for the 20 best conformations for each of the two enantiomers are shown.

|   | VDW | ELEC_R | ELEC_L | COU-LOMB | APOLAR | TOTAL |
|---|---|---|---|---|---|---|
| Ce1_1 | −31.42 | 8.05 | 4.08 | −4.95 | −5.54 | −29.78 |
| Ce1_2 | −31.11 | 7.82 | 3.48 | −3.81 | −5.39 | −29 |
| Ce1_3 | −30.13 | 7.91 | 3.31 | −3.85 | −5.44 | −28.19 |
| Ce1_4 | −38.79 | 10.59 | 3.82 | −0.65 | −5.85 | −30.88 |
| Ce1_5 | −37.94 | 10.38 | 3.47 | −0.46 | −5.78 | −30.32 |
| Ce1_6 | −37.34 | 10.67 | 3.56 | −0.34 | −5.79 | −29.24 |
| Ce1_7 | −38.21 | 10.8 | 3.63 | −0.08 | −5.76 | −29.61 |
| Ce1_8 | −36.86 | 10.32 | 3.45 | −0.53 | −5.75 | −29.36 |
| Ce1_9 | −36.25 | 10.83 | 3.61 | −0.47 | −5.67 | −27.96 |
| Ce1_10 | −34.88 | 9.03 | 3.54 | −1.2 | −5.41 | −28.92 |
| Ce1_11 | −35.8 | 10.03 | 3.82 | −0.88 | −5.35 | −28.18 |
| Ce1_12 | −34.5 | 9.59 | 2.78 | −0.3 | −6.38 | −28.81 |
| Ce1_13 | −35.59 | 9.96 | 3.49 | −1.06 | −5.51 | −28.71 |
| Ce1_14 | −33.22 | 9.38 | 3.61 | −1.48 | −5.26 | −26.97 |
| Ce1_15 | −37.01 | 10.62 | 3.23 | −0.15 | −5.82 | −29.12 |
| Ce1_16 | −26.4 | 8.54 | 3.36 | −5.13 | −5.36 | −24.98 |
| Ce1_17 | −35.9 | 10.07 | 3.62 | −0.68 | −5.58 | −28.47 |
| Ce1_18 | −36.01 | 10.43 | 3.42 | −0.34 | −5.63 | −28.13 |
| Ce1_19 | −34.5 | 7.8 | 2.38 | −0.4 | −6.05 | −30.78 |
| Ce1_20 | −36.53 | 10.47 | 3.42 | −0.6 | −5.69 | −28.93 |
| Ce2_1 | −40.01 | 11.13 | 3.29 | −0.74 | −6.28 | −32.6 |
| Ce2_2 | −39.34 | 12.72 | 3.74 | −0.6 | −6.44 | −29.93 |

TABLE 5-continued

Calculations of energies for compound N15-37-9C, family C. The results for the 20 best conformations for each of the two enantiomers are shown.

| | VDW | ELEC_R | ELEC_L | COU-LOMB | APOLAR | TOTAL |
|---|---|---|---|---|---|---|
| Ce2_3 | −38.76 | 11.42 | 3.12 | −0.52 | −6.07 | −30.3 |
| Ce2_4 | −31 | 8.07 | 3.41 | −3.25 | −5.52 | −28.3 |
| Ce2_5 | −33.15 | 9.04 | 3.4 | −2.22 | −5.73 | −28.65 |
| Ce2_6 | −33.64 | 10.08 | 3.85 | −2.01 | −5.9 | −27.62 |
| Ce2_7 | −34.55 | 9.97 | 3.63 | −1.99 | −5.88 | −28.82 |
| Ce2_8 | −38.48 | 10.68 | 3.14 | −0.78 | −6.14 | −31.58 |
| Ce2_9 | −32.78 | 10.17 | 4.19 | −3.07 | −5.84 | −27.34 |
| Ce2_10 | −32.21 | 9.35 | 3.28 | −3.06 | −5.57 | −28.21 |
| Ce2_11 | −30.89 | 8.89 | 3.54 | −2.59 | −5.44 | −26.49 |
| Ce2_12 | −30.53 | 9.26 | 3.31 | −3.37 | −5.26 | −26.59 |
| Ce2_13 | −39.07 | 8.69 | 3.82 | −0.45 | −5.82 | −32.83 |
| Ce2_14 | −34.08 | 8.8 | 3.51 | −2.56 | −5.81 | −30.13 |
| Ce2_15 | −29.76 | 7.84 | 3.54 | −3.48 | −5.5 | −27.36 |
| Ce2_16 | −36.76 | 10.33 | 3.18 | −1.11 | −6.19 | −30.55 |
| Ce2_17 | −30.98 | 10.41 | 3.48 | −3.58 | −5.29 | −25.97 |
| Ce2_18 | −29.82 | 7.68 | 3.21 | −3.43 | −5.28 | −27.64 |
| Ce2_19 | −30.41 | 7.91 | 3.47 | −3.14 | −5.26 | −27.43 |
| Ce2_20 | −29.05 | 7.57 | 3.1 | −3.54 | −5.19 | −27.11 |

TABLE 6

Calculations of energies for compound N15-37-9C, family D. The results for the 20 best conformations for each of the two enantiomers are shown.

| | VDW | ELEC_R | ELEC_L | COU-LOMB | APOLAR | TOTAL |
|---|---|---|---|---|---|---|
| De1_1 | −34.68 | 9.24 | 2.9 | −3.31 | −6.09 | −31.94 |
| De1_2 | −32.55 | 9.33 | 2.71 | −3.49 | −5.92 | −29.93 |
| De1_3 | −31.8 | 9.65 | 2.94 | −3.91 | −5.99 | −29.11 |
| De1_4 | −31.82 | 9.87 | 2.99 | −3.5 | −6.02 | −28.48 |
| De1_5 | −32.24 | 9.17 | 2.96 | −3.09 | −5.85 | −29.04 |
| De1_6 | −30.55 | 8.58 | 2.91 | −3.59 | −5.96 | −28.61 |
| De1_7 | −32.45 | 9.35 | 2.89 | −2.7 | −5.95 | −28.85 |
| De1_8 | −30.82 | 8.8 | 2.85 | −3.29 | −5.8 | −28.25 |
| De1_9 | −34.65 | 11.15 | 3.33 | −1.78 | −5.85 | −27.8 |
| De1_10 | −33.07 | 9.56 | 2.78 | −1.95 | −6.17 | −28.85 |
| De1_11 | −34.8 | 10.71 | 2.32 | −2.65 | −6.03 | −30.45 |
| De1_12 | −37.51 | 11.5 | 3.34 | −0.18 | −6.55 | −29.03 |
| De1_13 | −34.19 | 10.84 | 2.6 | −2.88 | −6 | −29.61 |
| De1_14 | −36.24 | 10.97 | 2.31 | −0.24 | −6.08 | −29.28 |
| De1_15 | −29.39 | 9.1 | 3.01 | −3.97 | −6.08 | −27.33 |
| De1_16 | −32.13 | 8.83 | 2.66 | −2.11 | −5.87 | −28.63 |
| De1_17 | −30.16 | 9.61 | 2.58 | −3.09 | −5.52 | −26.58 |
| De1_18 | −29.86 | 8.87 | 2.63 | −3.15 | −5.75 | −27.26 |
| De1_19 | −37.1 | 8.52 | 2.3 | −0.38 | −6.37 | −33.03 |
| De1_20 | −30.85 | 8.89 | 2.8 | −2.71 | −5.86 | −27.74 |
| De2_1 | −39.67 | 10.87 | 2.76 | 0.29 | −6.35 | −32.11 |
| De2_2 | −38.76 | 10.86 | 2.94 | −0.45 | −6.5 | −31.9 |
| De2_3 | −32.13 | 9.2 | 3.03 | −2.01 | −5.88 | −27.79 |
| De2_4 | −35.8 | 9.4 | 3.29 | −0.48 | −6.26 | −29.84 |
| De2_5 | −34.36 | 9.53 | 3.15 | −1.33 | −5.97 | −28.98 |
| De2_6 | −32.14 | 9.5 | 2.31 | −1.64 | −5.64 | −27.61 |
| De2_7 | −31.83 | 9.52 | 2.49 | −1.91 | −5.63 | −27.36 |
| De2_8 | −34.02 | 10.09 | 3.04 | −1.27 | −6.06 | −28.21 |
| De2_9 | −34.52 | 10.66 | 2.82 | −0.98 | −5.85 | −27.87 |
| De2_10 | −30.44 | 9.09 | 2.28 | −2.01 | −5.65 | 26.74 |
| De2_11 | −37.62 | 8.62 | 2.66 | 0.27 | −6.32 | −32.39 |
| De2_12 | −38.49 | 8.4 | 2.69 | 0.28 | −6.37 | −33.49 |
| De2_13 | −37.27 | 10.44 | 2.87 | 0.09 | −6.48 | −30.34 |
| De2_14 | −37.5 | 10.01 | 3.53 | 0.35 | −6.29 | −29.92 |
| De2_15 | −31.9 | 9.62 | 2.36 | −1.53 | −5.6 | −27.05 |
| De2_16 | −33.12 | 10.04 | 3.38 | −1.01 | −5.49 | −26.2 |
| De2_17 | −33.26 | 9.26 | 2.98 | −0.64 | −5.72 | −27.39 |
| De2_18 | −35.45 | 10.42 | 2.26 | −0.05 | −6.2 | −29.02 |
| De2_19 | −31.57 | 10.18 | 2.24 | −1.36 | −5.73 | −26.24 |
| De2_20 | −31.96 | 7.6 | 2.37 | −1.48 | −5.42 | −28.88 |

Example 3

Synthesis of the Cyclic Compounds with Better Theoretical Docking on the Surface of UBC13 Interacting with UEV1. Compounds Ia and Ib 3.1.—Compound Ia (Varubin): N-aminocarbamoyl-methyl-N-(2'-(2"pyridyl)ethyl)-1,4-bis[2'-(4"-fluoro-phenyl)ethyl]-3,7-dioxo-[1,4]diazepane-5-carboxa-mide

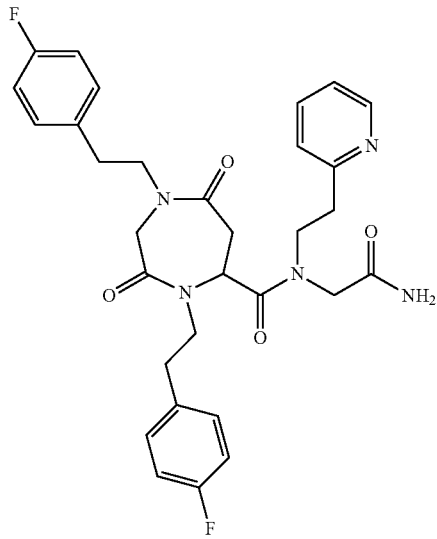 [SMILES: NC(=O)CN(CCc1ccccn1)C(=O)C1CC(=O)N(CCc2ccc(F)cc2)CC(=O)N1CCc1ccc(F)cc1]

The synthesis of compound Ia is illustrated in this patent application. The Rink amide resin (400 mg, 0.3 mmol) was treated with 3 mL of 20% piperidine in dimethylformamide and the mixture was stirred in a microwave reactor for 2 minutes at 60° C. The resin was filtered and washed with dimethylformamide (3×3 mL), isopropyl alcohol (3×3 mL) and dichloromethane (3×3 mL). The resin was treated with a solution of bromoacetic acid (208 mg, 5 eq.) and N,N'-diisopropylcarbodiimide (235 μL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). A solution of N-[2-2'-(pyridin-2-yl)ethylamine (180 μL, 5 eq.) and triethylamine (210 μL, 5 eq.) in 3 mL of dimethylformamide was added to the resin and the suspension was stirred for 2 minutes at 90° C. with microwave activation. The supernatant was removed, and the residue was filtered and washed with dimethylformamide (3×3 mL), isopropyl alcohol (3×3 mL) and dichloromethane (3×3 mL). Then the resin was treated with a solution of (Z)-3-(allyloxycarbonyl)acrylic acid (obtained with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 μL, 5 eq.) in dichloromethane:dimethylformamide (2:1, 3 mL). The reaction mixture was stirred at room temperature for 30 minutes in duplicate. The resin was filtered and washed with dichloromethane (3×3 mL), isopropyl alcohol (3×3 mL) and dimethylformamide (3×3 mL). Subsequently a solution of 2-(4'-fluorophenyl)ethylamine (200 μL, 5 eq.) and triethylamine (210 μL, 5 eq.) in 3 mL of dimethylformamide was added to the resin and the suspension was stirred for 3 hours at room temperature. The reaction was repeated for 16 hours at the same temperature. The supernatant was removed, and the residue was filtered and washed with dimethylformamide (3×3 mL), isopropyl alcohol (3×3 mL) and dichloromethane (3×3 mL). Then the resin was treated with a solution of bromoacetic acid (208 mg, 5 eq.) and N,N'-diisopropylcarbodiimide (235 μL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). A solution of 2-(4'-fluorophenyl)ethylamine (200 μL, 5 eq.) and triethylamine (210 μL, 5 eq.) in 3 mL of dimethylformamide was added to the resin and the suspension was stirred for 2 minutes at 90° C. with microwave activation. The supernatant was discarded, and the residue was filtered and washed with dimethylformamide (3×3 mL), isopropyl alcohol (3×3 mL) and dichloromethane (3×3 mL). Then the resin was treated with tetrakis(triphenylphosphine)palladium(0) (35 mg, 0.1 eq.) and phenylsilane (370 μL, 10 eq.) in anhydrous dichloromethane for 15 minutes at room temperature and under an argon atmosphere. This process was repeated three times. The supernatant was discarded, and the residue was filtered and washed with dimethylformamide (3×3 mL), isopropyl alcohol (3×3 mL) and dichloromethane (3×3 mL). The cyclization was performed by means of treatment with benzotriazol-1-yloxy-tris-pyrrolidine-phosphonium hexafluorophosphate (235 mg, 1.5 eq.), 1-hydroxybenzotriazole (61 mg, 1.5 eq.) and N,N-diisopropylethylamine (154 μL, 3 eq.) in dimethylformamide (3 mL). The reaction mixture was stirred at room temperature for 3 hours. The resin was filtered and washed with dichloromethane (3×3 mL), isopropyl alcohol (3×3 mL) and dimethylformamide (3×3 mL). Finally, the treatment of the resin with a mixture of trifluoroacetic acid/dichloromethane/water (60:40:2) released a reaction mixture containing compound Ia. The latter was filtered and the solvents were removed by means of evaporation under reduced pressure followed by lyophilization. The residue was purified by means of RP-HPLC at a semi-preparative scale applying an acetonitrile-water gradient (20% acetonitrile→80% acetonitrile, 30 minutes), providing 52 mg of the product sought (yield 30%, ≥98% purity).

HRMS-FAB: $C_{31}H_{33}F_2N_5O_4$ calcd. [M+H$^+$] 578.257886; found 578.257844.

3.2.—Compound Ib: [1,4-bis[2'-(4"-fluorophenyl)ethyl]-2-[N-aminocarbonlmethyl-N-(2'-(2"pyridyl)ethyl)carbonylmethyl]piperazine-3,6-dione

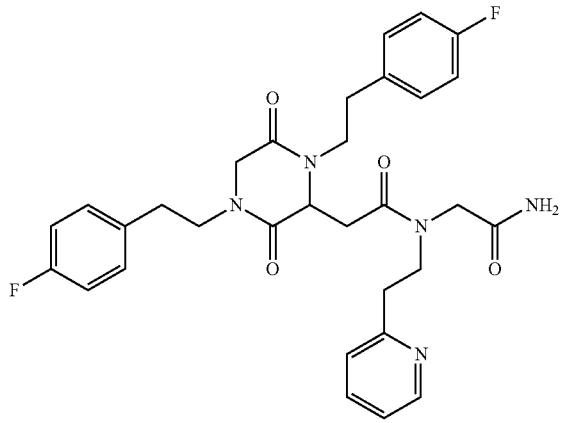 [SMILES: NC(=O)CN(CCc1ccccn1)C(=O)CC1C(=O)N(CCc2ccc(F)cc2)CC(=O)N1CCc1ccc(F)cc1]

The synthesis of compound Ib is shown in scheme II. All the solid-phase reactions in solid phase were performed in duplicate. The Rink amide resin (400 mg, 0.3 mmol) was treated with 3 mL of 20% piperidine in dimethylformamide, the mixture being stirred in a microwave reactor for 2 minutes at 60° C. The resin was filtered and washed with dimethylformamide (3×3 mL), isopropyl alcohol (3×3 mL) and dichloromethane (3×3 mL). The resin was treated with a solution of bromoacetic acid (208 mg, 5 eq.) and N,N'-diisopropylcarbodiimide (235 μL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). Next, a solution of 2-(4'-fluorophenyl)ethylamine (200 μL, 5 eq.) and triethylamine (210 μL, 5 eq.) in 3 mL of dimethylformamide was added to the resin, and the suspension was stirred for 2 minutes at 90° C. with microwave activation. The supernatant was removed, and the residue was filtered and washed with dimethylformamide (3×3 mL), isopropyl alcohol (3×3 mL) and dichloromethane (3×3 mL). The resin was treated with a solution of (Z)-3-(allyloxycarbonyl)acrylic acid (prepared with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 μL, 5 eq.) in dichloromethane:dimethylformamide (2:1, 3 mL). The reaction mixture was stirred at room temperature for 30 minutes. The latter was filtered and the resin was washed with dichloromethane (3×3 mL), isopropyl alcohol (3×3 mL) and dimethylformamide (3×3 mL). Then a solution of 2-(4'-fluorophenyl)ethylamine (200 μL, 5 eq.) and triethylamine (210 μL, 5 eq.) in 3 mL of dimethylformamide was added to the resin and the suspension was stirred for 3 hours at room temperature. The reaction was stirred for 16 hours at the same temperature. The supernatant was removed and the residue was filtered and washed with dimethylformamide (3×3 mL), isopropyl alcohol (3×3 mL) and dichloromethane (3×3 mL). Finally, the resin was treated with a mixture of trifluoroacetic acid/dichloromethane/water (60:40:2) for 30 minutes at room temperature. The hydrolysis mixture was filtered, the filtrates were pooled and the solvents were removed by means of evaporation under low pressure. The subsequent cyclization was achieved by means of treating the previous residue with 4 mL of dioxane for 30 minutes in reflux conditions (controlled by HPLC). Then a solution of 4 N sodium hydroxide and allyl alcohol (1:2, 1.5 mL) was added, the mixture being stirred for 30 minutes with reflux (controlled by HPLC). The reaction mixture was acidified with 1 N hydrochloric acid and the solvent was evaporated. The resulting residue was extracted with 2×10 mL of ethyl acetate, being dried on anhydrous magnesium sulfate and concentrated under vacuum. The solvent was removed by concentration under vacuum, the diketopiperazine intermediate being produced (90 mg, 72%) in the form of a colorless solid. This material was used in the following step without subsequent purification.

The resin containing the N-alkylglycine fragment was synthesized following a process similar to the one described above. Briefly, this fragment was obtained by means of treating the resin (290 mg, 0.22 mmol) with 20% piperidine in dimethylformamide, followed by acylation with bromoacetic acid (153 mg, 5 eq.) and N,N'-diisopropylcarbodiimide (175 μL, 5 eq.), and coupling of the amine with N-[2-2'-(pyridin-2-yl)ethylamine (135 μL, 5 eq.) in the presence of triethylamine (155 μL, 5 eq.). Then the diketopiperazine intermediate (90.0 mg, 1 eq.) was coupled to the resin in the presence of 1-hydroxybenzotriazole (45 mg, 1.5 eq.) and N,N'-diisopropylcarbodiimide (55 μL, 1.5 eq.) in dichloromethane:dimethylformamide (2:1, 3 mL). The reaction mixture was stirred at room temperature for 1 hour. The dry resin was washed with dichloromethane (3×3 mL), isopropyl alcohol (3×3 mL) and dimethylformamide (3×3 mL). Finally, the treatment of the resin with a 60:40:2 mixture of trifluoroacetic acid/dichloromethane/water produced a reaction mixture containing compound Ib. The latter was filtered and the solvents were removed by means of evaporation under low pressure, followed by lyophilization. The obtained residue was purified by means of RP-HPLC at a semi-preparative scale applying an acetonitrile-water gradient (30% acetonitrile→45% acetonitrile, 30 minutes) to yield 57 mg of the product sought (yield 33%, ≥98% purity).

HRMS-FAB: $C_{31}H_{33}F_2N_5O_4$ calcd. [M+H$^+$] 578.2501; found 578.2573.

Example 3.3

Compound N-aminocarbamoylmethyl-N-(2'-(2"-pyridyl)ethyl)-1-[2'-(2",4"-dichlorophenyl)ethyl]-4-[2'-(4"-fluorophenyl)ethyl]-3,7-dioxo-[1,4]diazepane-5-carboxamide

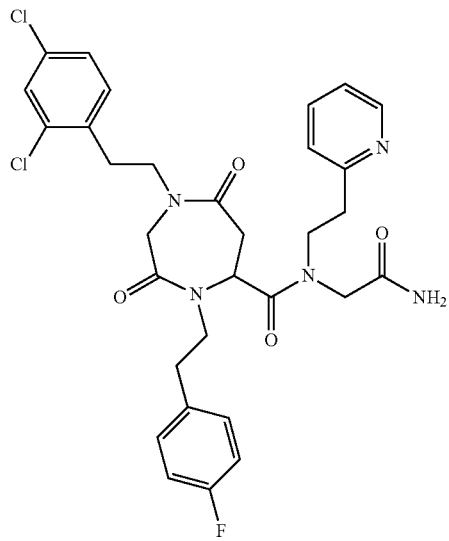 [SMILES: NC(=O)CN(CCc1ccccn1)C(=O)C1CC(=O)N(CCc2ccc(Cl)cc2Cl)CC(=O)N1CCc1ccc(F)cc1]

The Rink amide resin (400 mg, 0.3 mmol) is treated with 3 mL of 20% piperidine in dimethylformamide and the mixture is stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of N-[2-2'-(pyridin-2-yl)ethylamine (180 µL, 5 eq.) and triethylamine (210 µL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). Then the resin is treated with a solution of (Z)-3-(allyloxycarbonyl)acrylic acid (obtained with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture is stirred at room temperature for 30 minutes in duplicate. The resin is filtered and washed with dichloromethane (3×3 mL), isopropyl alcohol (3×3 mL) and dimethylformamide (3×3 mL). A solution of 2-(4'-fluorophenyl)ethylamine (200 µL, 5 eq.) and triethylamine (210 µL, 5 eq.) in 3 mL of dimethylformamide is subsequently added to the resin, and the suspension is stirred for 3 hours at room temperature. The reaction is repeated for 16 hours at the same temperature. The supernatant is removed, and the residue is filtered and washed with dimethylformamide (3×3 mL), isopropyl alcohol (3×3 mL) and dichloromethane (3×3 mL). Then the resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of 2-(2',4'-dichlorophenyl)ethylamine (240 µL, 5 eq.) and triethylamine (210 µL, 5 eq.) in 3 mL of dimethylformamide is added to the resin, and the suspension is stirred for 2 minutes at 90° C. with microwave activation. The supernatant is discarded, and the residue is filtered and washed with dimethylformamide (3×3 mL), isopropyl alcohol (3×3 mL) and dichloromethane (3×3 mL). Then the resin is treated with tetrakis(triphenylphosphine)palladium(0) (35 mg, 0.1 eq.) and phenylsilane (370 µL, 10 eq.) in anhydrous dichloromethane for 15 minutes at room temperature and under an argon atmosphere. This process is repeated three times. The supernatant is discarded and the residue is filtered and washed with dimethylformamide (3×3 mL), isopropyl alcohol (3×3 mL) and dichloromethane (3×3 mL). Cyclization is performed by means of treatment with benzotriazol-1-yloxy-tris-pyrrolidine-phosphonium hexafluorophosphate (235 mg, 1.5 eq.), 1-hydroxybenzotriazole (61 mg, 1.5 eq.) and N,N-diisopropylethylamine (154 µL, 3 eq.) in dimethylformamide (3 mL). The reaction mixture is stirred at room temperature for 3 hours. The resin is filtered and washed with dichloromethane (3×3 mL), isopropyl alcohol (3×3 mL) and dimethylformamide (3×3 mL). Finally, the treatment of the resin with a mixture of trifluoroacetic acid/dichloromethane/water (60:40:2) releases a reaction mixture containing the compound sought. This mixture is filtered and the solvents are removed by means of evaporation under reduced pressure followed by lyophilization. The residue is purified by means of RP-HPLC at a semi-preparative scale applying an acetonitrile-water gradient.

Example 3.4

Compound N-aminocarbamoylmethyl-N-(2'-(4"-methoxyphenyl)ethyl)-1-[2'-(2",4"-dichlorophenyl)ethyl]-4-[2'-(4"-fluorophenyl)ethyl]-3,7-dioxo-[1,4]diazepane-5-carboxamide

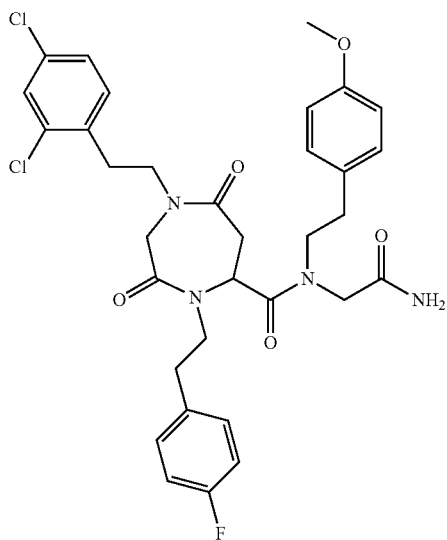 [SMILES: COc1ccc(CCN(CC(N)=O)C(=O)C2CC(=O)N(CCc3ccc(Cl)cc3Cl)CC(=O)N2CCc2ccc(F)cc2)cc1]

The Rink amide resin (400 mg, 0.3 mmol) is treated with 3 mL of 20% piperidine in dimethylformamide and the mixture is stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of 2-(4'-methoxyphenyl)ethylamine (235 µL, 5 eq.) and triethylamine (210 µL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). Then the resin is treated with a solution of (Z)-3-(allyloxycarbonyl)acrylic acid (obtained with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture is stirred at room temperature for 30 minutes in duplicate. The resin is filtered and washed with dichloromethane (3×3 mL), isopropyl alcohol (3×3 mL) and dimethylformamide (3×3 mL). A solution of N-2-(4'-fluorophenyl)ethylamine (200 µL, 5 eq.) and triethylamine (210 µL, 5 eq.) in 3 mL of dimethylformamide is subsequently added to the resin, and the suspension is stirred for 3 hours at room temperature. The reaction is repeated for 16 hours at the same temperature. The supernatant is removed, and the residue is filtered and washed with dimethylformamide (3×3 mL), isopropyl alcohol (3×3 mL) and dichloromethane (3×3 mL). Then the resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of 2-(2',4'-dichlorophenyl)ethylamine (240 µL, 5 eq.) and triethylamine (210 µL, 5 eq.) in 3 mL of dimethylformamide is added to the resin, and the suspension is stirred for 2 minutes at 90° C. with microwave activation. The supernatant is discarded, and the residue is filtered and washed with dimethylformamide (3×3 mL), isopropyl alcohol (3×3 mL) and dichloromethane (3×3 mL). Then the resin is treated with tetrakis(triphenylphosphine)palladium(0) (35 mg, 0.1 eq.) and phenylsilane (370 µL, 10 eq.) in anhydrous dichloromethane for 15 minutes at room temperature and under an argon atmosphere. This process is repeated three times. The supernatant is discarded and the residue is filtered and washed with dimethylformamide (3×3 mL), isopropyl alcohol (3×3 mL) and dichloromethane (3×3 mL). The cyclization is performed by means of treatment with benzotriazol-1-yloxy-tris-pyrrolidine-phosphonium hexafluorophosphate (235 mg, 1.5 eq.), 1-hydroxybenzotriazole (61 mg, 1.5 eq.) and N,N-diisopropylethylamine (154 µL, 3 eq.) in dimethylformamide (3 mL). The reaction mixture is stirred at room temperature for 3 hours. The resin is filtered and washed with dichloromethane (3×3 mL), isopropyl alcohol (3×3 mL) and dimethylformamide (3×3 mL). Finally, the treatment of the resin with a mixture of trifluoroacetic acid/dichloromethane/water (60:40:2) releases a reaction mixture containing the compound sought. This mixture is filtered and the solvents are removed by means of evaporation under reduced pressure followed by lyophilization. The residue is purified by means of RP-HPLC at a semi-preparative scale applying an acetonitrile-water gradient.

Example 3.5

Compound N-aminocarbamoylmethyl-N-(2'-(4"-methoxyphenyl)ethyl)-1,4-bis[2'-(4"-fluorophenyl)ethyl]-3,7-dioxo-[1,4]diazepane-5-carboxamide

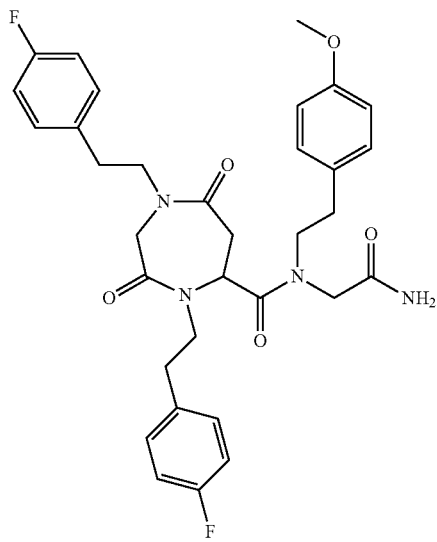 [SMILES: COc1ccc(CCN(CC(N)=O)C(=O)C2CC(=O)N(CCc3ccc(F)cc3)CC(=O)N2CCc2ccc(F)cc2)cc1]

The Rink amide resin (400 mg, 0.3 mmol) is treated with 3 mL of 20% piperidine in dimethylformamide and the mixture is stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of 2-(4'-methoxyphenyl)ethylamine (235 µL, 5 eq.) and triethylamine (210 µL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). Then the resin is treated with a solution of (Z)-3-(allyloxycarbonyl)acrylic acid (obtained with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture is stirred at room temperature for 30 minutes in duplicate. The resin is filtered and washed with dichloromethane (3×3 mL), isopropyl alcohol (3×3 mL) and dimethylformamide (3×3 mL). A solution of 2-(4'-fluorophenyl)ethylamine (200 µL, 5 eq.) and triethylamine (210 µL, 5 eq.) in 3 mL of dimethylformamide is subsequently added to the resin, and the suspension is stirred for 3 hours at room temperature. The reaction is repeated for 16 hours at the same temperature. The supernatant is removed, and the residue is filtered and washed with dimethylformamide (3×3 mL), isopropyl alcohol (3×3 mL) and dichloromethane (3×3 mL). Then the resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). A solution of 2-(4'-fluorophenyl)ethylamine (200 µL, 5 eq.) and triethylamine (210 µL, 5 eq.) in 3 mL of dimethylformamide is added to the resin, and the suspension is stirred for 2 minutes at 90° C. with microwave activation. The supernatant is discarded, and the residue is filtered and washed with dimethylformamide (3×3 mL), isopropyl alcohol (3×3 mL) and dichloromethane (3×3 mL). Then the resin is treated with tetrakis(triphenylphosphine)palladium(0) (35 mg, 0.1 eq.) and phenylsilane (370 µL, 10 eq.) in anhydrous dichloromethane for minutes at room temperature and under an argon atmosphere. This process is repeated three times. The supernatant is discarded and the residue is filtered and washed with dimethylformamide (3×3 mL), isopropyl alcohol (3×3 mL) and dichloromethane (3×3 mL). The cyclization is performed by means of treatment with benzotriazol-1-yloxy-tris-pyrrolidine-phosphonium hexafluorophosphate (235 mg, 1.5 eq.), 1-hydroxybenzotriazole (61 mg, 1.5 eq.) and N,N-diisopropylethylamine (154 µL, 3 eq.) in dimethylformamide (3 mL). The reaction mixture is stirred at room temperature for 3 hours. The resin is filtered and washed with dichloromethane (3×3 mL), isopropyl alcohol (3×3 mL) and dimethylformamide (3×3 mL). Finally, the treatment of the resin with a mixture of trifluoroacetic acid/dichloromethane/water (60:40:2) releases a reaction mixture containing the compound sought. This mixture is filtered and the solvents are removed by means of evaporation under reduced pressure followed by lyophilization. The residue is purified by means of RP-HPLC at a semi-preparative scale applying an acetonitrile-water gradient.

Example 3.6

Compound 1-[2'-(2'',4''-dichlorophenyl)ethyl]-4-[2'-(4''-fluorophenyl)ethyl]-2-[N-aminocarbonylmethyl-N-(2'-(2''pyridyl)ethyl)carbonylmethyl]piperazine-3,6-dione

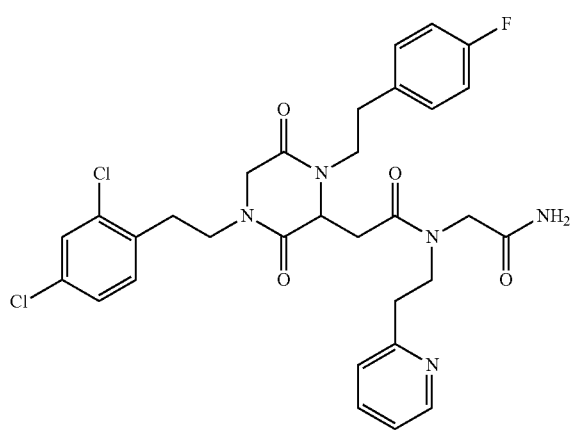 [SMILES: NC(=O)CN(CCc1ccccn1)C(=O)CC1C(=O)N(CCc2ccc(Cl)cc2Cl)CC(=O)N1CCc1ccc(F)cc1]

All the solid-phase reactions are performed in duplicate. The Rink amide resin (400 mg, 0.3 mmol) is treated with 3 mL of 20% piperidine in dimethylformamide, the mixture being stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). Next, a solution of 2-(2',4'-dichlorophenyl)ethylamine (240 µL, 5 eq.), and triethylamine (210 µL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). The resin is treated with a solution of (Z)-3-(allyloxycarbonyl)acrylic acid (prepared with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture is stirred at room temperature for 30 minutes. It is filtered and the resin is washed with dichloromethane (3×3 mL), isopropyl alcohol (3×3 mL) and dimethylformamide (3×3 mL). Then a solution of 2-(4'-fluorophenyl)ethylamine (200 µL, 5 eq.) and triethylamine (210 µL, 5 eq.) in 3 mL of dimethylformamide is added to the resin, and the suspension is stirred for 3 hours at room temperature. The reaction is stirred for 16 hours at the same temperature. The supernatant is removed, the residue is filtered and washed with dimethylformamide (3×3 mL), isopropyl alcohol (3×3 mL) and dichloromethane (3×3 mL). Finally, the resin is treated with a mixture of trifluoroacetic acid/dichloromethane/water (60:40:2) for 30 minutes at room temperature. The hydrolysis mixture is filtered, the filtrates are pooled and the solvents are removed by means of evaporation under low pressure. The subsequent cyclization is achieved by means of treating the previous residue with 4 mL of dioxane for 30 minutes in reflux conditions (controlled by HPLC). Then, a solution of 4 N sodium hydroxide and allyl alcohol (1:2, 1.5 mL) is added, the mixture being stirred for 30 minutes with reflux (controlled by HPLC). The reaction mixture is acidified with 1 N hydrochloric acid, and the solvent is evaporated. The resulting residue is extracted with 2×10 mL of ethyl acetate, being dried on anhydrous magnesium sulfate and concentrated under vacuum. The solvent is removed by concentration under vacuum, the diketopiperazine intermediate being produced. This material is used in the following step without subsequent purification.

The resin containing the N-alkylglycine fragment is synthesized following a process similar to the one described above. Briefly, this fragment is obtained by means of treating the resin with 20% piperidine in dimethylformamide, followed by acylation with bromoacetic acid (5 eq.) and N,N'-diisopropylcarbodiimide (5 eq.), and coupling of the amine with N-[2-2'-(pyridin-2-yl)ethylamine (5 eq.) in the presence of triethylamine (5 eq.). Then the diketopiperazine intermediate (1 eq.) is coupled to the resin in the presence of 1-hydroxybenzotriazole (1.5 eq.) and N,N'-diisopropylcarbodiimide (1.5 eq.) in dichloromethane:dimethylformamide (2:1, 3 mL). The reaction mixture is stirred at room temperature for 1 hour. The dry resin is washed with dichloromethane (3×3 mL), isopropyl alcohol (3×3 mL) and dimethylformamide (3×3 mL). Finally, the treatment of the resin with a 60:40:2 mixture of trifluoroacetic acid/dichloromethane/water produces a reaction mixture containing the compound sought. This compound is filtered and the solvents are removed by means of evaporation under low pressure, followed by lyophilization. The obtained residue is purified by means of RP-HPLC at a semi-preparative scale applying an acetonitrile-water gradient.

Example 3.7

Compound 1-[2'-(2",4"-dichlorophenyl)ethyl]-4-[2'-(4"-fluorophenyl)ethyl]-2-[N-aminocarbonylmethyl-N-(2'-(4'-methoxyphenyl)ethyl)carbonylmethyl]piperazine-3,6-dione

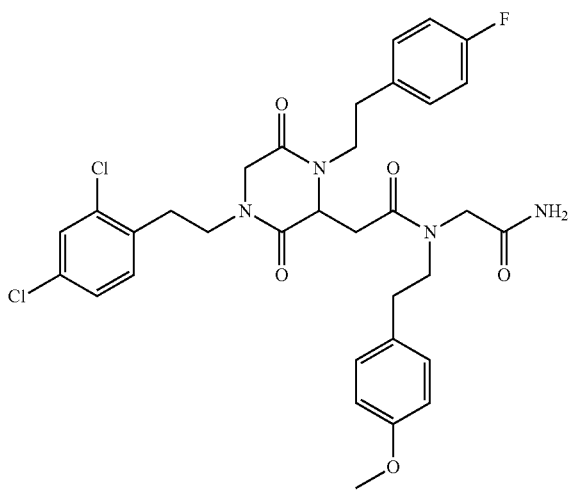 [SMILES: COc1ccc(CCN(CC(N)=O)C(=O)CC2C(=O)N(CCc3ccc(Cl)cc3Cl)CC(=O)N2CCc2ccc(F)cc2)cc1]

All the solid-phase reactions are performed in duplicate. The Rink amide resin (400 mg, 0.3 mmol) is treated with 3 mL of 20% piperidine in dimethylformamide, the mixture being stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 μL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). Next, a solution of 2-(2',4'-dichlorophenyl)ethylamine (240 μL, 5 eq.), and triethylamine (210 μL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). The resin is treated with a solution of (Z)-3-(allyloxycarbonyl) acrylic acid (prepared with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 μL, 5 eq.) in dichloromethane:dimethylformamide (2:1, 3 mL). The reaction mixture is stirred at room temperature for 30 minutes. The mixture is filtered and the resin is washed with dichloromethane (3×3 mL), isopropyl alcohol (3×3 mL) and dimethylformamide (3×3 mL). Then a solution of 2-(4'-fluorophenyl)ethylamine (200 μL, 5 eq.) and triethylamine (210 μL, 5 eq.) in 3 mL of dimethylformamide is added to the resin, and the suspension is stirred for 3 hours at room temperature. The reaction is stirred for 16 hours at the same temperature. The supernatant is removed, and the residue is filtered and washed with dimethylformamide (3×3 mL), isopropyl alcohol (3×3 mL) and dichloromethane (3×3 mL). Finally, the resin is treated with a mixture of trifluoroacetic acid/dichloromethane/water (60:40:2) for 30 minutes at room temperature. The hydrolysis mixture is filtered, the filtrates are pooled and the solvents are removed by means of evaporation under low pressure. The subsequent cyclization is achieved by means of treating the previous residue with 4 mL of dioxane for 30 minutes in reflux conditions (controlled by HPLC). Then, a solution of 4 N sodium hydroxide and allyl alcohol (1:2, 1.5 mL) is added, the mixture being stirred for minutes with reflux (controlled by HPLC). The reaction mixture is acidified with 1 N hydrochloric acid, and the solvent is evaporated. The resulting residue is extracted with 2×10 mL of ethyl acetate, being dried on anhydrous magnesium sulfate and concentrated under vacuum. The solvent is removed by concentration under vacuum, the diketopiperazine intermediate being produced. This material is used in the following step without subsequent purification.

The resin containing the N-alkylglycine fragment is synthesized following a process similar to the one described above. Briefly, this fragment is obtained by means of treating the resin with 20% piperidine in dimethylformamide, followed by acylation with bromoacetic acid (5 eq.) and N,N'-diisopropylcarbodiimide (5 eq.), and coupling of the amine with 2-(4'-methoxyphenyl)ethylamine (5 eq.) in the presence of triethylamine (5 eq.). Then the diketopiperazine intermediate (1 eq.) is coupled to the resin in the presence of 1-hydroxybenzotriazole (1.5 eq.) and N,N'-diisopropylcarbodiimide (1.5 eq.) in dichloromethane:dimethylformamide (2:1, 3 mL). The reaction mixture is stirred at room temperature for 1 hour. The dry resin is washed with dichloromethane (3×3 mL), isopropyl alcohol (3×3 mL) and dimethylformamide (3×3 mL). Finally, the treatment of the resin with a 60:40:2 mixture of trifluoroacetic acid/dichloromethane/water produces a reaction mixture containing the compound sought. This compound is filtered and the solvents are removed by means of evaporation under low pressure, followed by lyophilization. The obtained residue is purified by means of RP-HPLC at a semi-preparative scale applying an acetonitrile-water gradient.

Example 3.8

Compound 1,4-bis[2'-(4"-fluorophenyl)ethyl]-2-[N-aminocarbonylmethyl-N-(2'-(4"-methoxyphenyl)ethyl)carbonylmethyl]piperazine-3,6-dione

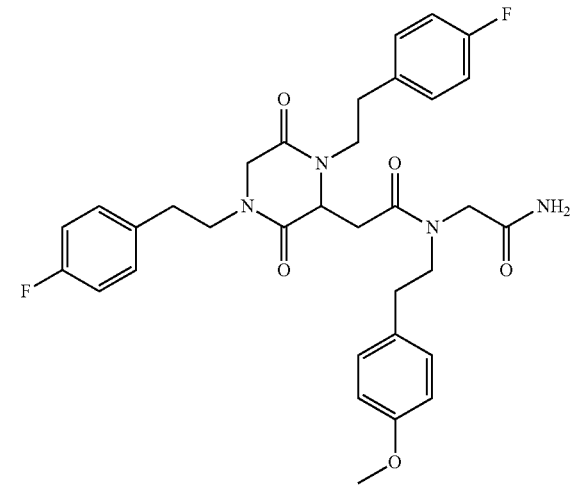 [SMILES: COc1ccc(CCN(CC(N)=O)C(=O)CC2C(=O)N(CCc3ccc(F)cc3)CC(=O)N2CCc2ccc(F)cc2)cc1]

All the solid-phase reactions are performed in duplicate. The Rink amide resin (400 mg, 0.3 mmol) is treated with 3 mL of 20% piperidine in dimethylformamide, the mixture being stirred in a microwave reactor for 2 minutes at 60° C. The resin is filtered and washed with dimethylformamide (3×3 mL), isopropyl alcohol (3×3 mL) and dichloromethane (3×3 mL). The resin is treated with a solution of bromoacetic acid (208 mg, 5 eq.) and N,N'-diisopropylcarbodiimide (235 µL, 5 eq.) in dimethylformamide (3 mL). The reaction mixture is stirred for 2 minutes at 60° C. in a microwave reactor. The resin is filtered and washed with dichloromethane (3×3 mL), isopropyl alcohol (3×3 mL) and dimethylformamide (3×3 mL). Next, a solution of 2-(4'-fluorophenyl)ethylamine (200 µL, 5 eq.), and triethylamine (210 µL, 5 eq.) in 3 mL of dimethylformamide is added to the resin, and the suspension is stirred for 2 minutes at 90° C. with microwave activation. The supernatant is removed, and the residue is filtered and washed with dimethylformamide (3×3 mL), isopropyl alcohol (3×3 mL) and dichloromethane (3×3 mL). The resin is treated with a solution of (Z)-3-(allyloxycarbonyl)acrylic acid (prepared with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture is stirred at room temperature for 30 minutes. The mixture is filtered and the resin is washed with dichloromethane (3×3 mL), isopropyl alcohol (3×3 mL) and dimethylformamide (3×3 mL). Then a solution of 2-(4'-fluorophenyl)ethylamine (200 µL, 5 eq.) and triethylamine (210 µL, 5 eq.) in 3 mL of dimethylformamide is added to the resin, and the suspension is stirred for 3 hours at room temperature. The reaction is stirred for 16 hours at the same temperature. The supernatant is removed, and the residue is filtered and washed with dimethylformamide (3×3 mL), isopropyl alcohol (3×3 mL) and dichloromethane (3×3 mL). Finally, the resin is treated with a mixture of trifluoroacetic acid/dichloromethane/water (60:40:2) for 30 minutes at room temperature. The hydrolysis mixture is filtered, the filtrates are pooled and the solvents are removed by means of evaporation under low pressure. The subsequent cyclization is achieved by means of treating the previous residue with 4 mL of dioxane for 30 minutes in reflux conditions (controlled by HPLC). Then, a solution of 4 N sodium hydroxide and allyl alcohol (1:2, 1.5 mL) is added, the mixture being stirred for 30 minutes with reflux (controlled by HPLC). The reaction mixture is acidified with 1 N hydrochloric acid, and the solvent is evaporated. The resulting residue is extracted with 2×10 mL of ethyl acetate, being dried on anhydrous magnesium sulfate and concentrated under vacuum. The solvent is removed by concentration under vacuum, the diketopiperazine intermediate being produced. This material is used in the following step without subsequent purification.

The resin containing the N-alkylglycine fragment is synthesized following a process similar to the one described above. In summary, this fragment is obtained by means of treating the resin (290 mg, 0.22 mmol) with 20% piperidine in dimethylformamide, followed by acylation with bromoacetic acid (153 mg, 5 eq.) and N,N'-diisopropylcarbodiimide (175 µL, 5 eq.), and coupling of the amine with 2-(4'-methoxyphenyl)ethylamine (235 µL, 5 eq.) in the presence of triethylamine (155 µL, 5 eq.). Then, the diketopiperazine intermediate (90.0 mg, 1 eq.) is coupled to the resin in the presence of 1-hydroxybenzotriazole (45 mg, 1.5 eq.) and N,N'-diisopropylcarbodiimide (55 µL, 1.5 eq.) in dichloromethane:dimethylformamide (2:1, 3 mL). The reaction mixture is stirred at room temperature for 1 hour. The dry resin is washed with dichloromethane (3×3 mL), isopropyl alcohol (3×3 mL) and dimethylformamide (3×3 mL). Finally, the treatment of the resin with a 60:40:2 mixture of trifluoroacetic acid/dichloromethane/water produces a reaction mixture containing the compound sought. This compound is filtered and the solvents are removed by means of evaporation under low pressure, followed by lyophilization. The obtained residue is purified by means of RP-HPLC at a semi-preparative scale applying an acetonitrile-water gradient.

Example 3.9

Compound N-aminocarbamoylmethyl-N-[2'-(2",4"-dichlorophenyl)ethyl]-1,4-bis[2'-(4"-fluorophenyl)ethyl]-3,7-dioxo-[1,4]diazepane-5-carboxamide

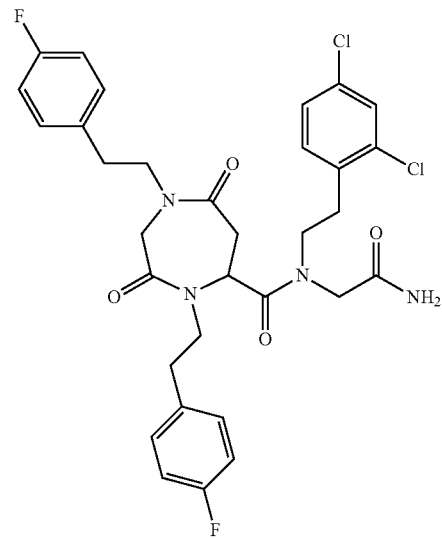 [SMILES: NC(=O)CN(CCc1ccc(Cl)cc1Cl)C(=O)C1CC(=O)N(CCc2ccc(F)cc2)CC(=O)N1CCc1ccc(F)cc1]

The Rink amide resin (400 mg, 0.3 mmol) was treated with 3 mL of 20% piperidine in dimethylformamide and the mixture was stirred in a microwave reactor for 2 minutes at 60° C. The resin was filtered and washed with dimethylformamide (3×3 mL), isopropyl alcohol (3×3 mL) and dichloromethane (3×3 mL). The resin was treated with a solution of bromoacetic acid (208 mg, 5 eq.) and N,N'-diisopropylcarbodiimide (235 µL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). A solution of 2-(2',4'-dichlorophenyl)ethylamine (240 µL, 5 eq.) and triethylamine (210 µL, 5 eq.) in 3 mL of dimethylformamide was added to the resin, and the suspension was stirred for 2 minutes at 90° C. with microwave activation. The supernatant was removed, and the residue was filtered and washed with dimethylformamide (3×3 mL), isopropyl alcohol (3×3 mL) and dichloromethane (3×3 mL). Then the resin was treated with a solution of (Z)-3-(allyloxycarbonyl)acrylic acid (obtained with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture was stirred at room temperature for 30 minutes in duplicate. The resin was filtered and washed with dichloromethane (3×3 mL), isopropyl alcohol (3×3 mL) and dimethylformamide (3×3 mL). Subsequently, a solution of 2-(4'-fluorophenyl)ethylamine (200 µL, 5 eq.) and triethylamine (210 µL, 5 eq.) in 3 mL of dimethylformamide was added to the resin, and the suspension was stirred for 3 hours at room temperature. The reaction was repeated for 16 hours at the same temperature. The supernatant was removed, and the residue was filtered and washed with dimethylformamide (3×3 mL), isopropyl alcohol (3×3 mL) and dichloromethane (3×3 mL). Then the resin was treated with a solution of bromoacetic acid (208 mg, 5 eq.) and N,N'-diisopropylcarbodiimide (235 µL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). A solution of 2-(4'-fluorophenyl)ethylamine (200 µL, 5 eq.) and triethylamine (210 µL, 5 eq.) in 3 mL of dimethylformamide was added to the resin, and the suspension was stirred for 2 minutes at 90° C. with microwave activation. The supernatant was discarded, and the residue was filtered and washed with dimethylformamide (3×3 mL), isopropyl alcohol (3×3 mL) and dichloromethane (3×3 mL). Then the resin was treated with tetrakis(triphenylphosphine)palladium(0) (35 mg, 0.1 eq.) and phenylsilane (370 µL, 10 eq.) in anhydrous dichloromethane for 15 minutes at room temperature and under an argon atmosphere. This process was repeated three times. The supernatant was discarded, and the residue was filtered and washed with dimethylformamide (3×3 mL), isopropyl alcohol (3×3 mL) and dichloromethane (3×3 mL). The cyclization was performed by means of treatment with benzotriazol-1-yloxy-tris-pyrrolidine-phosphonium hexafluorophosphate (235 mg, 1.5 eq.), 1-hydroxybenzotriazole (61 mg, 1.5 eq.) and N,N-diisopropylethylamine (154 µL, 3 eq.) in dimethylformamide (3 mL). The reaction mixture was stirred at room temperature for 3 hours. The resin was filtered and washed with dichloromethane (3×3 mL), isopropyl alcohol (3×3 mL) and dimethylformamide (3×3 mL). Finally, the treatment of the resin with a mixture of trifluoroacetic acid/dichloromethane/water (60:40:2) released a reaction mixture containing the compound sought. The latter was filtered and the solvents were removed by means of evaporation under reduced pressure followed by lyophilization. The residue was purified by means of RP-HPLC at a semi-preparative scale applying an acetonitrile-water gradient (20% acetonitrile→50% acetonitrile, 30 minutes), providing 77.3 mg of the product sought (yield 38%, ≥98% purity).

ESI-MS: $C_{32}H_{32}Cl_2F_2N_4O_4$ calcd. [M+H$^+$] 645.2; found: [M+H$^+$] 645.2.

Example 3.10

Compound [1,4-bis[2'-(4''-fluorophenyl)ethyl]-2-[N-aminocarbonylmethyl-N-(2'-(2'',4''-dichlorophenyl)ethyl)carbonylmethyl]piperazine-3,6-dione

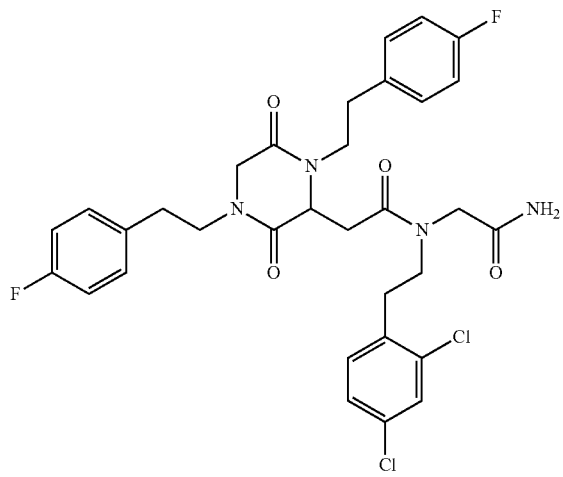 [SMILES: NC(=O)CN(CCc1ccc(Cl)cc1Cl)C(=O)CC1C(=O)N(CCc2ccc(F)cc2)CC(=O)N1CCc1ccc(F)cc1]

All the solid-phase reactions were performed in duplicate. The Rink amide resin (400 mg, 0.3 mmol) was treated with 3 mL of 20% piperidine in dimethylformamide, the mixture being stirred in a microwave reactor for 2 minutes at 60° C. The resin was filtered and washed with dimethylformamide (3×3 mL), isopropyl alcohol (3×3 mL) and dichloromethane (3×3 mL). The resin was treated with a solution of bromoacetic acid (208 mg, 5 eq.) and N,N'-diisopropylcarbodiimide (235 µL, 5 eq.) in dimethylformamide (3 mL). The reaction mixture was stirred for 2 minutes at 60° C. in a microwave reactor. The resin was filtered and washed with dichloromethane (3×3 mL), isopropyl alcohol (3×3 mL) and dimethylformamide (3×3 mL). Then a solution of 2-(4'-fluorophenyl)ethylamine (200 µL, 5 eq.) and triethylamine (210 µL, 5 eq.) in 3 mL of dimethylformamide was added to the resin, and the suspension was stirred for 2 minutes at 90° C. with microwave activation. The supernatant was removed, and the residue was filtered and washed with dimethylformamide (3×3 mL), isopropyl alcohol (3×3 mL) and dichloromethane (3×3 mL). The resin was treated with a solution of (Z)-3-(allyloxycarbonyl)acrylic acid (prepared with an 85% yield from maleic anhydride and allyl alcohol in chloroform for 50 minutes at 60° C. with microwave activation) (234 mg, 5 eq.), 1-hydroxybenzotriazole (203 mg, 5 eq.) and N,N'-diisopropylcarbodiimide (235 µL, 5 eq.) in dichloromethane:dimethylformamide (2:1, 3 mL). The reaction mixture was stirred at room temperature for 30 minutes. The mixture was filtered and the resin was washed with dichloromethane (3×3 mL), isopropyl alcohol (3×3 mL) and dimethylformamide (3×3 mL). Then a solution of 2-(4'-fluorophenyl)ethylamine (200 µL, 5 eq.) and triethylamine (210 µL, 5 eq.) in 3 mL of dimethylformamide was added to the resin, and the suspension was stirred for 3 hours at room temperature. The reaction was stirred for 16 hours at the same temperature. The supernatant was removed, the residue was filtered and washed with dimethylformamide (3×3 mL), isopropyl alcohol (3×3 mL) and dichloromethane (3×3 mL). Finally, the resin was treated with a mixture of trifluoroacetic acid/dichloromethane/water (60:40:2) for 30 minutes at room temperature. The hydrolysis mixture was filtered, the filtrates were pooled and the solvents were removed by means of evaporation under low pressure. The subsequent cyclization was achieved by means of treating the previous residue with 4 mL of dioxane for 30 minutes in reflux conditions (controlled by HPLC). Then a solution of 4 N sodium hydroxide and allyl alcohol (1:2, 1.5 mL) was added, the mixture being stirred for 30 minutes with reflux (controlled by HPLC). The reaction mixture was acidified with 1 N hydrochloric acid and the solvent was evaporated. The resulting residue was extracted with 2×10 mL of ethyl acetate, being dried on anhydrous magnesium sulfate and concentrated under vacuum. The solvent was removed by concentration under vacuum, the intermediate diketopiperazine (90 mg, 72%) being produced in the form of a colorless solid. This material was used in the following step without subsequent purification.

The resin containing the N-alkylglycine fragment was synthesized following a process similar to the one described above. Briefly, this was obtained by means of treating the resin (290 mg, 0.22 mmol) with 20% piperidine in dimethylformamide, followed by acylation with bromoacetic acid (153 mg, 5 eq.) and N,N'-diisopropylcarbodiimide (175 µL, 5 eq.), and coupling of the amine with 2-(2',4'-dichlorophenyl)ethylamine (170 µL, 5 eq.) in the presence of triethylamine (155 µL, 5 eq.). Then the diketopiperazine intermediate (90.0 mg, 1 eq.) was coupled to the resin in the presence of 1-hydroxybenzotriazole (45 mg, 1.5 eq.) and N,N'-diisopropylcarbodiimide (55 μL, 1.5 eq.) in dichloromethane:dimethylformamide (2:1, 3 mL). The reaction mixture was stirred at room temperature for 1 hour. The dry resin was washed with dichloromethane (3×3 mL), isopropyl alcohol (3×3 mL) and dimethylformamide (3×3 mL). Finally, the treatment of the resin with a mixture of 60:40:2 trifluoroacetic acid/dichloromethane/water produced a reaction mixture containing the compound sought. The latter was filtered and the solvents were removed by means of evaporation under low pressure, followed by lyophilization. The obtained residue was purified by means of RP-HPLC at a semi-preparative scale applying an acetonitrile-water gradient (30% acetonitrile→45% acetonitrilo, 30 minutes) to yield 71.7 mg of the product sought (yield 35%, ≥99% purity). ESI-MS: $C_{32}H_{32}Cl_2F_2N_4O_4$ calcd. $[M+H^+]$ 645.2; found: $[M+H^+]$ 645.1.

Example 4

Effects of Compounds Ia and Ib on the Interaction Between UBC13 and UEV1

The computational analysis described in Example 2 supports the hypothesis that compounds Ia and Ib dock with a good affinity in the hydrophobic furrow of the surface of UBC13 normally used for its specific interaction with the first aliphatic helix of UEV proteins (Mms2p, UEV1 and UEV2). This suggests that said compounds can competitively interfere with the interaction between UBC13 and UEV1 (or Mms2p and UEV2). To demonstrate it experimentally, the capacity of compounds Ia and Ib to inhibit the UBC13-UEV1 interaction was analyzed using two types of assays:

(1) two-hybrid assay in yeasts for the UBC13-UEV1 interaction, applying the process described in Example 1; and (2) interaction between the UBC13 and UEV1 proteins in acellular systems, using recombinant proteins produced in *Escherichia coli*.

Figure 5:
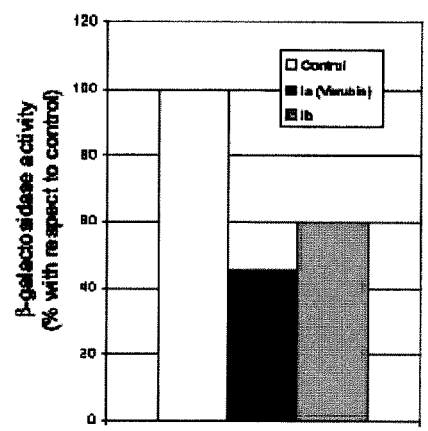
FIG. 5. Inhibition by compounds Ia (Varubin) and Ib of the interaction between the UBC13 and UEV1 proteins. (A) Two-hybrid assay in yeasts. Positive cells for the UBC13-UEV1 interaction were incubated with 100 μM of compound Ia or Ib. The interaction activities were standardized with respect to cells without cyclic compounds, and with respect to β-galactosidase activities of the positive interaction control (large T—p53) in the presence of the same concentrations of the 2 compounds. (B) Purified recombinant protein interaction assay. Recombinant GST-UBC13 was pre-incubated with 100 μM of compound Ia or Ib, and the capacity of UEV1 to interact on GST-UBC13 after the binding of the complex on glutathione-Sepharose columns was determined. E, fraction eluted from the column (not bound to GST-UBC13), B fraction remaining in the column (bound to GST-UBC13, eluted with buffer containing reduced glutathione).
Figure 5:
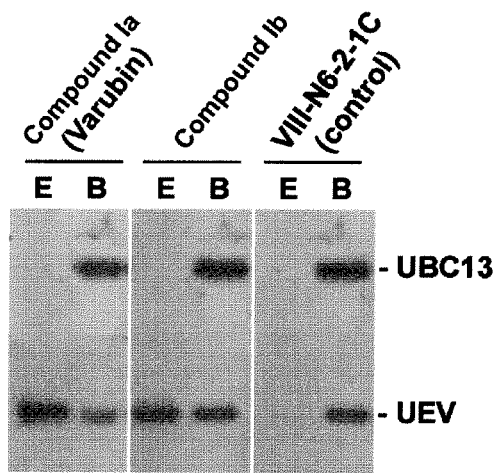

The effect of compounds Ia and Ib on the UBC13-UEV1 interaction in two-hybrid assays in yeasts was performed by incubating cells of the *Saccharomyces cerevisiae* strain AH109, grown in a selective medium, with 100 μM of either compound. The interaction of Sv40 large T and p53 proteins was used as positive interaction control. The intensity of the interactions was determined colorimetrically by means of detecting the β-galactosidase activity, using O-nitrophenyl-p-galactopyranoside (ONPG) as a substrate, each determination being performed in triplicate. In these conditions, it is shown in FIG. 5(A) that compound Ia, at a concentration of 100 μM, inhibits the interaction between UBC13 and UEV1 by close to 60%, whereas the inhibition of this interaction by compound Ib is close to 40%. Neither of these two compounds inhibits the interaction, used as control, between p53 and large T, which indicates that both compounds specifically inhibit the interaction between UBC13 and UEV1. These results also suggest that compound Ia inhibits this interaction with higher efficiency than compound Ib.

To determine the activity of these compounds in acellular assays, protein-protein interaction experiments were performed with recombinant proteins produced in *Escherichia coli*. To express UBC13 and UEV1, bacterial cells of the *E. coli* strain BL21 were transformed with plasmids pGEX-4T1-UBC13 or pGEX-4T3-UEV1, transformed colonies being selected by means of growth in plates with ampicillin (100 μg/mL). Individual colonies were transferred to 3 L of LB medium without antibiotics, being grown with stirring at 37° C. until the culture reached the exponential phase ($OD_{600}$~0.6), at which time the expression of the recombinant proteins was induced by means of adding isopropyl α-D-thiogalactopyranoside (IPTG, Sigma I-6758) at a concentration of 1 mM for 5 hours to the culture. The cultures were transferred to tubes, centrifuged and the cell pellets were resuspended in twice their volume of phosphate buffered saline (PBS) at pH 7.4 and were broken in a Cell Disruptor instrument (Constant Systems). The cell lysates were filtered through cellulose acetate filters with 45 μM pores (Millipore SLHA033SS) and were applied to GSTrap FF columns (Amersham Biosciences 17-5131-01). In the case of UEV1, the protein bound specifically to the column was subjected to enzymatic digestion on the same column with 50 units of thrombin (Amersham Biosciences 27-0846-01) at 25° C. overnight. A HiTrapBenzamidine FF column (Amersham Biosciences 27-0846-01) was coupled to the previous column, such that the GST unit was trapped in the first column, and the thrombin in the second column. Then the UEV1 protein was eluted, without the GST portion, followed by a subsequent step of purification by means of gel filtration chromatography with a Superdex 75 column. The GST-UBC13 recombinant protein was expressed as indicated above, being purified by means of affinity chromatography in GSTrap FF columns, followed by filtration chromatography in Superdex 75. The fractions corresponding to the purified proteins were concentrated by means of centrifugation in Centricon YM-10 columns (Millipore 4205), being stored at 4° C. until their use.

To determine the effects of compounds Ia and Ib on the interaction of UBC13 with UEV1, 2 μL of the GST-UBC13 chimeric recombinant protein, at a concentration of 4.09 μmg/mL in a 50 mM Hepes buffer, 100 mM NaCl, 1 mM EDTA, 0.5 mM DTT at pH 7.6 were pre-incubated for 30 minutes at room temperature with the compounds Varubin, Ib or the cyclic control compound VIII-N6-2-1C at final concentrations of 10 nM, 100 nM, 1 μM, 10 μM or 100 μM. These mixtures were immobilized in solid phase by means of incubating for 60 minutes with Glutathione Sepharose 4B matrix (Amersham Biosciences), followed by washings with 10 matrix volumes of 50 mM Hepes buffer, 100 mM NaCl, 1 mM EDTA, 0.5 mM DTT at pH 7.6. Then the columns were incubated for 45 minutes with 10 μL of UEV1 protein at a concentration of 0.15 μg/mL in the same buffer. The UEV1 protein not bound to the columns (eluted fraction, or E) was collected by means of centrifugation at 14,000 g, the columns then being washed with 10 volumes of the previous buffer. Then GST-UBC13 and GST-UBC13-UEV1 complexes were eluted by means of incubating with an elution buffer containing 10 mM of reduced glutathione in 50 mM Tris-HCl pH 8.0 (remaining fraction, or B). Fractions E and B were concentrated by means of centrifugation in Centricon YM-10 columns, denatured by means of boiling in Laemmli buffer (250 mM Tris-HCl, 10% SDS, 500 mM DTT, 0.5% bromophenol blue, 50% glycerol, pH 6.8) and were separated electrophoretically in 10% polyacrylamide-SDS gels. After the electrophoresis, the proteins were electrophoretically transferred to PVDF membranes, which were pre-incubated for 1 hour with blocking buffer (5% skimmed milk in PBS pH 7.4 with 0.1% Tween-20), and then incubated for 1 hour with rabbit anti-UEV1 or anti-UBC13 antibodies. These antibodies were previously produced in this laboratory by means of immunizing rabbits with synthetic peptides corresponding to specific UEV1 or UBC13 sequences, respectively, the antibodies being purified from the immune sera by means of affinity chromatography with columns on which the immunizing peptides were immobilized [37]. After the incubation with these antibodies, the membranes were washed three times with 20 mL of PBS-Tween-20, and were incubated for 30 minutes with horseradish peroxidase-conjugated goat antirabbit immunoglobulin antibodies (Dako Cytomation) diluted to 1:1000 in blocking buffer. After three washings with PBS-Tween-20, the reactions on the membranes were viewed by means of chemoluminescence with the ECL system (Amersham) and exposure on autoradiographic films.

The results of this assay are shown in FIG. 5(B), which shows that compounds Ia and Ib, but not the cyclic control compound VIII-N6-2-1C, efficiently inhibit the binding of UEV1 to GST-UBC13, since up to 60% (for compound Ia) or 40% (for compound Ib) of UEV1 appears in the fraction which is eluted and not bound to GST-UBC13. Although FIG. 5(B) only shows the results of the assay performed with 100 µM of cyclic compounds, an efficient inhibition of the interaction of UEV1 with UBC13 at much lower concentrations, of up to 10 nM of compounds Ia and Ib was also observed. Taking into account that the UEV1 and UBC13 proteins interact with one another with a high affinity ($K_D \approx 5 \times 10^{-10}$ M, a constant which has been determined in a Biacore T100 instrument), these results suggest that the inhibition by compounds Ia and Ib of the interaction between UBC13 and UEV1 is due to the competitive interaction of these compounds with the surface of UBC13 normally used for its interaction with the first aliphatic helix of UEV1.

Example 5

Effects of Compound Ia on the Polyubiquitylation Mediated by UBC13-UEV1

The inhibition by compounds Ia and Ib of the interaction between UBC13 and UEV1, described in Example 4, indicates that these compounds can inhibit the enzymatic activity of UBC13. As described in the Background, K63 type polyubiquitylation catalyzed by UBC13-UEV1 requires the interaction between both subunits of the heterodimer. The capacity of compound Ia, the most active of the 2 compounds as inhibitor of the interaction between UBC13 and UEV1, to affect this enzymatic activity was analyzed by means of in vitro free polyubiquitin chain formation assays. In this assay, the formation of polyubiquitin chains in reactions containing 0.1 µM of E1 enzyme (Boston Biochem), 0.2 µM of UBC13, 0.2 µM of UEV1 (produced as described in Example 4), 117 µM of wild-type ubiquitin (Biomol UW8795) or mutated in all the lysines except the lysine in position 63 (ubiquitin K63) or in position 48 (ubiquitin K48; Boston Biochem), is allowed in a reaction buffer with 50 mM of Tris-HC at pH 7.6, 5 mM of $MgCl_2$ and 0.5 mM of dithiothreitol. For the treatments with compound Ia (Varubin), UBC13 was pre-incubated for 10 minutes at room temperature with 100 µM of the compound before being added to the reaction. The reaction was initiated by means of adding 2 mM of ATP, and it was performed by means of incubating at 37° C. at different times, being stopped by means of adding Laemmli buffer (250 mM Tris-HCl, 10% SDS, 500 mM DTT, 0.5% bromophenol blue and 50% glycerol at pH 6.8) and boiling for 3 minutes. The samples were separated electrophoretically in polyacrylamide-SDS gels and transferred electrophoretically to PVDF membranes. The immunodetection process described in Example 4 was followed, the ubiquitin molecules being detected with rabbit anti-ubiquitin antibody (Biomol UG 9510), and the reactivity being revealed by chemoluminescence.

Figure 6A:
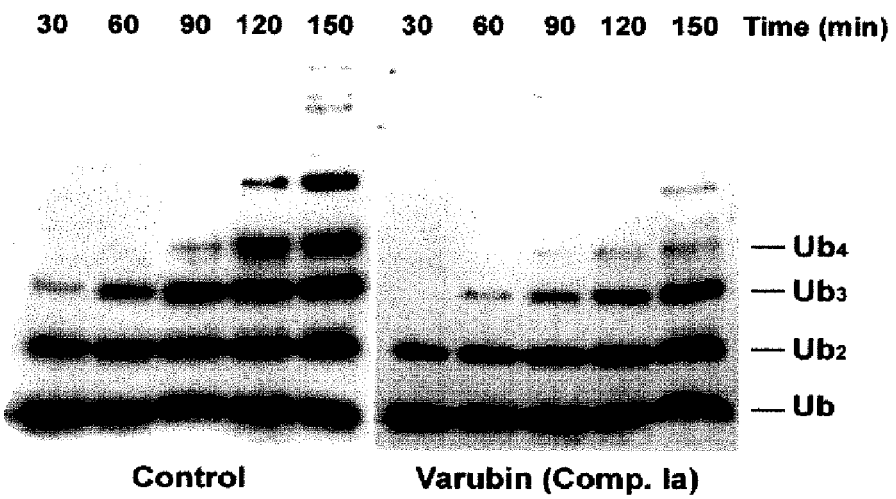
FIG. 6. Inhibition of the catalytic activity of UBC13-UEV1, in in vitro polyubiquitylation assays. (A) Accumulation over time of free polyubiquitins in control reactions or in the presence of 100 μM of compound Ia. The ubiquitin used in these reactions is wild-type ubiquitin (with the 7 lysines available for forming isopeptide bonds). The monoubiquitylated (Ub) and diubiquitylated ($Ub_2$) forms are present at time 0 and their abundance does not vary significantly throughout the entire kinetics. The triubiquitylated ($Ub_3$) and tetraubiquitylated ($Ub_4$) forms accumulate with third-order kinetics, as shown in (B). In (C) the reactions are performed with ubiquitin K63 (of the 7 lysines available, only the one of position 63 is available; the remaining lysines have mutated into arginines and are therefore not available for forming isopeptide bonds). The reactions were conducted in the same conditions as those shown in (A), in the presence or in the absence (control) of 100 μM of Ia.
Figure 6B:
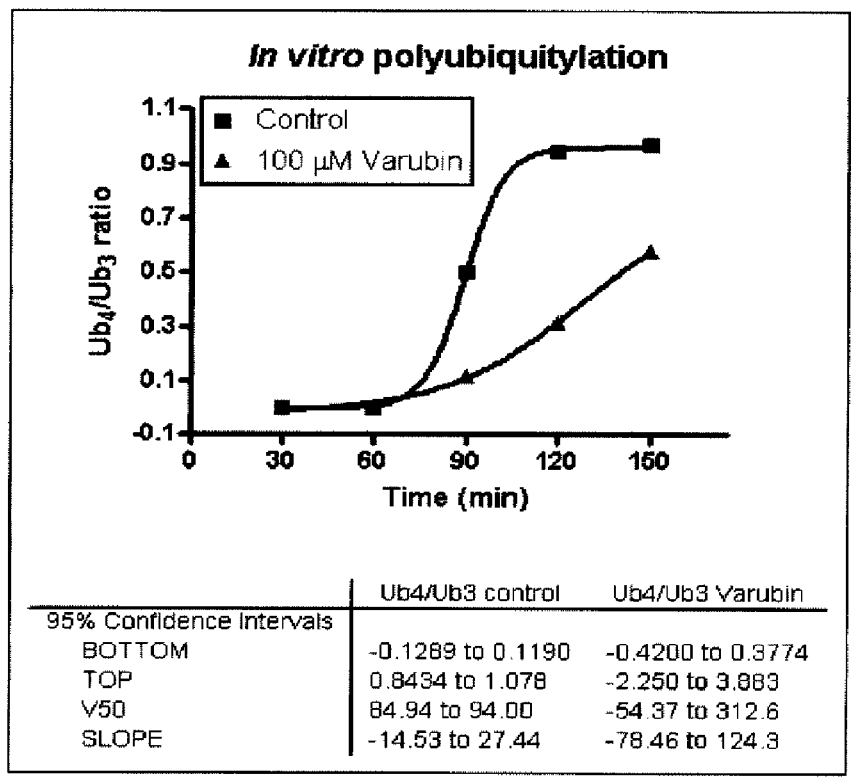
Figure 6:
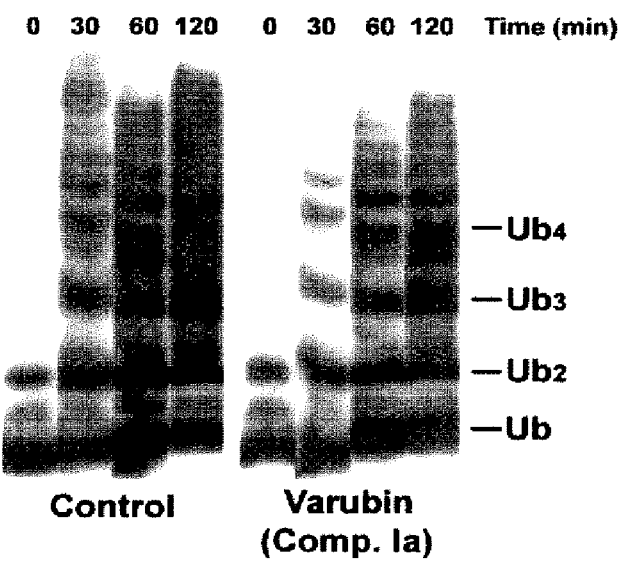

FIG. 6(A) shows that, in the absence of compound Ia, the reaction described above gives rise to the formation of polyubiquitin chains with a size increasing over time, due to the progressive addition of ubiquitin units. The control reaction shows the appearance of triubiquitin ($Ub_3$) at about 30 minutes of reaction, tetraubiquitin ($Ub_4$) at 60 minutes, pentaubiquitin ($Ub_5$) at 90 minutes and forms with a larger size (or complexity) at later times. As shown in FIG. 6(B), the quantitative analysis of the generation of different forms of polyubiquitins indicates that the pre-incubation of UBC13 with 100 µM of compound Varubin (Ia) causes a lower rate of generation of polyubiquitylated forms. The significant difference in the slopes of the curves of the control reactions and those of the treatment with compound Ia also indicates that the inhibition of the enzymatic activity of UBC13-UEV1 by this compound is of the competitive type. This in vitro polyubiquitylation specifically uses the lysine in position 63 of the ubiquitin molecule, since it occurs both with wild-type ubiquitin and when ubiquitin K63 is used in the reaction (FIG. 6(C)), but not when ubiquitin 48 is used instead. Furthermore, the pre-incubation of UBC13 with compound Ia inhibits the polyubiquitylation using ubiquitin K63 as a substrate with an efficiency similar to when the substrate is wild-type ubiquitin (FIG. 6(C)). The conclusion, therefore, is that compound Ia efficiently inhibits K63 type polyubiquitylation catalyzed in vitro by UBC13-UEV1.

Example 6

Biological Activities of Compounds Ia and Ib

Activity in the *Saccharomyces cerevisiae* Yeast.

In the *S. cerevisiae* yeast, K63 type polyubiquitylation, mediated by Ubc13p-Mms2p, of the PCNA protein is crucial for postreplication DNA repair in the RAD6 sub-pathway called "error-free repair" [7-17]. In this pathway, both UBC13 and MMS2 are epistatic with respect to RAD6, although with the peculiarity that the deletion of UBC13, but not MMS2, partially rescues the rad6 phenotype. [14]. Both genes are synergic with mutants of the second repair sub-pathway regulated by RAD6, the so-called "error-prone repair", or mutagenic sub-pathway, in which REV3, REV7 and REV1 participate. This synergy is shown by the fact that the loss of UBC13 or MMS2 causes a higher sensitization of rev3 mutants to genotoxic damage such as ultraviolet irradiation or the exposure to methyl methanesulfonate (MMS) [13-15].

To determine if compounds Ia and Ib inhibit the function of Ubc13p-Mms2p, their capacity to mimic in *S. cerevisiae* the DNA repair phenotypes generated by the null mutation of ubc13 was evaluated. Thus, mutant strains in RAD6 or REV3 and the parent strain thereof (control) were used in viability assays after the exposure to ultraviolet radiation or MMS. The genotypes of the strains used are the following:

1) Parent strain (control) BY4741: MAT at his3Δ1 leu2Δ0 lys2Δ0 ura3Δ0
2) Strain Δrad6: MAT at his3Δ1 leu2Δ0 lys2Δ0 ura3Δ0 rad6::kanMX4
3) Strain Δrev3: MAT at his3Δ1 leu2Δ0 lys2Δ0 ura3Δ0 rev3::kanMX4

Cells were inoculated in liquid cultures with YPD medium overnight at 30° C., until reaching the log phase of growth. For the treatments with ultraviolet radiation, aliquots of cells, grown in the presence or absence of 100 µM of compounds Ia or Ib were irradiated in a Stratalinker instrument (Stratagene) at the energies indicated in FIGS. 7 and 8. For the treatment with the mutagenic agent MMS, aliquots of cells grown or not in medium with 100 µM of compounds Ia or Ib were incubated, 0.03% MMS being added, with subsequent incubation for the times indicated in FIGS. 7 and 8. After either treatment, 500 cells were seeded in plates with YPD medium, counting the colonies after 2 days.

Figure 7:
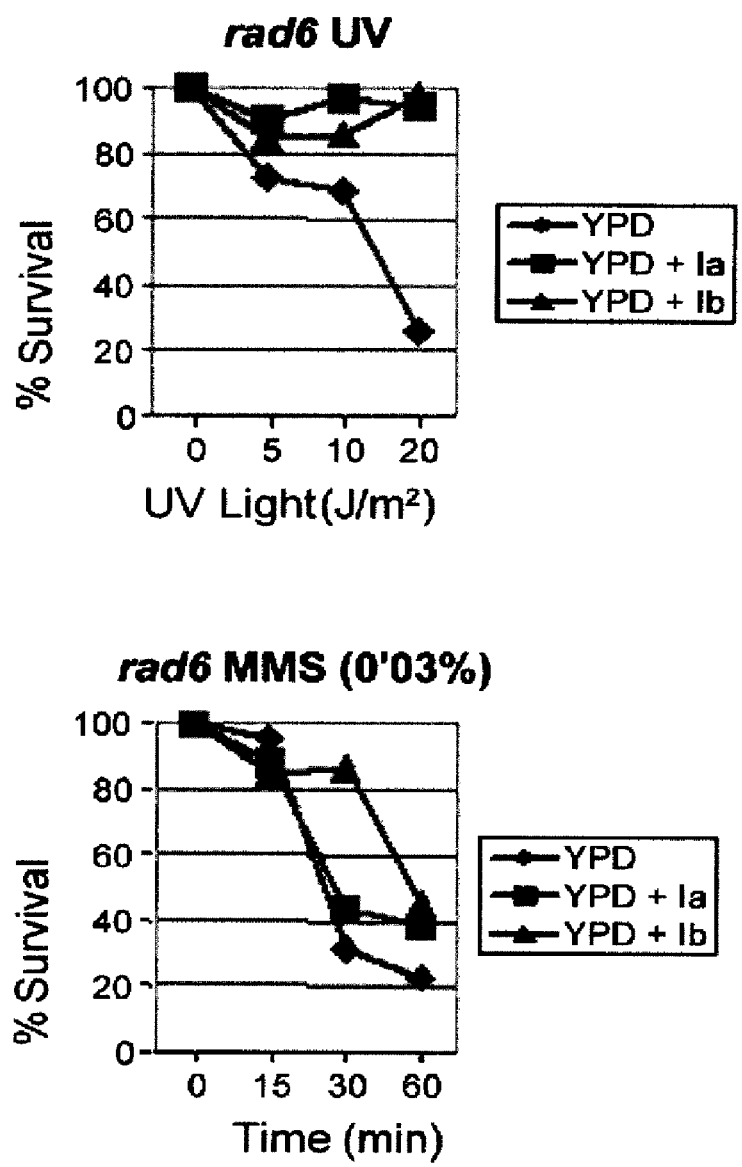
FIG. 7. Sensitization by compounds Ia and Ib to ultraviolet radiation and treatment with methyl methanesulfonate in *S. cerevisiae* Δrad6 mutants. Dose-response curves. *S. cerevisiae* strains lacking RAD6 were subjected to different ultraviolet radiation doses (top graph) or to different times of exposure to 0.03% MMS (bottom graph), without (YPD) or with 100 μM of compound Ia or compound Ib. Survival was determined in relation to cells not subjected to treatment.
Figure 8:
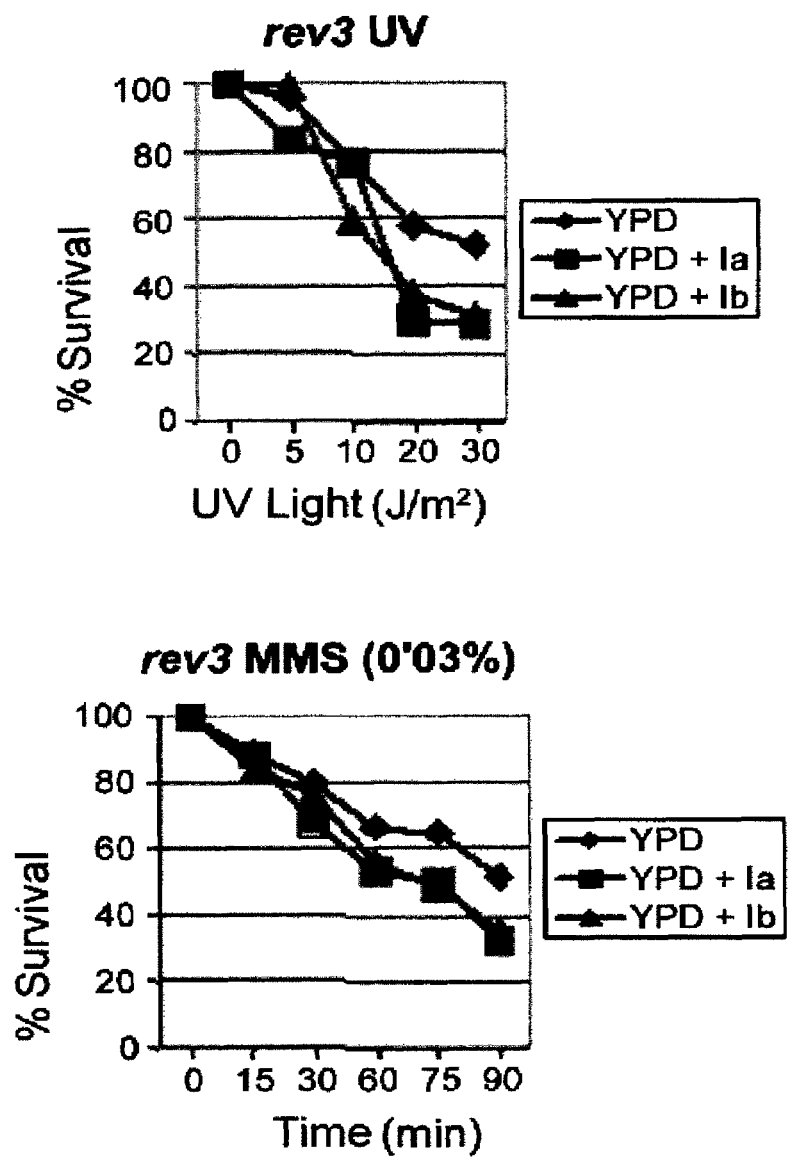
FIG. 8. Sensitization by compounds Ia and Ib to ultraviolet radiation and treatment with methyl methanesulfonate in *S. cerevisiae* Δrev3 mutants. Dose-response curves. *S. cerevisiae* strains lacking REV3 were subjected to different ultraviolet radiation doses (top graph) or to different times of exposure to 0.03% MMS (bottom graph), without (YPD) or with 100 μM of compound Ia or compound Ib. Survival was determined in relation to cells not subjected to treatment.

As expected, in these assays Δrad6 mutants present a high sensitivity both to UV irradiation and to MMS, with a rapid decrease of the survival as the doses of the mutagenic agents are increased (FIG. 7). However, the presence of 100 μM of compound Ia or compound Ib clearly rescued the rad6 phenotype induced by UV irradiation, and to a lesser extent, the phenotype generated by the treatment with MMS (FIG. 7). This is a characteristic phenotype of Δubc13 mutants, and therefore compounds Ia and Ib mimic this phenotype, suggesting that they act through the inhibition of UBC13. On the other hand, the incubation of the Δrev3 mutants with compound Ia and, to a lesser extent, compound Ib, caused a higher sensitization of the cells to the effects of the UV radiation or the exposure to MMS, with a synergy similar to that of a Δubc13 mutation (FIG. 8). Therefore, the two phenotypes analyzed indicate that compounds Ia and Ib affect the DNA repair pathway regulated by RAD6, and that they do so by means of the inhibition of Ubc13p.

Example 7

Biological Activities of Compounds Ia and Ib

Inhibition of the Stimulation of Transcriptional Factor NF-κB by TNFα.

As described in the Background, one of the biochemical pathways regulated by K63 type polyubiquitylation, catalyzed by UBC13-UEV1 (or UBC13-UEV2), is the activation of transcriptional factor NF-κB by signals induced by cytokines, TNFα and other polypeptides.

To determine the activity of compounds Ia and Ib on the stimulation of the NFκ-B activity by TNFα, assays for inducing luciferase activity (determined with the Dual-Luciferase Reporter Assay System kit, Promega, catalog number E1910) generated by expression of the firefly (*Photinus pyralis*) luciferase gene directed by a promoter containing three recognition sites for NFκ-B were performed. To that end, HeLa cells were co-transfected with plasmid pRL-TK, encoding the *Renilla reniformis* Luciferase and being a transfection efficiency control, and plasmid prLUC, a plasmid which allows determining the transcriptional activity of NF-κB, using Fugene (Roche) as a transfection vehicle. 100,000 cells were seeded in 6-well plates (Costar). On the following day, the transfection complex was formed with 0.5 μg of each plasmid and 3 μl of Fugene for 15 minutes. The complex was added to the cells in Optimem medium (InVitrogen), and after 5 hours it was changed to complete medium (Dulbecco's Modified Eagle's Medium with 10% fetal bovine serum, 2 mM of glutamine, supplemented with penicillin and streptomycin), to which the compound Varubin (Ia) or Ib at different concentrations was added or not. On the following day, the cells were incubated with TNFα (10 ng/mL) for 4 hours, after which they were washed with phosphate buffered saline (PBS) and lysated with 250 μL of lysis buffer, following the manufacturer's (Promega) indications. 100 μL of luciferase reagent (LARII) were added to the lysate to measure the firefly luciferase activity, after which the reaction was stopped with 100 μL of stop buffer with *Renilla reniformis* luciferase substrate, this second activity being determined at that time. The firefly luciferase activity was standardized in relation to the *Renilla* luciferase activity. The values corresponding to cells transfected but not stimulated with TNFα were used as standardizers for the remaining experimental values. Finally, a third standardization was performed in which all the values are reflected in relation to the values of induction of luciferase activity by TNFα, without adding the drugs object of the present invention (TNFα control).

Figure 9:
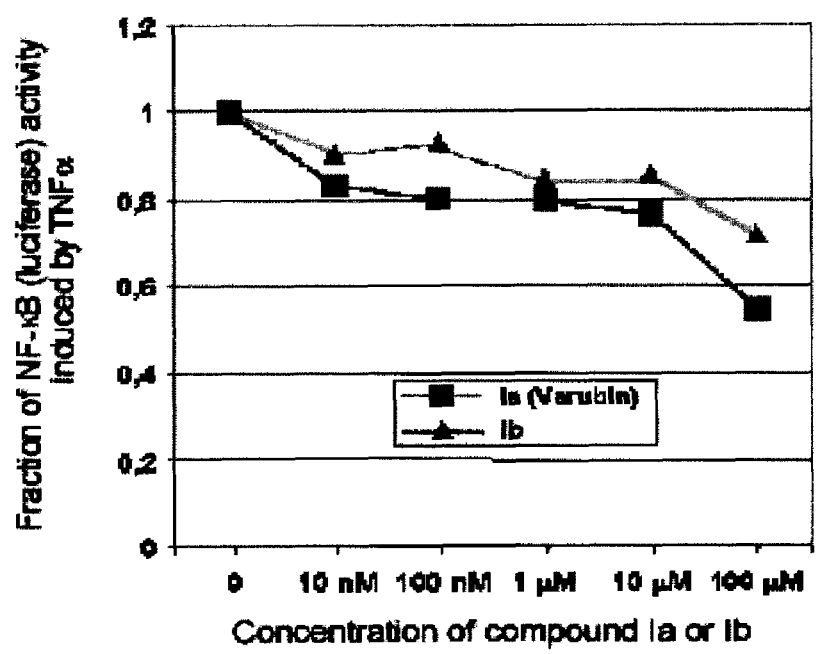
FIG. 9. Inhibition by compounds Ia and Ib of the induction by TNFα of the transactivation of NF-κB. Dose-response curve. HeLa cells transfected with a plasmid indicating NF-κB transcriptional activity (activation of luciferase), and pre-incubated or not with different concentrations of compound Ia or compound Ib, were treated with 10 ng/mL of TNFκ for 2 hours, the activation of NF-κB being quantified. The luciferase activity units have been standardized in relation to the activity induced by TNFα in the absence of compounds Ia or Ib.

FIG. 9 shows that the pre-incubation of HeLa cells with compound Ia or compound Ib inhibits in a dose-dependent manner the stimulation of the transcriptional activity of NF-κB induced by TNFα. This inhibition is greater with compound Ia than with compound Ib, reaching an inhibition of close to 50% of the activation of NF-κB by TNFα when the HeLa cells are pre-incubated with Varubin (Ia) at a concentration of 100 μM. Therefore, compounds Ia and Ib are efficient inhibitors of the activation of NF-κB, whereby they will be applicable in processes in which this activation is important, including inflammatory and neoplastic processes.

Example 8

Biological Activities of Compounds Ia and Ib

Sensitization of Tumor Cells to the Cytotoxic Effects of Doxorubicin and Etoposide.

The activation of transcriptional factor NF-κB is one of the survival mechanisms of normal and tumor cells when they are subjected to different forms of stress or damage [44-47]. Therefore, one of the consequences of the inhibition of the activation of this transcriptional factor is that it causes a higher sensitivity to the cytotoxic effects of different physical or chemical agents, which cause genotoxic damage or another type of cell stress. Therefore, the incubation of cells with compounds Ia or Ib, partly due to their capacity to inhibit the activation of NF-κB, could cause a cell sensitization to the effects of chemotherapeutic agents such as doxorubicin or etoposide. In other words, the combination of doxorubicin or etoposide (at certain doses) with compound Ia or Ib should case a greater cytotoxic effect than doxorubicin or etoposide alone and similar to that which can be caused by larger doses of doxorubicin or etoposide, respectively.

To demonstrate this prediction experimentally, cell count experiments were performed by means of the CyQuant process (Molecular Probes, cat. no. C-7026). This cell quantification method is based on a compound the fluorescence of which is quantitatively stimulated after binding to nucleic acids. 10,000 cells were seeded in each well of 96-well plates, allowing their adhesion to the surface of the plates overnight at 37° C. under an atmosphere of 5% $CO_2$ and 90% humidity, after which the cells were subjected to the different treatments. When the experimental treatments had ended, the wells were washed once with phosphate buffered saline (PBS), the plates then being frozen at −70° C. until the time the CyQuant assay was performed. For the quantification, the plates were thawed at room temperature and 200 μL of lysis buffer containing the CyQuant GR dye were added to each well (following the manufacturer's instructions). After incubating at room temperature for 2-5 minutes, the fluorescence emitted at 480 nm and 520 nm was quantified. To calculate the number of cells corresponding to the fluorimetric readings, standard emitted fluorescence lines were generated according to known numbers of cells, and this data was used to extrapolate the experimental data.

Figure 10:
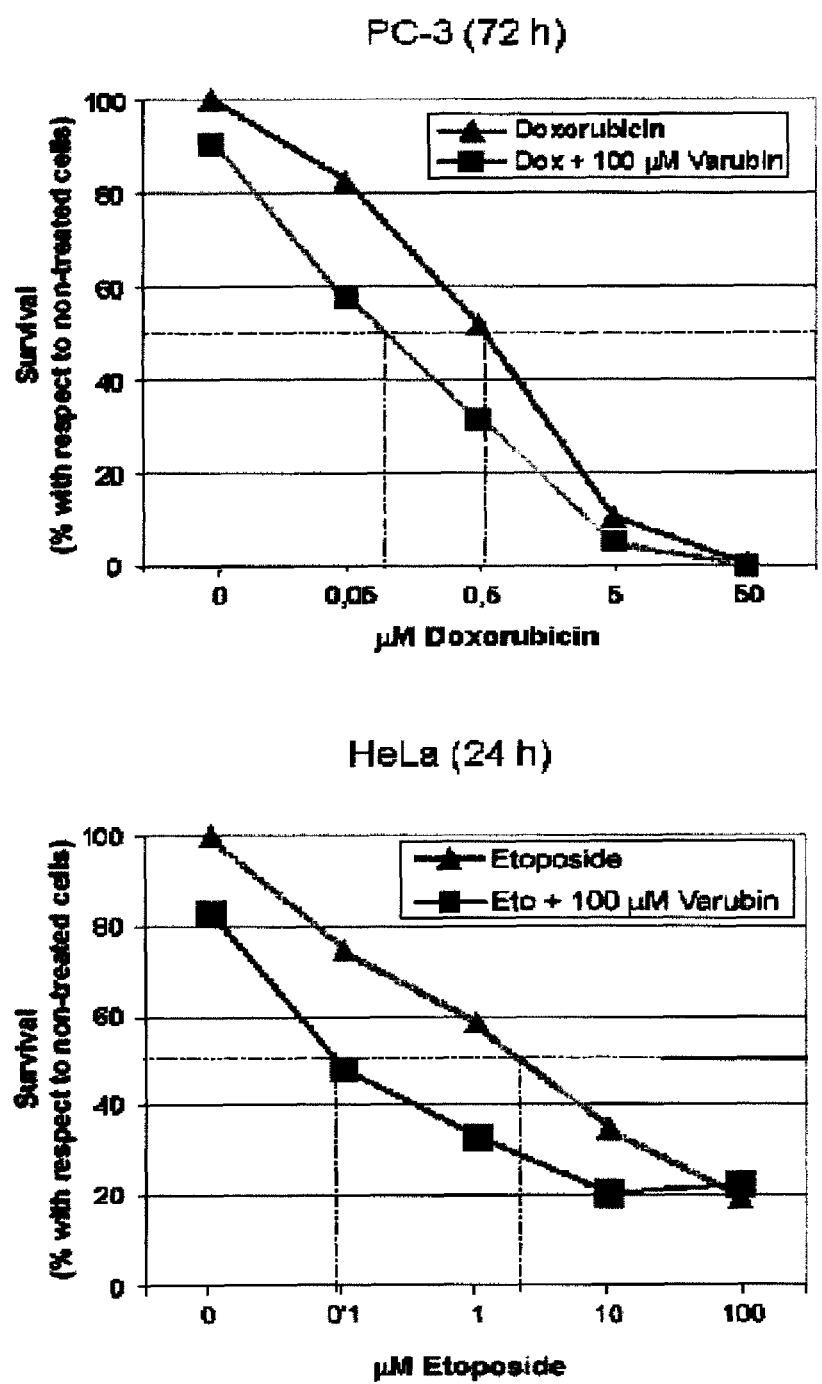
FIG. 10. Sensitization by compound Ia to the cytotoxic effects of doxorubicin in PC-3 cells and to the cytotoxic effects of etoposide in HeLa cells. Dose-response curves. The PC-3 and HeLa cells were pre-incubated, or not, with 100 μM of compound Ia, and were exposed to different doxorubicin or etoposide doses, respectively. The quantification of the surviving cells was performed by means of CyQuant and was standardized with respect to the cells not subjected to treatment.

As shown in FIG. 10, HeLa cells (from a cervical carcinoma) or PC-3 cells (from a prostate carcinoma) were treated with etoposide and doxorubicin, respectively, at concentrations of between 0.05 μM to 50 μM, adding or not 100 μM of compound Ia. From the graph of FIG. 10 it can be deduced that the IC50 for doxorubicin is close to 0.5 μM after 72 hours of treatment in PC-3 cells, and the IC50 for etoposide is approximately 1.25 μM after 24 hours of treatment in HeLa cells. The addition of 100 μM of Ia reduced the IC50 of doxorubicin to 0.1 μM for PC-3 cells and the IC50 of etoposide to 0.04 μM for HeLa cells. Therefore, the treatment with 100 μM of compound Ia causes a sensitization to the cytotoxic effects of doxorubicin of 5 times (PC-3 cells) and a sensitization to the cytotoxic effects of etoposide of 30 times (HeLa cells).

Example 9

Anti-Tumor Activity of Compound Ia (Varubin) as a Chemosensitizing Agent in Murine Models of Human Tumor Cell Xenografts For the purpose of determining if Varubin has an in vivo antitumor activity, its effects in mice having tumors formed from PC-3 cells were analyzed. The experimental tumors were formed by means of the intramuscular inoculation of PC-3.Sluc cells [48]. The latter are PC-3 prostate cells in which they have been integrated by means of transfecting plasmid pRC/CMV-luc, which expresses the firefly (*Photinus pyralis*) luciferase gene in mammalian cells q. The incubation of the PC-3.luc cells with D-luciferin, a luciferase substrate, produces light, which can be quantified in an absolute manner (number of photons) either by means of a luminometer or by means of detection with a CCD (charge-coupled device) camera. The latter process further allows representing in real time images of the location of the tumor cells in the inoculated animals, as well as the tumor size, since the intensity of the light (number of photons) emitted in the presence of luciferin is directly proportional to the number of PC-3.luc cells.

For these studies, 24 male Balb/c nu/nu mice (Charles River Laboratories) of an age of 6 weeks were used. These animals were kept in a pathogen-free environment at all times, having been kept in the animal housing facility for 1 week after they were received, before the experimental handling. After being anesthetized by means of an intraperitoneal (i.p.) injection of a mixture at equal parts of 6 mg/Kg of droperidol (Roche, Basel, Switzerland) and 12 mg/Kg of midazolam (Rovi S.A, Madrid, Spain), intramuscular (i.m.) injections were performed both in the right leg and in the left leg of each animal of $1\times10^6$ PC-3.Sluc cells, suspended in 100 μL of fetal bovine serum-free culture medium. The development of tumors in the inoculation sites was allowed for 2 weeks, after which a first measurement of photons emitted was made and a first capture of images with an ORCA-2BT Imaging System instrument (Hammamatsu Photonics) provided with a C4742-98-LWG-MOD model CCD camera (cooled at −80° C.) was done at a resolution of 512×512 pixels. For the in vivo tracking of the light emission levels of the tumors, the animals were anesthetized as described above, and immediately afterwards the i.p. injection of 150 μl of D-luciferin (Promega), at a dose of 100 mg/Kg, was performed. Four minutes later, photons were detected and quantified for 5 minutes in the instrument described above. The determinations are expressed in relative light units (RLUs). In all the determinations, the background signal, corresponding to areas of the animals far from the tumors (thorax) was subtracted. Immediately after acquiring the first image, an image of the same animal in the same position was taken with visible light. The quantification and the analysis of photons were performed with the aid of the image analysis program WASABI (Hamamatsu Photonics). The transformation of the quantitative information into images was performed in pseudocolors or on grayscale, keeping the same parameters and ranges of intensity and colors for all the animals, such that the gray/black color intensities truly represent the quantitative data, being comparable between experiments and between different animals. For the graphic representations, the quantitative data (RLUs) were standardized, for each tumor, in relation to the RLUs of day 0 of treatment.

Figure 11:
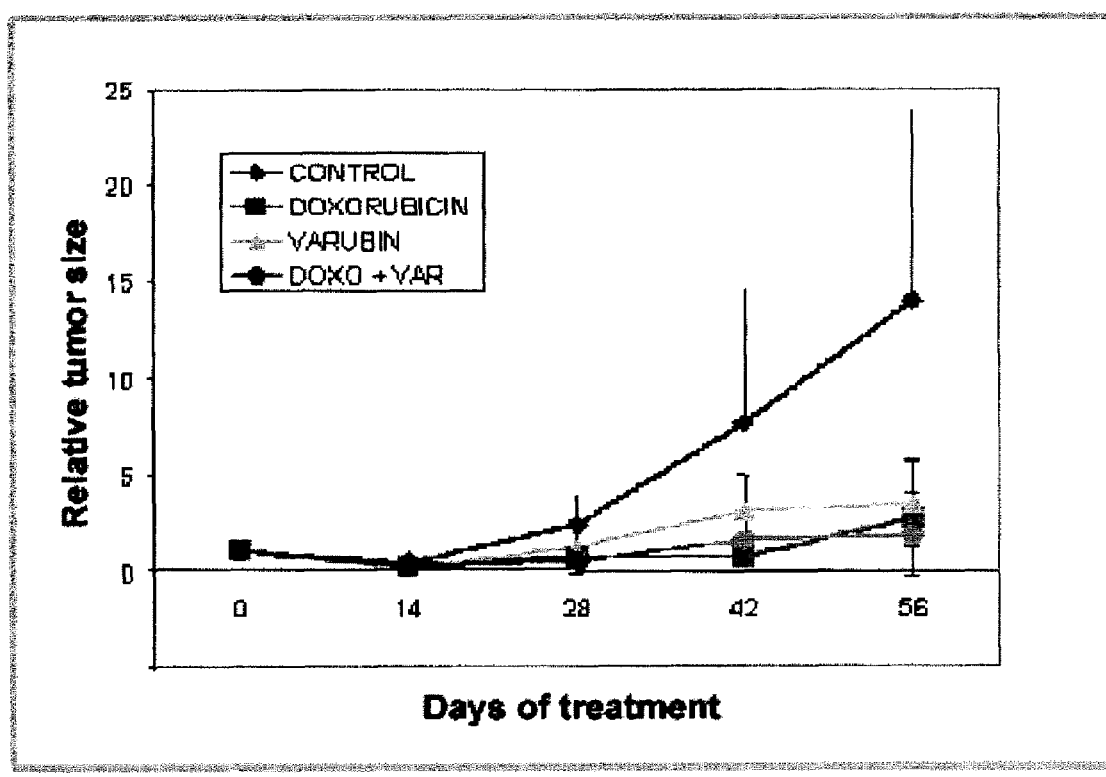
FIG. 11. Graphic representation of the relative sizes of the tumors (RLUs standardized with respect to day 0 of each tumor) of control mice, treated with doxorubicin alone (i.v., 5 mg/Kg, once a week), with Varubin alone (100 μM, i.m., twice a week), or treated with both compounds. The means of between 6 and 8 tumors of each group, with their corresponding standard deviation bars, are represented.
Figure 12:
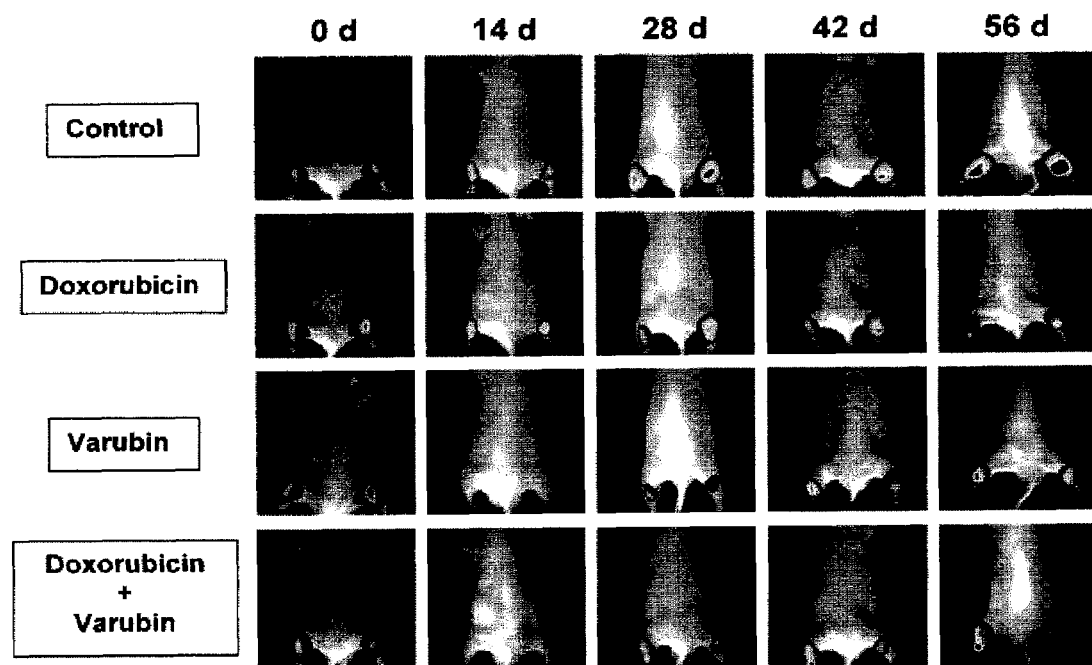
FIG. 12. Images (transformed from pseudocolor to grayscale) corresponding to a representative mouse (the closest one to the mean) of each treatment group (control, doxorubicin alone, Varubin alone, or combined treatment), with sequential tracking over 52 days of the luminosity, captured in a Hamamatsu Photonics instrument (see text for the description of the instrument and the specific model used). The tumors are located in the 2 legs of each animal. Within each tumor, the areas with highest clarity are correlated to those with highest RLUs, and therefore with largest tumor size.

The 24 mice, having luminescent tumors in both legs, were included in 4 experimental groups: (1) Control group, in which an intravenous (i.v.) injection of 100 μL of phosphate buffered saline pH 7.4 (PBS) and 50 μL of intratumoral (i.t.) PBS was performed. (2) Group treated with doxorubicin (Sigma, Alcobendas, Madrid, Spain) i.v., 5 mg/Kg in 100 μL of PBS, once a week. (3) Group treated with Varubin i.t., 100 μM in 50 μL of PBS, twice a week. (4) Group of combined treatment with doxorubicin i.v. once a week and with Varubin twice a week, with the doses and routes of administration indicated above. The light emission of the tumors was analyzed throughout 56 days from the start of the treatment. The results show that the tumors of the control animals grew at a generally constant pace throughout the experiment, except for a decrease 14 days after starting the experiment (FIG. 11). This decrease of RLUs (and therefore of the tumor size) was observed in all the groups, regardless of the treatment of each group, and therefore corresponds to the intrinsic growth pattern of these cells in the xenograft conditions of this experiment. Unlike the tumors of the control mice, the tumors of the mice treated with doxorubicin alone (group 2) hardly experienced growth during the experiment (FIG. 11). Likewise, the mice treated both with doxorubicin i.v. and with Varubin i.m. did not grow significantly during this experiment either. Finally, the tumors of the animals treated with Varubin i.m. alone also presented a very limited growth (without significant differences with respect to those treated with doxorubicin), and in any case significantly less than that of the tumors of the control mice.

Therefore, Varubin shows antitumor activity in this model of tumors transplanted in nu/nu mice, at a concentration of 100 μM, in an intramuscular injection.

LITERATURE

[1] Pickart C M, Eddins M J. Ubiquitin: structures, functions, mechanisms. Biochim Biophys Acta 1695, 55-72, 2004.
[2] Pickart C M, Fushman D. Polyubiquitin chains: polymeric protein signals. Curr Opin Chem Biol 8, 610-616, 2004.
[3] Thrower J S, Hoffman L, Rechsteiner M, Pickart C M. Recognition of the polyubiquitin proteolytic signal. EMBO J 19:94-102, 2000.
[4] Hofmann R M, Pickart C M. In vitro assembly and recognition of Lys-63 polyubiquitin chains. J Biol Chem 276: 27936-27943, 2001.
[5] Spence J, Gali R R, Dittmar G, Sherman F, Karin M, Finley D. Cell cycle-regulated modification of the ribosome by a variant multiubiquitin chain. Cell 102:67-76, 2000.
[6] Hofmann R M, Pickart C M. Noncanonical MMS2-encoded ubiquitin-conjugating enzyme functions in assembly of novel polyubiquitin chains for DNA repair. Cell 96:645-653, 1999.
[7] Hoege C, Pfander B, Moldovan G L, Pyrowolakis G, Jentsch S. RAD6-dependent DNA repair is linked to modification of PCNA by ubiquitin and SUMO. Nature 419: 135-41, 2002.
[8] Torres-Ramos C A, Prakash S, Prakash L. Requirement of RAD5 and MMS2 for postreplication repair of UV-damaged DNA in *Saccharomyces cerevisiae*. Mol Cell Biol 22:2419-2426, 2002.
[9] Haracska L, Torres-Ramos C A, Johnson R E, Prakash S, Prakash L. Opposing effects of ubiquitin conjugation and SUMO modification of PCNA on replicational bypass of DNA lesions in *Saccharomyces cerevisiae*. Mol Cell Biol 24:4267-4274, 2004.

[10] Branzei D, Seki M, Enomoto T. Rad18/Rad5/Mms2-mediated polyubiquitination of PCNA is implicated in replication completion during replication stress. Genes Cells 9:1031-1042, 2004.

[11] Haracska L, Unk I, Prakash L, Prakash S. Ubiquitylation of yeast proliferating cell nuclear antigen and its implications for translesion DNA synthesis. Proc Natl Acad Sci USA 103:6477-82, 2006.

[12] Smirnova M, Klein H L. Role of the error-free damage bypass postreplication repair pathway in the maintenance of genomic stability. Mutat Res 532:117-135, 2003.

[13] Broomfield S, Chow B L, Xiao W. MMS2, encoding a ubiquitin-conjugating-enzyme-like protein, is a member of the yeast error-free postreplication repair pathway. Proc Natl Acad Sci USA 95:5678-5683, 1998.

[14] Brusky J, Zhu Y, Xiao W. UBC13, a DNA-damage-inducible gene, is a member of the error-free postreplication repair pathway in *Saccharomyces cerevisiae*. Curr Genet:168-174, 2000.

[15] Xiao W, Chow B L, Broomfield S, Hanna M. The *Saccharomyces cerevisiae* RAD6 group is composed of an error-prone and two error-free postreplication repair pathways. Genetics 155:1633-1641, 2000.

[16] Tsui C, Raguraj A, Pickart C M. Ubiquitin binding site of the ubiquitin E2 variant (UEV1) protein Mms2 is required for DNA damage tolerance in the yeast RAD6 pathway. J Biol Chem 280:19829-19835, 2005.

[17] Ulrich H D, Jentsch S. Two RING finger proteins mediate cooperation between ubiquitin-conjugating enzymes in DNA repair. EMBO J. 19:3388-3397, 2000.

[18] Chen Z J. Ubiquitin signalling in the NF-kappaB pathway. Nat Cell Biol 7:758-765, 2005.

[19] Deng L, Wang C, Spencer E, Yang L, Braun A, You J, Slaughter C, Pickart C, Chen Z J. Activation of the IkappaB kinase complex by TRAF6 requires a dimeric ubiquitin-conjugating enzyme complex and a unique polyubiquitin chain. Cell 103:351-361, 2000.

[20] Wang C, Deng L, Hong M, Akkaraju G R, Inoue J, Chen Z J. TAK1 is a ubiquitin-dependent kinase of MKK and IKK. Nature 412:346-351, 2001.

[21] Ea C K, Sun L, Inoue J, Chen Z J. TIFA activates IkappaB kinase (IKK) by promoting oligomerization and ubiquitination of TRAF6. Proc Natl Acad Sci USA 101:15318-15323, 2004.

[22] Kanayama A, Seth R B, Sun L, Ea C K, Hong M, Shaito A, Chiu Y H, Deng L, Chen Z J. TAB2 and TAB3 activate the NF-kappaB pathway through binding to polyubiquitin chains. Mol Cell 15:535-548, 2004.

[23] Didier C, Broday L, Bhoumik A, Israeli S, Takahashi S, Nakayama K, Thomas S M, Turner C E, Henderson S, Sabe H, Ronai Z. RNF5, a RING finger protein that regulates cell motility by targeting paxillin ubiquitination and altered localization. Mol Cell Biol 23:5331-5345, 2003.

[24] Duncan L M, Piper S, Dodd R B, Saville M K, Sanderson C M, Luzio J P, Lehner P J. Lysine-63-linked ubiquitination is required for endolysosomal degradation of class I molecules. EMBO J. 25:1635-1645, 2006.

[25] Zhao H, Li C C, Pardo J, Chu P C, Liao C X, Huang J, Dong J G, Zhou X, Huang Q, Huang B, Bennett M K, Molineaux S M, Lu H, Daniel-Issakani S, Payan D G, Masuda E S. A novel E3 ubiquitin ligase TRAC-1 positively regulates T cell activation. J Immunol 174:5288-5297, 2005.

[26] VanDemark A P, Hofmann R M, Tsui C, Pickart C M, Wolberger C. Molecular insights into polyubiquitin chain assembly: crystal structure of the Mms2/Ubc13 heterodimer. Cell 105:711-720, 2001.

[27] Moraes T F, Edwards R A, McKenna S, Pastushok L, Xiao W, Glover J N, Ellison M J. Crystal structure of the human ubiquitin conjugating enzyme complex, hMms2-hUbc13. Nat Struct Biol 8:669-673, 2001.

[28] Pastushok L, Moraes T F, Ellison M J, Xiao W. A single Mms2 "key" residue insertion into a Ubc13 pocket determines the interface specificity of a human Lys63 ubiquitin conjugation complex. J Biol Chem 280:17891-17900, 2005.

[29] Takeuchi T, Yokosawa H. ISG15 modification of Ubc13 suppresses its ubiquitin-conjugating activity. Biochem Biophys Res Commun 336:9-13, 2005.

[30] Zou W, Papov V, Malakhova O, Kim K I, Dao C, Li J, Zhang D E. ISG15 modification of ubiquitin E2 Ubc13 disrupts its ability to form thioester bond with ubiquitin. Biochem Biophys Res Commun 336:61-68, 2005.

[31] Richardson P G, Mitsiades C, Hideshima T, Anderson K C. Bortezomib: proteasome inhibition as an effective anti-cancer therapy. Annu Rev Med 57:33-47, 2006.

[32] Gaczynska M, Osmulski P A. Small-molecule inhibitors of proteasome activity. Methods Mol Biol 301:3-22, 2005.

[33] Tsukamoto S, Yokosawa H. Natural products inhibiting the ubiquitin-proteasome proteolytic pathway, a target for drug development. Curr Med Chem 13:745-754, 2006.

[34] Tsukamoto S, Hirota H, Imachi M, Fujimuro M, Onuki H, Ohta T, Yokosawa H. Himeic acid A: a new ubiquitin-activating enzyme inhibitor isolated from a marine-derived fungus, *Aspergillus* sp. Bioorg Med Chem Lett 15:191-194, 2005.

[35] Masip I, Cortes N, Abad M J, Guardiola M, Perez-Paya E, Ferragut J, Ferrer-Montiel A, Messeguer A. Design and synthesis of an optimized positional scanning library of peptoids: identification of novel multidrug resistance reversal agents. Bioorg Med Chem 13:1923-1929, 2005.

[36] Humet M, Carbonell T, Masip I, Sanchez-Baeza F, Mora P, Canton E, Gobernado M, Abad C, Perez-Paya E, Messeguer A. A positional scanning combinatorial library of peptoids as a source of biological active molecules: identification of antimicrobials. J Comb Chem 5:597-605, 2003.

[37] Plans V, Scheper J, Soler M, Loukili N, Okano Y, Thomson T M. The RING finger protein RNF8 recruits UBC13 for lysine 63-based self polyubiquitylation. J Cell Biochem 97:572-582, 2006.

[38] Case D A, Darden T A, Cheatham T E, III, Simmerling C L, Wang J, Duke R E, Luo R, Merz K M, Wang B, Pearlman D A, Crowley B, Brozell S, Tsui V, Gohlke H, Mongan J, Hornak V, Cui G, Beroza P, Schafmeister C, Caldwell J W, Ross W S, Kollman P A. AMBER 8, University of California, San Francisco, 2004.

[39] Corina Molecular Networks, GmbH Computerchemie Langemarckplatz 1, Erlangen, Germany, 2000.

[40] Besler B H, K. M. Merz K H, Kollman P A. Atomic charges derived from semiempirical methods J Comp Chem 11:431-439, 1990.

[41] Deward M J S, Thiel W. Ground states of molecules. 38. The MNDO method. Approximations and parameters. J Am Chem Soc 99:4899-4907, 1977.

[42] Stewart J J. MOPAC: a semiempirical molecular orbital program. J Comput Aided-Mol Des 4:1-105, 1990.

[43] Pérez C, Ortiz A R. Evaluation of docking functions for protein-ligand docking. J Med Chem 44:3768-3785, 2001.

[44] Huang T T, Wuerzberger-Davis S M, Wu Z H, Miyamoto S. Sequential modification of NEMO/IKKgamma by SUMO-1 and ubiquitin mediates NF-kappaB activation by genotoxic stress. Cell 115:565-576, 2003.

[45] Zerbini L F, Wang Y, Czibere A, Correa R G, Cho J Y, Ijiri K, Wei W, Joseph M, Gu X, Grall F, Goldring M B, Zhou J R, Libermann T A. NF-kappa B-mediated repression of growth arrest- and DNA-damage-inducible proteins 45alpha and gamma is essential for cancer cell survival. Proc Natl Acad Sci USA 101:13618-13623, 2004.

[46] Salvatore C, Camarda G, Maggi C A, Goso C, Manzini S, Binaschi M. NF-kappaB activation contributes to anthracycline resistance pathway in human ovarian carcinoma cell line A2780. Int J Oncol 27:799-806, 2005.

[47] Janssens S, Tinel A, Lippens S, Tschopp J. PIDD mediates NF-kappaB activation in response to DNA damage. Cell 123:1079-1092, 2005.

[48] Wu Z H, Shi Y, Tibbetts R S, Miyamoto S. Molecular linkage between the kinase ATM and NF-kappaB signaling in response to genotoxic stimuli. Science 311:1141-1146, 2006.

[49] Rubio N, Villacampa M M, El Hilali N, Blanco J. Metastatic burden in nude mice organs measured using prostate tumor PC-3 cells expressing the luciferase gene as a quantifiable tumor cell marker. Prostate 44:133-1343, 2000.

The invention claimed is:

1. A method for the treatment of pathologies or diseases associated to metabolic pathways involving the UBC13 enzyme or involving the transcriptional factor NF-κB, comprising administering to a patient a therapeutically effective amount of a compound of formula (I):

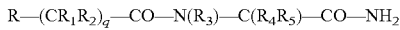

wherein:
R is the radical

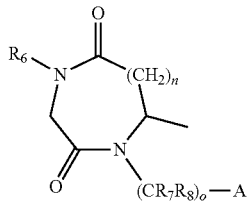

wherein:
$R_6$ is a radical selected from the group consisting of: H, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl and substituted or unsubstituted heterocyclylalkyl;

A is a radical selected from the group consisting of substituted or unsubstituted aryl and substituted or unsubstituted heterocyclyl;

$R_7$ and $R_8$ are independently selected from H, methyl, ethyl, propyl and isopropyl, o is a number selected from the group consisting of 0, 1, 2, 3 and 4, n is a number selected from the group consisting of 0 and 1, the line — indicates the bonding site of the radical R with the rest of the molecule of formula (I);

$R_1$ and $R_2$ are independently selected from the group consisting of H, methyl, ethyl, propyl and isopropyl;

$R_3$ is a radical selected from the group consisting of: H, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heterocyclyl, and substituted or unsubstituted heterocyclylalkyl;

$R_4$ and $R_5$ are independently selected from the group consisting of H, methyl, ethyl, propyl and isopropyl; and q is a number selected from the group consisting of 0 and 1;

or a pharmaceutically acceptable salt or stereoisomer thereof.

2. The method according to claim 1, wherein in compound of formula (I), $R_6$ is a radical selected from the group consisting of H, substituted or unsubstituted arylalkyl and substituted or unsubstituted heterocyclylalkyl, and in that $R_3$ is a radical selected from H, substituted or unsubstituted arylalkyl and substituted or unsubstituted heterocyclylalkyl, or a pharmaceutically acceptable salt or stereoisomer thereof.

3. The method according to claim 2, wherein in compound of formula (I) $R_6$ is a radical selected from the group consisting of substituted or unsubstituted phenylpropyl, substituted or unsubstituted phenylethyl, substituted or unsubstituted benzyl, substituted or unsubstituted furylpropyl, substituted or unsubstituted furylethyl, substituted or unsubstituted furylmethyl, substituted or unsubstituted imidazolylpropyl, substituted or unsubstituted imidazolylethyl, substituted or unsubstituted imidazolylmethyl, substituted or unsubstituted pyridinylpropyl, substituted or unsubstituted pyridinylethyl, substituted or unsubstituted pyridinylmethyl, substituted or unsubstituted piperidinylpropyl, substituted or unsubstituted piperidinylethyl, substituted or unsubstituted piperidinylmethyl; and in that $R_3$ is a radical selected from substituted or unsubstituted phenylpropyl, substituted or unsubstituted phenylethyl, substituted or unsubstituted benzyl, substituted or unsubstituted furylpropyl, substituted or unsubstituted furylethyl, substituted or unsubstituted furylmethyl, substituted or unsubstituted imidazolylpropyl, substituted or unsubstituted imidazolylethyl, substituted or unsubstituted imidazolylmethyl, substituted or unsubstituted pyridinylpropyl, substituted or unsubstituted pyridinylethyl, substituted or unsubstituted pyridinylmethyl, substituted or unsubstituted piperidinylpropyl, and substituted or unsubstituted piperidinylethyl, substituted or unsubstituted piperidinylmethyl, or a pharmaceutically acceptable salt or stereoisomer thereof.

4. The method according to claim 3, wherein in compound of formula (I) $R_6$ is a radical substituted with one or more of fluorine, chlorine, bromine, trifluoromethyl, hydroxyl, alkoxyl, alkylcarbonyl, alkylamino and sulfonamino, cyano, nitro, nitrite, nitrate, thionitrate, carboxamido or a pharmaceutically acceptable salt or stereoisomer thereof.

5. The method according to claim 3, wherein in compound of formula (I) $R_3$ is a radical substituted with one or more of fluorine, chlorine, bromine, trifluoromethyl, hydroxyl, alkoxyl, alkylcarbonyl, alkylamino and sulfonamino, cyano, nitro, nitrite, nitrate, thionitrate, carboxamido or a pharmaceutically acceptable salt or stereoisomer thereof.

6. The method according to claim 1, wherein in compound of formula (I) $R_6$ is the radical p-fluorophenylethyl or 2,4-dichlorophenylethyl, or a pharmaceutically acceptable salt or stereoisomer thereof.

7. The method according to claim 1, wherein in compound of formula (I) A is a phenyl substituted with chlorine, fluorine and/or bromine, and o is a number selected from 1, 2 and 3, or a pharmaceutically acceptable salt or stereoisomer thereof.

8. The method according to claim 1, wherein in compound of formula (I) $R_7$ and $R_8$ are both H, o is 2, and A is p-fluorophenyl or a pharmaceutically acceptable salt or stereoisomer thereof.

9. The method according to claim 1, wherein in compound of formula (I) $R_3$ is 2-pyridylethyl, 2,4-dichlorophenylethyl or 4-methoxyphenylethyl, or a pharmaceutically acceptable salt or stereoisomer thereof.

10. The method according to claim 1, wherein in compound of formula (I) n is 1 or 0, or a pharmaceutically acceptable salt or stereoisomer thereof.

11. The method according to claim 1, wherein in compound of formula (I) q is 0 or 1, or a pharmaceutically acceptable salt or stereoisomer thereof.

12. The method according to claim 1, wherein compound of formula (I) has formula Ia (N-aminocarbonylmethyl-N-(2'-(2"pyridyl)ethyl)-1,4-bis[2'-(4"-fluorophenyl)ethyl]-3,7-dioxo-[1,4]diazepane-5-carboxamide):

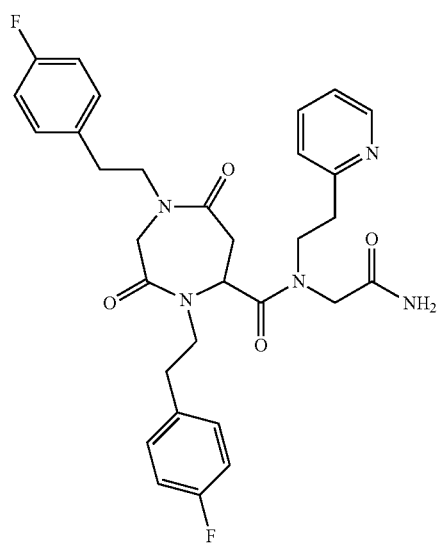

(Ia)

or a pharmaceutically acceptable salt or stereoisomer thereof.

13. The method according to claim 1, wherein compound of formula (I) has formula Ib (1,4-bis[2'-(4"-fluorophenyl)ethyl]-2-[N-aminocarbonylmethyl-N-(2'-(2"pyridyl)ethyl)amino-carbonylmethyl]piperazine-3,6-dione):

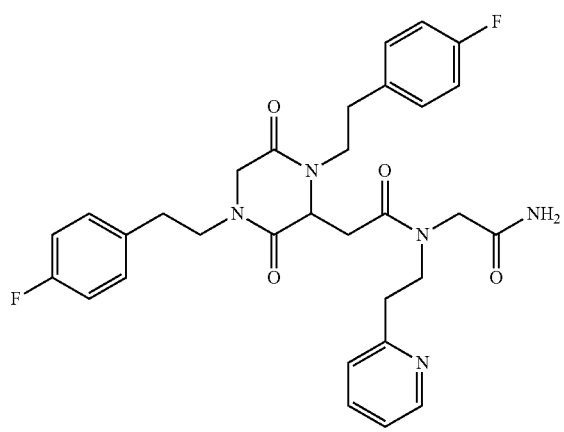

(Ib)

or a pharmaceutically acceptable salt or stereoisomer thereof.

14. The method according to claim 1, wherein compound of formula (I) has one of the following formulas:

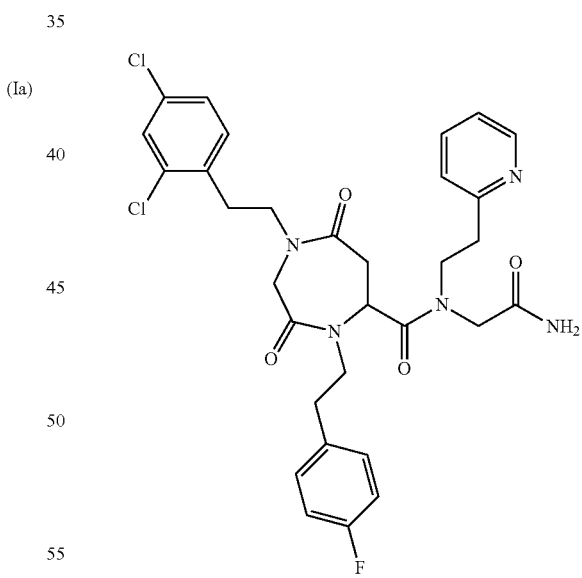

N-aminocarbonylmethyl-N-(2'-(2"-pyridyl)ethyl)-1-[2'-(2",4"-dichlorophenyl)ethyl]-4-[2'-(4"-fluorophenyl)ethyl]-3,7-dioxo-[1,4]diazepane-5-carboxamide

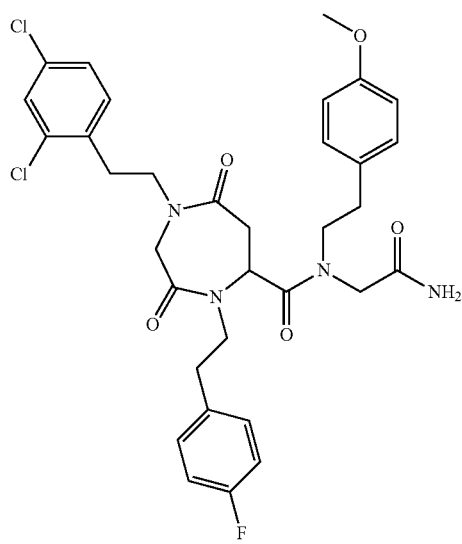

N-aminocarbonylmethyl-N-(2'-(4''-methoxyphenyl)ethyl)-1-[2'-(2'',4''-dichlorophenyl)ethyl]-4-[2'-(4''-fluorophenyl)ethyl]-3,7-dioxo-[1,4]diazepane-5-carboxamide

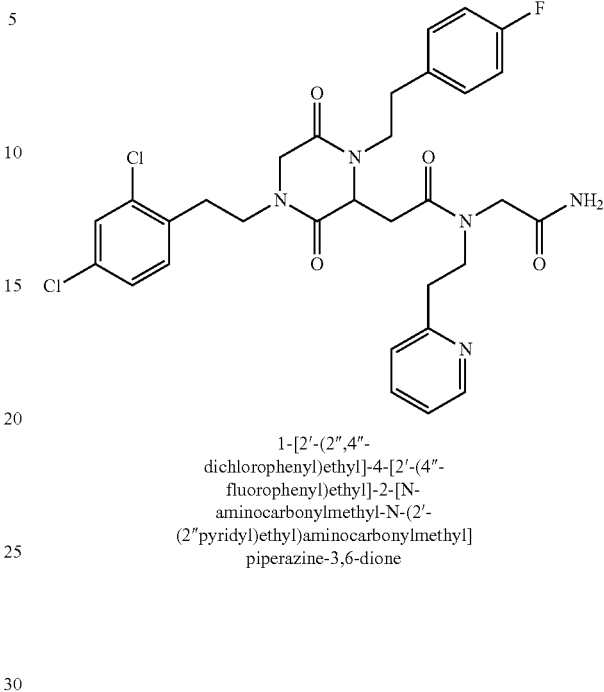

1-[2'-(2'',4''-dichlorophenyl)ethyl]-4-[2'-(4''-fluorophenyl)ethyl]-2-[N-aminocarbonylmethyl-N-(2'-(2''pyridyl)ethyl)aminocarbonylmethyl] piperazine-3,6-dione

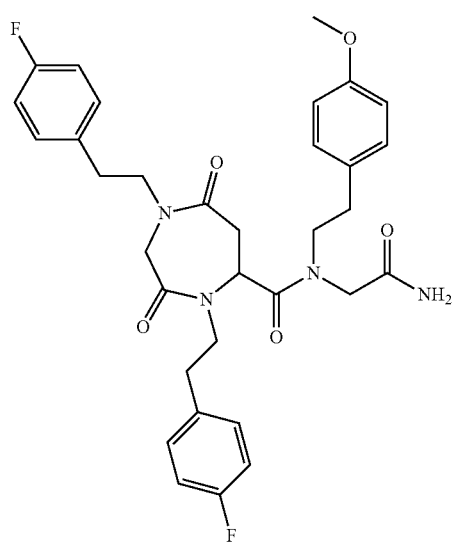

N-aminocarbonylmethyl-N-(2'-(4''-methoxyphenyl)ethyl)-1-4-bis[2'-(4''-fluorophenyl)ethyl]-3,7-dioxo-[1,4]diazepane-5-carboxamide

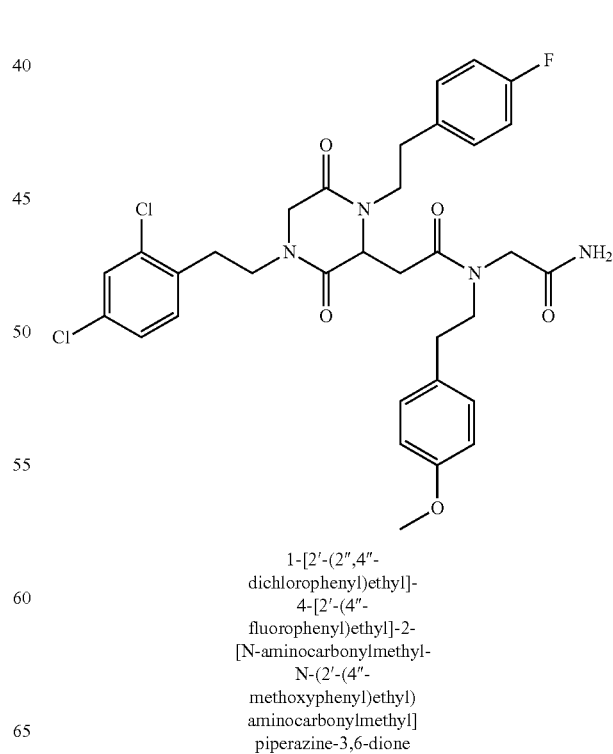

1-[2'-(2'',4''-dichlorophenyl)ethyl]-4-[2'-(4''-fluorophenyl)ethyl]-2-[N-aminocarbonylmethyl-N-(2'-(4''-methoxyphenyl)ethyl)aminocarbonylmethyl] piperazine-3,6-dione

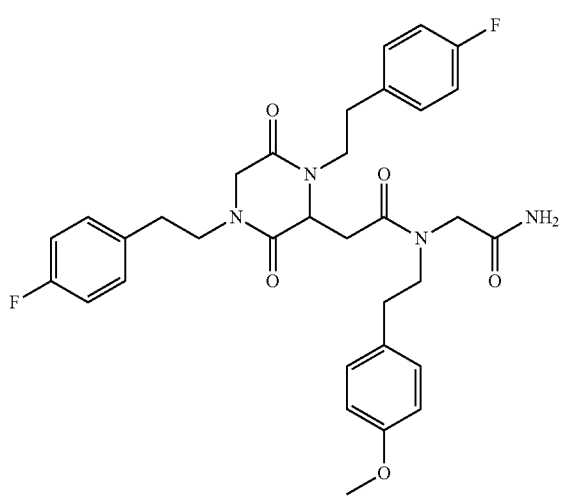

1,4-bis[2'-(4"-fluorophenyl)ethyl]-
2-[N-aminocarbonylmethyl-N-(2'-(4"-
methoxyphenyl)ethyl)aminocarbonylmethyl]
piperazine-3,6-dione

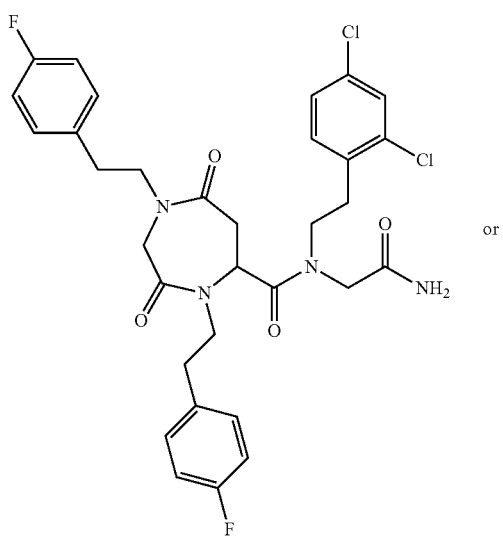

N-aminocarbonylmethyl-
N-[2'-(2",(4"-
dichlorophenyl)ethyl)-
1,4-bis[2'-(4"-
fluorophenyl)ethyl]-
3,7-dioxo-
[1,4]diazepane-5-
carboxamide or

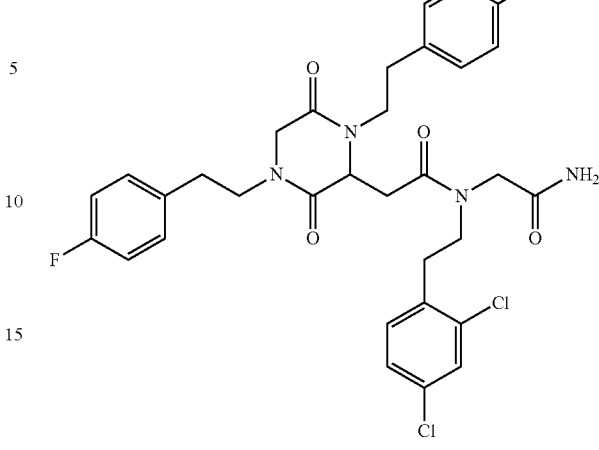

[1,4-bis[2'-(4"-
fluorophenyl)ethyl]-2-[N-
aminocarbonylmethyl-N-(2'-(2",4"-
dichlorophenyl)ethyl)aminocarbonylmethyl]
piperazine-3,6-dione.

15. The method according to claim 1, for the treatment of pathologies or diseases associated to metabolic pathways involving the UBC13 enzyme, which are inflammatory disease autoimmune disease, cancer or neoplasia.

16. The method according to claim 15, wherein the method is for treatment of inflammatory disease or autoimmune disease, and the inflammatory disease or autoimmune disease is: inflammatory bowel disease, inflammatory joint pathologies, atopic dermatitis and other inflammatory dermatological pathologies, neuritis, encephalitis, encephalomyelitis and inflammatory pathologies affecting the central or peripheral nervous system, myositis, vasculitis, systemic lupus erythematosus, infectious diseases presenting inflammation, host versus graft rejection reactions, conjunctivitis and inflammatory oculopathies, otitis or mucositis, or
wherein the method is for treatment of cancer or neoplasia, and the cancer or neoplasia is prostate, breast, lung, pancreatic, colorectal, gastric, esophageal, laryngeal, thyroid, hepatic, urinary bladder, renal, uterine and cervical carcinoma; osteosarcoma, soft tissue sarcoma and angiosarcoma; hematopoietic tumor including leukemias and lymphomas, neuroblastomas, glioblastomas and astrocytomas, melanoma, basal cell dermal carcinoma or squamous cell dermal carcinoma.

17. A method for the treatment of a tumor by antagonism or inhibition of the genotoxic damage tolerance pathway mediated by PCNA and RAD6 causing chemo- or radiosensitizing effects, increasing the sensitivity of a prostate or cervical cell tumor in a patient to doxorubin or etoposide, comprising administering to the patient a therapeutically effective amount of a compound of formula (I) as defined in claim 1 or a pharmaceutically acceptable salt or stereoisomer thereof.

\* \* \* \* \*